US012768837B2

(12) United States Patent
Wang et al.

(10) Patent No.: US 12,768,837 B2
(45) Date of Patent: Oct. 20, 2026

(54) METHOD FOR REMOVING PROTEIN CORONA OF THE SURFACE OF NANOMETER PARTICLE

(71) Applicant: ZHEJIANG UNIVERSITY, Zhejiang (CN)

(72) Inventors: Guowei Wang, Zhejiang (CN); Pintong Huang, Zhejiang (CN); Yifan Jiang, Zhejiang (CN); Chao Zhang, Zhejiang (CN); Tao Lin, Zhejiang (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 823 days.

(21) Appl. No.: 18/111,571

(22) Filed: Feb. 19, 2023

(65) Prior Publication Data

US 2024/0094197 A1 Mar. 21, 2024

(30) Foreign Application Priority Data

Sep. 5, 2022 (CN) ......................... 202211077201.2
Sep. 23, 2022 (CN) ......................... 202211162306.8

(51) Int. Cl.
*G01N 33/543* (2006.01)
*C12N 13/00* (2006.01)
*G01N 33/50* (2006.01)
*G01N 33/53* (2006.01)

(52) U.S. Cl.
CPC ....... *G01N 33/54313* (2013.01); *C12N 13/00* (2013.01); *G01N 33/5011* (2013.01); *G01N 33/5306* (2013.01); *G01N 33/54393* (2013.01)

(58) Field of Classification Search
CPC ........... G01N 33/5306; G01N 33/5011; G01N 33/54313; G01N 33/54393
See application file for complete search history.

(56) References Cited

PUBLICATIONS

Jonathan Shannahan.The biocorona: a challenge for the biomedical application of nanoparticles. Nanotechnol Rev. 6 (4): 345-353 (Aug. 2017).*

Adamson et al. Experimental challenges regarding the in vitro investigation of the nanoparticle-biocorona in disease states. Toxicol In Vitro 51: 40-49 (Sep. 2018).*

* cited by examiner

*Primary Examiner* — Gailene Gabel
(74) *Attorney, Agent, or Firm* — Adam Warwick Bell; Matthew Rupert Kaser

(57) ABSTRACT

The present invention relates to a method for removing protein corona on the surface of nanometer particle. Specifically, the invention provides a method for removing protein corona of protein corona modified nanometer particle, the method comprises the following steps: subjecting the protein corona modified nanometer particle to ultrasound stimulation to remove the protein corona of the protein corona modified nanometer particle; the nanometer particle comprises perfluoropentane. Ultrasound stimulation can remove protein corona on the surface of nanometer particle, overcome the masking effect of the protein corona on the ligand modified on the surface of nanometer particle, and prevent the protein corona from blocking the binding of the ligand modified on the surface of nanometer particle to cell receptor.

5 Claims, 13 Drawing Sheets

A

B

| Total protein content in protein corona (μg/mg lipids) | Without ultrasound stimulation treatment | With ultrasound stimulation treatment |
|---|---|---|
| GL | 21.23±4.41 | 20.65±2.79 |
| LGL | 21.94±3.53 | 19.51±2.46 |
| PGL | 23.72±3.66 | 4.13±1.21 |
| LPGL | 24.16±3.28 | 4.71±1.44 |

LPGL liposome in PBS 7.4

LPGL liposome in plasma treated without ultrasound stimulation

LPGL liposome in plasma treated with ultrasound stimulation

Plasma

PGL liposome in plasma treated without ultrasound stimulation

PGL liposome in plasma treated with ultrasound stimulation

GL

LGL

PGL

5B

| Total protein content in protein corona (μg/mg lipids) | Without ultrasound stimulation treatment | With ultrasound stimulation treatment |
|---|---|---|
| GL | 21.23±4.41 | 20.65±2.79 |
| LGL | 21.94±3.53 | 19.51±2.46 |
| PGL | 23.72±3.66 | 4.13±1.21 |
| LPGL | 24.16±3.28 | 4.71±1.44 |

8A

The mixture of Cy5-labeled LPGL liposome and serum-free medium was incubated with BxPC3 cells, and treated without ultrasound stimulation The mixture of Cy5-labeled LPGL liposome and 10 % FBS (fetal bovine serum)-containing medium was incubated with BxPC3 cells, and treated without ultrasound stimulation The mixture of Cy5-labeled LPGL liposome and 10 % FBS (fetal bovine serum)-containing medium was incubated with BxPC3 cells, and treated with ultrasound stimulation

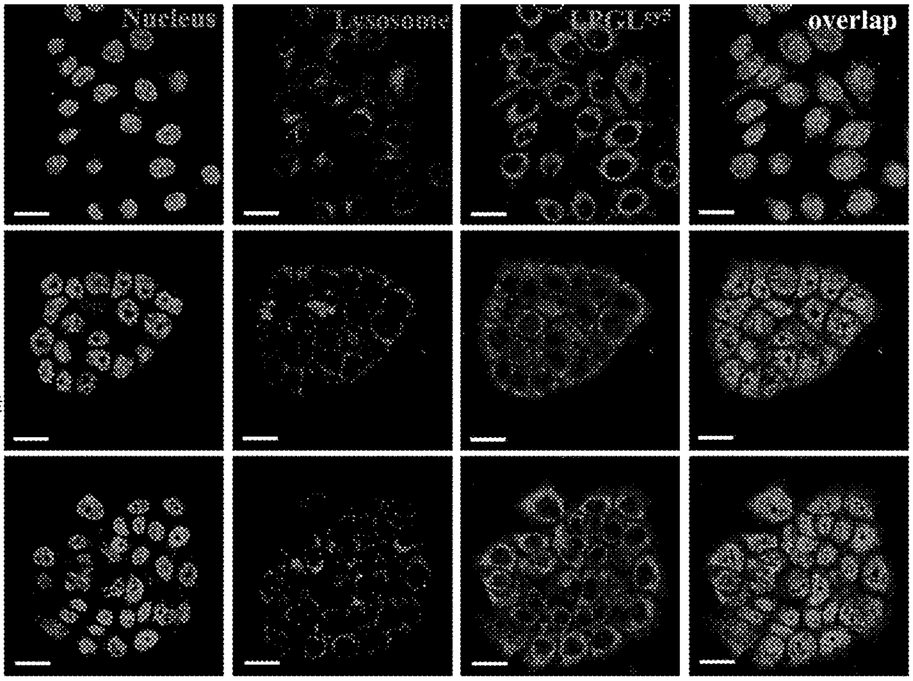

8B

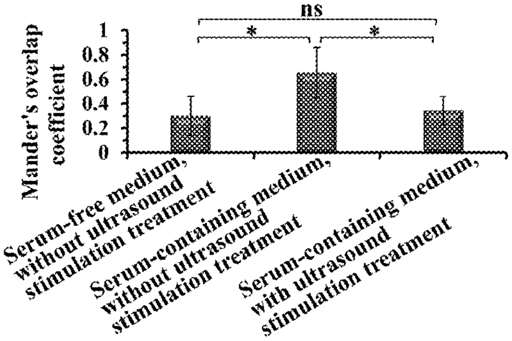

Fig. 8

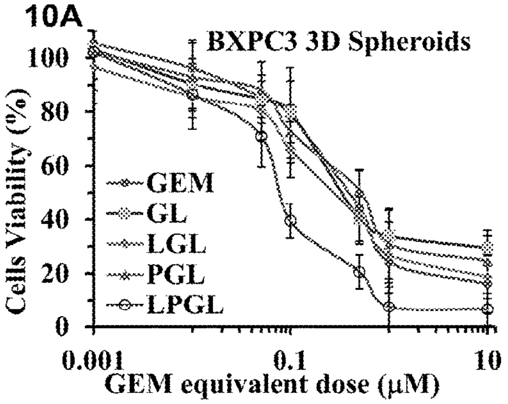
10B
| Groups \ $IC_{50}$ (μM) | BXPC3 spheroid | Huh7 spheroid |
|---|---|---|
| GEM | 0.49 ± 0.12 | 0.44 ± 0.08 |
| GL | 1.12 ± 0.27 | 0.98 ± 0.22 |
| LGL | 0.89 ± 0.21 | 0.65 ± 0.16 |
| PGL | 1.04 ± 0.19 | 0.97 ± 0.15 |
| LPGL | 0.21 ± 0.08 | 0.18 ± 0.07 |
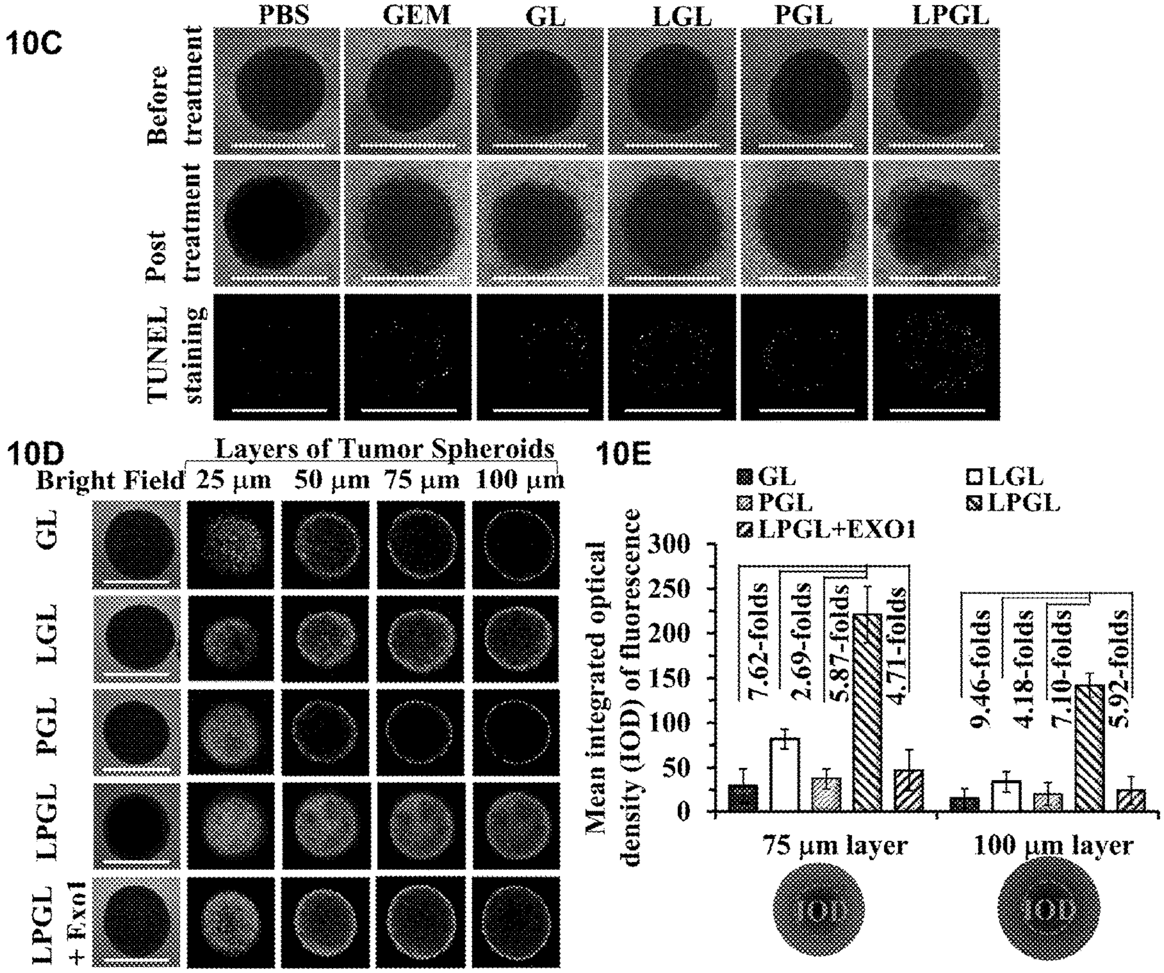
Fig. 10

METHOD FOR REMOVING PROTEIN CORONA OF THE SURFACE OF NANOMETER PARTICLE

The present application claim the benefit of prior applications CN patent application Ser. No. 2022110772012 filed Sep. 5, 2022 and CN patent application Ser. No. 2022111623068 filed Sep. 23, 2022, both of which are fully incorporated by reference herewith. Additionally all publications of any kind mentioned in this disclosure are further fully incorporated by reference herewith.

TECHNICAL FIELD

The present invention relates to the field of medicine. Specifically, the present invention relates to a method for removing protein corona on the surface of nanometer particle.

BACKGROUND TECHNOLOGY

Ligand/receptor mediated drug-loaded nanometer particle such as nanoparticle and liposome is used to improve the anti-tumor effect of drug, especially for lowly permeable solid tumor such as liver cancer or pancreatic cancer. Since the tumor vascular endothelial cells of lowly permeable solid tumor are well organized and tightly stacked and the gap between vascular endothelial cells is small, even the drug is delivered to the vessels of tumor, it is difficult for the drug to effectively reach the microenvironment of the tumor site through the gap of vascular endothelial cells because the drug is blocked by well organized and tightly stacked tumor vascular endothelial cells. Therefore, the anti-tumor drugs can not effectively penetrate into the tumor site from the gap of tumor vessels to exert anti-tumor effect on tumors with low vascular permeability via the traditional Enhanced Permeability and Retention effect (EPR effect). As for lowly permeable solid tumors, the ligand modified on the drug-loaded nanometer particle specifically binds to the receptor of the surface of tumor vascular endothelial cells, and the ligand/receptor binding mediates the endocytosis and exocytosis of the drug-loaded nanometer particle by tumor vascular endothelial cells to promote the drug-loaded nanometer particle to penetrate into tumor site from the blood to enhance the anti-tumor effect. Additionally, the binding of ligand/receptor can also mediate the uptake of drug-loaded nanometer particle by tumor cells, thus enhancing the anti-tumor effect of drug-loaded nanoparticles.

However, the surface of the nanometer particle adsorbs protein to form protein corona in protein-containing environment such as blood, tumor microenvironment or serum-containing medium. The protein corona can act as a fluid biological barrier to mask the ligand on the surface of nanometer particle, thus preventing the ligand on the surface of nanometer particle from binding to the ligand on the surface of tumor vascular endothelial cells or tumor cells, the ligand/receptor mediated endocytosis and exocytosis of nanometer particle cannot be realized. For example, the protein corona masks the ligand modified on the surface of drug-loaded nanometer particle in the blood, thus the protein corona inhibits endocytosis and exocytosis of drug-loaded nanometer particle in the tumor vascular endothelial cells mediated by the binding of ligand on the surface of the drug-loaded nanometer particle to receptor on the surface of the tumor vascular endothelial cells, thus preventing the ligand-modified nanometer particle from penetrating into the tumor site from the blood, and reducing the antitumor effect of drug, which is the main reason why the existing ligand-modified nanometer particle can not effectively penetrate into tumor site from tumor vessels to exert a target therapy. Moreover, the protein corona block the binding of the ligand modified on the surface of nanometer particle to tumor cell receptor, thus inhibiting the uptake of the ligand-modified nanometer particle in tumor cell, and reducing confirm that we will be paid the fee for thi the antitumor effect of drug loaded in the ligand-modified nanometer particle. Furthermore, in the experiment of screening or identifying potential ligand targeting cell by modifying the ligand to be tested on the surface of nanometer particle, the nanometer particle modified by the ligand to be tested usually need to be incubated with cells in protein-containing condition (e.g., serum-containing medium) to screen and identify the potential ligand targeting cell, especially for cells that need to be cultured in protein-containing condition (e.g., serum-containing medium), whereas the surface of the nanometer particle adsorb protein and the protein corona can be formed on the surface of nanometer particle in the protein-containing condition (e.g., serum-containing medium), the protein corona block the binding of the ligand to be tested modified on the surface of nanometer particle to the cell surface receptor, therefore, it is difficult to effectively and accurately screen and identify whether the ligand to be tested can target cell or cell receptor in the protein-containing condition (e.g., serum-containing medium) in vitro, especially in the case the amount of the ligand to be tested is small and false negative results are likely to occur, which limits the development of ligand targeting cell.

In addition, the existing drug-loaded nanometer particle have many advantages, such as low biological safety, retention and degradation in lysosome. The enzymes in the lysosome can degrade the nanometer particle and the drug loaded in the nanometer particle, thus reducing the therapeutic effect.

Therefore, it is need to develop a method for removing protein corona on the surface of nanometer particle to overcome the masking effect of protein corona on the ligand modified on the surface of nanometer particle, thereby effectively realizing the therapy of the ligand-modified nanometer particle and the screening, identification and development of potential ligand targeting the cell in the protein-containing condition.

SUMMARY OF THE INVENTION

It is an object of the present invention to provide a nanometer particle, ultrasound stimulation can effectively remove protein corona on the surface of nanometer particle to overcome the masking effect of the protein corona on the ligand modified on the surface of the nanometer particle.

In the first aspect of the present invention, it provides a nanometer particle, the nanometer particle comprises perfluoropentane.

Preferably, the nanometer particle is nanoparticle or liposome.

Preferably, the nanometer particle encapsulates perfluoropentane.

Preferably, the nanoparticle comprises nanomaterial.

Preferably, the nanomaterial comprises amphiphilic nanomaterial.

Preferably, the nanomaterial comprises nanomaterial of the nanoparticle and/or lipid material of the liposome.

Preferably, the amphiphilic nanomaterial comprises amphiphilic nanomaterial of the nanoparticle and/or lipid material of the liposome.

Preferably, the liposome comprises lipid material.

Preferably, the lipid material is selected from the group consisting of 1,2-dipalmitoyl-sn-glycero-3-phosphocholine (DPPC), 1,2-distearoyl-sn-glycero-3-phosphoethanolamine-N-[methoxy (polyethylene glycol)] (DSPE-PEG), 1,2-dioleoyl-sn-glycero-3-phosphoethanolamine (DOPE), soy bean phospholipid, phosphatidylcholine (PC, lecithin), cholesterol, phosphatidylethanolamine (PE, cephalin), phosphatidylserine (PS), phosphatidylinositol (PI), phosphatidylglycerol (PG), dicetyl phosphate (DCP), dimyristoylphosphatidylcholine (DMPC), distearoylphosphatidylcholine (DSPC), dilaurylphosphatidylcholine (DLPC), dioleoylphosphatidylcholine (DOPC), and combinations thereof.

Preferably, the lipid material comprises 1,2-dipalmitoyl-sn-glycero-3-phosphocholine (DPPC) and 1,2-distearoyl-sn-glycero-3-phosphoethanolamine-N-[methoxy (polyethylene glycol)] (DSPE-PEG).

Preferably, the 1,2-distearoyl-sn-glycero-3-phosphoethanolamine-N-[methoxy (polyethylene glycol)](DSPE-PEG) is selected from the group consisting of DSPE-PEG600, DSPE-PEG800, DSPE-PEG1000, DSPE-PEG2000, DSPE-PEG4000, DSPE-PEG6000, and combinations thereof.

Preferably, the DPPC is 1-10 parts by weight, preferably 2-8 parts by weight, more preferably 4-6 parts by weight, most preferably 3 parts by weight.

Preferably, the DSPE-PEG is 0.5-8 parts by weight, preferably 1-5 parts by weight, more preferably 1-3 parts by weight, most preferably 2 parts by weight.

Preferably, the perfluoropentane is 0.01-0.5 parts by weight, preferably 0.02-0.2 parts by weight, more preferably 0.05-0.15 parts by weight, more preferably 0.08-0.12 parts by weight, most preferably 0.1 parts by weight.

Preferably, the weight ratio of the DPPC to the DSPE-PEG is 0.2-8:1, preferably 0.5-5:1, more preferably 1-2:1, more preferably 1.3-1.7:1, most preferably 1.5:1.

Preferably, the volume weight ratio (ml:mg) of the perfluoropentane to the DPPC is 1:20-40, preferably 1:25-35, more preferably 1:27-32, most preferably 1:30.

Preferably, the nanometer particle comprises drug-loaded nanometer particle.

Preferably, the nanometer particle comprises drug-loaded nanoparticle or drug-loaded liposome.

Preferably, the drug is 0.5-8 parts by weight, preferably 1-5 parts by weight, more preferably 1-3 parts by weight, most preferably 2 parts by weight.

Preferably, the weight ratio of the DPPC to the drug is 0.2-8:1, preferably 0.5-5:1, more preferably 1-2:1, more preferably 1.3-1.7:1, most preferably 1.5:1.

Preferably, the drug comprises a drug unstable in the lysosome of cell.

Preferably, the drug comprises a drug retained and/or degraded by the lysosome of cell.

Preferably, the degradation comprises lysosomal enzyme degradation.

Preferably, the drug comprises a drug degraded by the lysosomal enzyme.

Preferably, the action target of the drug is in the cytoplasm or nucleus.

Preferably, the drug comprises gene or protein.

Preferably, the gene is selected from the group consisting of DNA, RNA, and combinations thereof.

Preferably, the drug comprises anticancer drug.

Preferably, the anticancer drugs comprises chemical drug.

Preferably, the anticancer drug comprises gemcitabine, cytarabine, adriamycin, fluorouracil, and combinations thereof.

Preferably, the drug comprises free drug or prodrug.

Preferably, the drug comprises prodrug.

Preferably, the prodrug comprises the prodrug obtained by modifying the free drug on the prodrug carrier.

Preferably, the prodrug comprises the prodrug obtained by connecting the free drug with the prodrug carrier via chemical bonds.

Preferably, the drug comprises hydrophobic drug or hydrophilic drug.

Preferably, the free drug comprises hydrophobic drug or hydrophilic drug.

Preferably, the free drug comprises anticancer drug.

Preferably, the prodrug carrier comprises hydrophobic carrier or hydrophilic carrier.

Preferably, the prodrug carrier comprises higher fatty acid carrier or higher fatty alcohol carrier.

Preferably, the prodrug carrier comprises higher fatty acid containing 12-26 (preferably 14-22, more preferably 16-20) carbon atoms.

Preferably, the prodrug carrier comprises higher fatty alcohol containing 12-26 (preferably 14-22, more preferably 16-20) carbon atoms.

Preferably, the higher fatty acid carrier is selected from the group consisting of palmitic acid (hexadecanoic acid), margaric acid (heptadecanoic acid), stearic acid (octadecanoic acid), oleic acid (octadecenoic acid), linoleic acid (octadecadienoic acid), linolenic acid (octadecatrienoic acid), arachidic acid (eicosanoic acid), eicosapentaenoic acid, behenic acid (docosanoic acid), DHA (docosahexaenoic acid), lignoceric acid (tetracosanoic acid), and combinations thereof.

Preferably, the oleic acid comprises elaidic acid.

Preferably, the higher fatty alcohol carrier is selected from the group consisting of palmityl alcohol, stearyl alcohol, oleyl alcohol, linoleic alcohol, linolenic alcohol, arachidyl alcohol, eicosapentaenol, behenyl alcohol, docosahexaenol, and combinations thereof.

Preferably, the prodrug comprises amphiphilic prodrug.

Preferably, the amphiphilic prodrug is used as nanomaterial of the nanometer particle.

Preferably, the amphiphilic prodrug is used as nanomaterial of the nanoparticle.

Preferably, the amphiphilic prodrug is used as lipid material of the liposome.

Preferably, the amphiphilic prodrug is used as lipid bilayer.

Preferably, the amphiphilic prodrug comprises a drug active ingredient as hydrophilic part and the prodrug carrier as hydrophobic part; or the amphiphilic prodrug comprises a drug active ingredient as hydrophobic part and the prodrug carrier as hydrophilic part.

Preferably, the prodrug comprises:

D—C wherein, "D" is drug active ingredient, "C" is prodrug carrier, and "–" is connection bond.

Preferably, the drug active ingredient comprises a drug active ingredient unstable in the lysosome of cell.

Preferably, the drug active ingredient comprises hydrophobic drug active ingredient or hydrophilic drug active ingredient.

Preferably, the drug active ingredient comprises a drug active ingredient retained and/or degraded by the lysosome of cell.

Preferably, the degradation comprises lysosomal enzyme degradation.

Preferably, the drug active ingredient comprises a drug active ingredient degraded by the lysosomal enzyme.

Preferably, the action target of the drug active ingredient is in the cytoplasm or nucleus.

Preferably, the drug active ingredient comprises gene or protein.

Preferably, the gene is selected from the group consisting of DNA, RNA, and combinations thereof.

Preferably, the drug active ingredient comprises anticancer drug.

Preferably, the prodrug comprises:

(I)

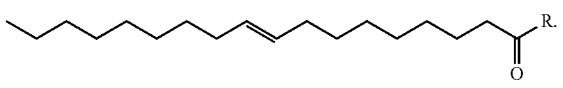

wherein, R is anticancer drug, the anticancer drug comprises gemcitabine, cytarabine, adriamycin, fluorouracil, and combinations thereof.

Preferably, the drug comprises gemcitabine elaidate.

Preferably, the prodrug comprises gemcitabine elaidate.

Preferably, the gemcitabine elaidate has the structure as follows:

(1) dissolving the nanomaterial in an organic solvent, and removing the organic solvent to obtain a nanometer particle film;

(2) immersing the perfluoropentane into the nanometer particle film, and hydrating the nanometer particle film with buffer solution, then stirring to obtain the nanometer particle.

Preferably, the nanometer particle is drug-loaded nanometer particle, the method for preparing the drug-loaded nanometer particle comprises the following steps:

(1) dissolving the nanomaterial and drug in an organic solvent, and removing the organic solvent to obtain a nanometer particle film;

(2) immersing the perfluoropentane into the nanometer particle film, and hydrating the nanometer particle film with buffer solution, then stirring to obtain the drug-loaded nanometer particle.

Preferably, the nanometer particle is liposome, the method for preparing the liposome comprises the following steps:

(1) dissolving the lipid material in an organic solvent, and removing the organic solvent to obtain a lipid film;

(2) immersing the perfluoropentane into the lipid film, and hydrating the lipid film with buffer solution, then stirring to obtain the liposome.

Preferably, the nanometer particle is drug-loaded liposome, the method for preparing the drug-loaded liposome comprises the following steps:

CP4126

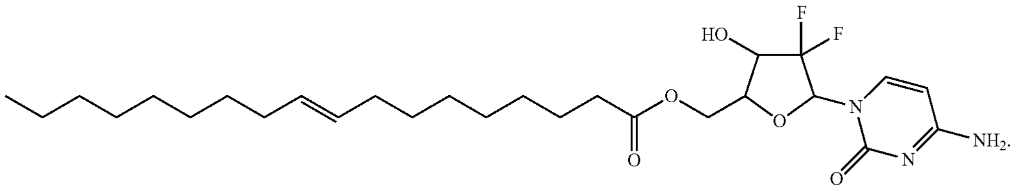

Preferably, the nanometer particle further comprises water, buffer solution and/or perfluoropentane.

Preferably, the nanometer particle encapsulates water, buffer solution and/or perfluoropentane.

Preferably, the lipid bilayer of the liposome encapsulates water, buffer solution and/or perfluoropentane.

Preferably, the buffer solution comprises glycerol-containing phosphate buffer saline.

Preferably, the volume fraction of the glycerol is 5-15%, preferably 8-12%, more preferably 10% in the glycerol-containing phosphate buffer saline.

Preferably, the concentration of the glycerol-containing phosphate buffer saline is 5-15 mM, preferably 8-12 mM, more preferably 10 mM, based on the concentration of phosphate radical.

Preferably, the pH of the glycerol-containing phosphate buffer saline is 7.2-7.6, preferably 7.4.

Preferably, the lipid bilayer encapsulates perfluoropentane and/or glycerol-containing phosphate buffer saline.

Preferably, the encapsulated rate of the drug-loaded nanometer particle is ≥90%, preferably ≥95%, more preferably ≥99%, most preferably 100%.

Preferably, the drug loading rate of the drug-loaded nanometer particle is 8-15 wt %, preferably 9-11 wt %.

In the second aspect of the present invention, it provides a method for preparing the nanometer particle according to the first aspect of the present invention, which comprises the following steps:

(1) dissolving the lipid material and drug in an organic solvent, and removing the organic solvent to obtain a lipid film;

(2) immersing the perfluoropentane into the lipid film, and hydrating the lipid film with buffer solution, then stirring to obtain the drug-loaded liposome.

Preferably, in the step (1), the organic solvent is selected from the group consisting of chloroform, dichloromethane, and combinations thereof.

Preferably, in the step (1), the weight volume ratio (mg:ml) of the DPPC to the organic solvent is 1:0.2-5, preferably 1:0.5-2, more preferably 1:0.5-1.5, more preferably 1:0.8-1.2, most preferably 1:1.

Preferably, in the step (2), the volume ratio of the perfluoropentane to the buffer solution is 1:30-70, preferably 1:40-60, more preferably 1:45-55, most preferably 1:48-52.

Preferably, in the step (1), the weight volume ratio (mg:ml) of the drug to the organic solvent is 1:2-5, preferably 1:1-2, more preferably 1:1.3-1.7, more preferably 1:1.5.

Preferably, in the step (1), the organic solvent is removed by rotary evaporation under reduced pressure.

Preferably, in the step (1), the organic solvent is removed by rotary evaporation under reduced pressure at 35-40° C.

Preferably, in the step (2), the perfluoropentane and the buffer solution are added sequentially to the lipid film to hydrate the lipid film.

Preferably, in the step (2), the perfluoropentane is immersed into the lipid film at a low temperature.

Preferably, in the step (2), the hydration is carried out at low temperature.

Preferably, in the step (2), the stirring comprises the following steps:

stirring at low temperature firstly, and then stirring at rising temperature.

Preferably, the low temperature is 2-10° C., preferably 2-6° C., most preferably 4° C.

Preferably, the stirring time under the low temperature is 0.2-0.8 h, preferably 0.4-0.6 h, more preferably 0.5 h.

Preferably, the rising temperature is 20-40° C., preferably 25-35° C., more preferably 28-32° C.

Preferably, the stirring time under the rising temperature is 0.5-1.5 h, preferably 0.8-1.2 h, more preferably 1 h.

Preferably, the stirring comprises stirring in the open container.

Preferably, the stirring can remove the unencapsulated perfluoropentane.

Preferably, the stirring comprises magnetic stirrer stirring.

Preferably, the stirring at rising temperature is performed in the open container.

Preferably, in the stirring at rising temperature, the container in which the stirring solution is placed is open.

Preferably, the stirring at rising temperature can remove the unencapsulated perfluoropentane.

Preferably, the liposome is in the form of liposome nanodroplet.

Preferably, the method for preparing the liposome comprises the following steps:

(i) dissolving the DPPC and DSPE-PEG in an organic solvent, and removing the organic solvent by rotary evaporation under reduced pressure to obtain a lipid film in round bottom flask;

(ii) cooling the lipid film to low temperature and adding perfluoropentane to immerse the lipid film, then adding buffer solution to hydrate, stirring for 0.2-0.8 h at 2-6° C., and then stirring for 0.8-1.2 h at 25-35° C. in the open round bottom flask to obtain the liposome.

Preferably, the method for preparing the liposome comprises the following steps:

(i) dissolving 2.8-3.2 mg of DPPC and 1.8-2.2 mg of DSPE-PEG in an organic solvent in round bottom flask, and removing the organic solvent by rotary evaporation under reduced pressure to obtain a lipid film in round bottom flask;

(ii) cooling the lipid film to 2-6° C. and adding 90-110 L of perfluoropentane to immerse the lipid film, then adding 4.5-5.5 ml of buffer solution to hydrate, stirring for 0.3-0.7 h at 2-6° C., and then stirring for 0.8-1.2 h at 28-32° C. in the open round bottom flask to obtain the liposome.

Preferably, the method for preparing the drug-loaded liposome comprises the following steps:

(i) dissolving the DPPC, DSPE-PEG and drug in an organic solvent, and removing the organic solvent by rotary evaporation under reduced pressure to obtain a lipid film in round bottom flask;

(ii) cooling the lipid film to low temperature and adding perfluoropentane to immerse the lipid film, then adding buffer solution to hydrate, stirring for 0.2-0.8 h at 2-6° C., and then stirring for 0.8-1.2 h at 25-35° C. in the open round bottom flask to obtain the drug-loaded liposome.

Preferably, the method for preparing the drug-loaded liposome comprises the following steps:

(i) dissolving 2.8-3.2 mg of DPPC, 1.2-1.8 mg of DSPE-PEG and 1.8-2.2 mg of drug in an organic solvent in round bottom flask, and removing the organic solvent by rotary evaporation under reduced pressure to obtain a lipid film in round bottom flask;

(ii) cooling the lipid film to 2-6° C. and adding 90-110 L of perfluoropentane to immerse the lipid film, then adding 4.5-5.5 ml of buffer solution to hydrate, stirring for 0.3-0.7 h at 2-6° C., and then stirring for 0.8-1.2 h at 28-32° C. in the open round bottom flask to obtain the drug-loaded liposome.

In the third aspect of the present invention, it provides a ligand-modified nanometer particle, ligand-modified nanometer particle comprises the nanometer particle according to the first aspect of the present invention; and a ligand.

Preferably, the ligand-modified nanometer particle comprises ligand-modified nanoparticle or ligand-modified liposome.

Preferably, the ligand comprises target ligand.

Preferably, the surface of the nanometer particle comprises the ligand.

Preferably, the surface comprises outer surface.

Preferably, the surface of the nanometer particle comprises outer surface of the nanometer particle.

Preferably, the outer surface of the nanometer particle comprises ligand.

Preferably, the ligand is modified on the nanometer particle.

Preferably, the ligand is modified on the nanomaterial of the nanometer particle.

Preferably, the ligand is modified on the surface of the nanometer particle.

Preferably, the modification comprises physical modification and/or chemical modification.

Preferably, the modification comprises physical adsorption, chemical adsorption and/or coupling.

Preferably, the ligand is adsorbed on the surface of the nanometer particle.

Preferably, the adsorption comprises physical adsorption and/or chemical adsorption.

Preferably, the ligand is coupled to the nanomaterial of the surface of the nanometer particle.

Preferably, the ligand comprises the ligand targeting cell receptor or cell surface receptor.

Preferably, the ligand comprises the ligand targeting tumor vascular cell and/or tumor cell.

Preferably, the ligand comprises peptide ligand or protein ligand.

Preferably, the ligand comprises RGD polypeptide and/or NGR polypeptide.

Preferably, the lipid material comprises ligand-modified lipid material.

Preferably, the ligand is coupled on the nanomaterial of the nanometer particle.

Preferably, the ligand is coupled to the lipid material.

Preferably, the coupling comprises chemical coupling.

Preferably, the ligand is coupled on the 1,2-distearoyl-sn-glycero-3-phosphoethanolamine-N-[methoxy (polyethylene glycol)] (DSPE-PEG) to form DSPE-PEG-ligand.

Preferably, the ligand is coupled on nanomaterial (e.g., lipid material).

Preferably, DSPE-PEG-ligand comprises DSPE-PEG-RGD and/or DSPE-PEG-NGR.

Preferably, the ligand coupled on the lipid material comprises DSPE-PEG-RGD and/or DSPE-PEG-NGR.

Preferably, the DSPE-PEG-RGD is selected from the group consisting of DSPE-PEG600-RGD, DSPE-PEG800-

RGD, DSPE-PEG1000-RGD, DSPE-PEG2000-RGD, DSPE-PEG4000-RGD, DSPE-PEG6000-RGD, and combinations thereof.

Preferably, the DSPE-PEG-NGR is selected from the group consisting of DSPE-PEG600-NGR, DSPE-PEG800-NGR, DSPE-PEG1000-NGR, DSPE-PEG2000-NGR, DSPE-PEG4000NGR, DSPE-PEG6000-NGR, and combinations thereof.

Preferably, the DSPE-PEG-ligand is 1-10 parts by weight, preferably 2-8 parts by weight, more preferably 4-6 parts by weight, most preferably 3 parts by weight.

Preferably, the weight ratio of the DSPE-PEG-ligand to the DPPC is 1:0.2-5, preferably 1:0.5-2, more preferably 1:0.5-1.5, more preferably 1:0.8-1.2, most preferably 1:1.

Preferably, the particle size of the ligand-modified nanometer particle is 120-260 nm, preferably 160-210 nm, more preferably 170-200 nm, most preferably 180-200 nm.

Preferably, the potential of the ligand-modified nanometer particle is −2 mV to −18 mV, preferably −2 mV to −15 mV, most preferably −5 mV to −12 mV.

Preferably, the ligand comprises the ligand targeting the cell surface receptor.

Preferably, the ligand comprises the ligand targeting the receptor on the surface of tumor vascular cell.

Preferably, the ligand comprises the ligand targeting the receptor on the surface of tumor cell.

Preferably, the surface comprises outer surface.

Preferably, the cell surface receptor comprises receptor on the surface of cell membrane.

Preferably, the cell surface receptor comprises receptor on the outer surface of cell membrane.

Preferably, the receptor comprises protein receptor, lipoprotein receptor or glycoprotein receptor.

Preferably, the ligand comprises ligand mediating uptake of the ligand-modified nanometer particle by cell.

Preferably, the ligand comprises ligand mediating endocytosis of the ligand-modified nanometer particle by cell.

Preferably, the ligand comprises ligand mediating endocytosis and exocytosis of the ligand-modified nanometer particle by cell.

Preferably, the ligand can mediate the penetration of the ligand-modified nanometer particle from tumor vessel into tumor site.

Preferably, the ligand can mediate the penetration of the ligand-modified nanometer particle from tumor vessel into tumor site via endocytosis and exocytosis.

Preferably, the ligand can target tumor vascular endothelial cell and mediate the endocytosis and exocytosis of the ligand-modified nanometer particle by tumor vascular endothelial cell.

Preferably, the ligand can mediate endocytosis of the ligand-modified nanometer particle in the blood by tumor vascular endothelial cell, then mediate exocytosis of the ligand-modified nanometer particle into extravascular of tumor (e.g., tumor tissue microenvironment).

In the fourth aspect of the present invention, it provides a method for preparing the ligand-modified nanometer particle according to the third aspect of the present invention, which comprises the following steps:

modifying the ligand on the nanometer particle to obtain the ligand-modified nanometer particle.

Preferably, the method for preparing the ligand-modified nanometer particle comprises the following steps:

(1) dissolving nanomaterial comprising the ligand-modified nanomaterial in an organic solvent, removing the organic solvent to obtain a nanometer particle film;

(2) immersing the perfluoropentane into the nanometer particle film, and hydrating the nanometer particle film with buffer solution, then stirring to obtain the ligand-modified nanometer particle.

Preferably, the method for preparing the ligand-modified nanometer particle comprises the following steps:

(1) dissolving the nanomaterial comprising the ligand-modified nanomaterial and drug in an organic solvent, removing the organic solvent to obtain a nanometer particle film;

(2) immersing the perfluoropentane into the nanometer particle film, and hydrating the nanometer particle film with buffer solution, then stirring to obtain the ligand-modified nanometer particle.

Preferably, the nanomaterial comprising the ligand-modified nanomaterial comprises one or more of DPPC, DSPE-PEG and DSPE-PEG ligand.

Preferably, the nanomaterial comprising the ligand-modified nanomaterial comprises one or more of DPPC, DSPE-PEG, DSPE-PEG-RGD and DSPE-PEG-NGR.

Preferably, the method for preparing the ligand-modified liposome comprises the following steps:

(i) dissolving the DPPC, DSPE-PEG-ligand and DSPE-PEG in an organic solvent, and removing the organic solvent by rotary evaporation under reduced pressure to obtain a lipid film in round bottom flask;

(ii) cooling the lipid film to low temperature and adding perfluoropentane to immerse the lipid film, then adding buffer solution to hydrate, stirring for 0.2-0.8 h at 2-6° C., and then stirring for 0.8-1.2 h at 25-35° C. in the open round bottom flask to obtain the ligand-modified liposome.

Preferably, the method for preparing the ligand-modified liposome comprises the following steps:

(i) dissolving 2.8-3.2 mg of DPPC, 2.8-3.2 mg of DSPE-PEG-ligand and 1.8-2.2 mg of DSPE-PEG in an organic solvent in round bottom flask, and removing the organic solvent by rotary evaporation under reduced pressure to obtain a lipid film in round bottom flask;

(ii) cooling the lipid film to 2-6° C. and adding 90-110 L of perfluoropentane to immerse the lipid film, then adding 4.5-5.5 ml of buffer solution to hydrate, stirring at 2-6° C., and then stirring at 28-32° C. in the open round bottom flask to obtain the ligand-modified liposome.

Preferably, the method for preparing the ligand-modified liposome comprises the following steps:

(i) dissolving the DPPC, DSPE-PEG-ligand, DSPE-PEG and drug in an organic solvent, and removing the organic solvent by rotary evaporation under reduced pressure to obtain a lipid film in round bottom flask;

(ii) cooling the lipid film to low temperature and adding perfluoropentane to immerse the lipid film, then adding buffer solution to hydrate, stirring for 0.2-0.8 h at 2-6° C., and then stirring for 0.8-1.2 h at 25-35° C. in the open round bottom flask to obtain the ligand-modified liposome.

Preferably, the method for preparing the ligand-modified liposome comprises the following steps:

(i) dissolving 2.8-3.2 mg of DPPC, 2.8-3.2 mg of DSPE-PEG-ligand, 1.8-2.2 mg of DSPE-PEG and 1.8-2.2 mg of drug in an organic solvent in round bottom flask, and removing the organic solvent by rotary evaporation under reduced pressure to obtain a lipid film in round bottom flask;

(ii) cooling the lipid film to 2-6° C. and adding 90-110 L of perfluoropentane to immerse the lipid film, then adding 4.5-5.5 ml of buffer solution to hydrate, stirring at 2-6° C., and then stirring at 28-32° C. in the open round bottom flask to obtain the ligand-modified liposome.

Preferably, the step (1) is according to the second aspect of the present invention.

Preferably, the step (2) is according to the second aspect of the present invention.

In the fifth aspect of the present invention, it provides a composition, the composition comprises the nanometer particle according to the first aspect of the present invention and/or the ligand-modified nanometer particle according to the third aspect of the present invention.

Preferably, the composition is a pharmaceutical composition.

Preferably, the pharmaceutical composition further comprises a pharmaceutically acceptable carrier.

Preferably, the composition is solid preparation, liquid preparation or semi-solid preparation.

Preferably, the composition is injection preparation, oral preparation or external preparation.

Preferably, the injection preparation is intravascular injection preparation.

Preferably, the injection preparation is intravenous injection preparation, arterial injection preparation, intratumoral injection preparation, tumor intravascular injection preparation or tumor microenvironment injection preparation.

In the sixth aspect of the present invention, it provides a use of the nanometer particle according to the first aspect of the present invention and/or the ligand-modified nanometer particle according to the third aspect of the present invention in the preparation of a composition for the prevention and/or treatment of disease.

Preferably, the nanometer particle is drug-loaded nanometer particle.

Preferably, the nanometer particle is drug-loaded nanoparticle or drug-loaded liposome.

Preferably, the disease is an indication disease of the drug Preferably, the drug comprises anticancer drug.

Preferably, the drug is according to the first aspect of the present invention.

Preferably, the disease comprises tumor.

Preferably, the tumor comprises human tumor or non-human mammal tumor.

Preferably, the tumor comprises lowly permeable tumor.

Preferably, the tumor comprises tumor with low permeability of tumor vessel.

Preferably, the tumor comprises solid tumor.

Preferably, the tumor comprises solid tumor with low permeability of tumor vessel.

Preferably, the tumor comprises liver cancer.

Preferably, the tumor comprises human liver cancer.

Preferably, the liver cancer cell comprises Huh7 cell and/or HepG2 cell.

Preferably, the tumor comprises pancreatic cancer.

Preferably, the pancreatic cancer comprises pancreatic adenocarcinoma.

Preferably, the pancreatic cancer comprises orthotropic pancreatic cancer.

Preferably, the pancreatic cancer comprises orthotropic pancreatic adenocarcinoma.

Preferably, the pancreatic cancer comprises pancreatic ductal adenocarcinoma.

Preferably, the pancreatic cancer comprises human pancreatic ductal adenocarcinoma.

Preferably, the pancreatic cancer cell comprises BxPC-3 cell.

Preferably, the tumor comprises tumor with poor Enhanced Permeability and Retention effect.

Preferably, the low permeability of tumor vessel comprises low permeability of drug from tumor vessel to tumor site.

Preferably, the low permeability of tumor vessel comprises low permeability of drug from tumor vessel cell gap to tumor site.

Preferably, the tumor vessel of the lowly permeable tumor comprises one or more features selected from the following groups:

(a) the tumor vascular cell is well organized and tightly stacked; and/or (b) the tumor vessel cell gap is small.

Preferably, the vascular cell comprises vascular endothelial cell.

Preferably, the composition is a pharmaceutical composition.

Preferably, the pharmaceutical composition further comprises a pharmaceutically acceptable carrier.

Preferably, the composition is solid preparation, liquid preparation or semi-solid preparation.

Preferably, the composition is injection preparation, oral preparation or external preparation.

Preferably, the injection preparation is intravascular injection preparation.

Preferably, the injection preparation is intravenous injection preparation, arterial injection preparation, intratumoral injection preparation, tumor intravascular injection preparation or tumor microenvironment injection preparation.

Preferably, the treatment comprises inhibition, alleviation, relief, reversal or eradication.

In the seventh of the present invention, it provides a system or device, the system or device comprises the nanometer particle according to the first aspect of the present invention and/or the ligand-modified nanometer particle according to the third aspect of the present invention; and an ultrasound instrument.

Preferably, the system or device further comprises a specification or label, the specification or label records that an ultrasound stimulation is carried out on the lesion site (e.g., tumor site) during the administration of the nanometer particle according to the first aspect of the present invention and/or the ligand-modified nanometer particle according to the third aspect of the present invention to a subject in need for the treatment of disease.

Preferably, the nanometer particle is drug-loaded nanometer particle.

Preferably, the nanometer particle is drug-loaded nanoparticle or drug-loaded liposome.

Preferably, the ultrasound instrument comprises ultrasonic device.

Preferably, the subject comprises human and non-human mammal.

Preferably, the non-human mammal comprises mice, rat, rabbit, monkey, bovine, horse, sheep, dog, cat, orangutan or baboon.

Preferably, the disease is an indication disease of the drug.

Preferably, the drug comprises anticancer drug.

Preferably, the drug is according to the first aspect of the present invention.

Preferably, the disease comprises tumor.

Preferably, the tumor is according to the sixth aspect of the present invention.

Preferably, the administration is injection administration, oral administration or external administration.

Preferably, the injection administration is intravenous injection administration, arterial injection administration, intratumoral injection administration, tumor intravascular injection administration or tumor microenvironment injection administration.

Preferably, the injection administration is intravascular injection administration.

In the eighth aspect of the present invention, it provides a method for preventing and/or treating disease, which comprises administering the nanometer particle according to the first aspect of the present invention and/or the ligand-modified nanometer particle according to the third aspect of the present invention to a subject in need, thereby preventing and/or treating disease.

Preferably, the nanometer particle is drug-loaded nanometer particle.

Preferably, the nanometer particle is drug-loaded nanoparticle or drug-loaded liposome.

Preferably, the subject comprises human and non-human mammal.

Preferably, the non-human mammal comprises mice, rat, rabbit, monkey, bovine, horse, sheep, dog, cat, orangutan or baboon.

Preferably, the disease is an indication disease of the drug.

Preferably, the disease comprises tumor.

Preferably, the drug comprises anticancer drug.

Preferably, the drug is according to the first aspect of the present invention.

Preferably, the tumor is according to the sixth aspect of the present invention.

Preferably, an ultrasound stimulation is carried out on the lesion site (e.g., tumor site) during the administration of the nanometer particle according to the first aspect of the present invention and/or the ligand-modified nanometer particle according to the third aspect of the present invention to a subject in need.

Preferably, the administration is injection administration, oral administration or external administration.

Preferably, the injection administration is intravenous injection administration, arterial injection administration, intratumoral injection administration, tumor intravascular injection administration or tumor microenvironment injection administration.

Preferably, the injection administration is intravascular injection administration.

In the ninth aspect of the present invention, it provides a protein corona modified nanometer particle, the protein corona modified nanometer particle comprises the nanometer particle according to the first aspect of the present invention and/or the ligand-modified nanometer particle according to the third aspect of the present invention; and a protein corona.

Preferably, the nanometer particle comprises perfluoropentane.

Preferably, the nanometer particle encapsulates perfluoropentane.

Preferably, the protein of the protein corona comprises serum protein, plasma protein and/or tissue protein.

Preferably, the serum protein, plasma protein and/or tissue protein comprise human or non-human mammalian serum protein, plasma protein and/or tissue protein.

Preferably, the serum protein, plasma protein and/or tissue protein comprise in vitro or isolated serum protein, plasma protein and/or tissue protein.

Preferably, the non-human mammal comprises mice, rat, rabbit, monkey, bovine, horse, sheep, dog, cat, orangutan or baboon.

Preferably, the bovine comprises fetal bovine.

Preferably, the serum and/or plasma comprises fetal bovine serum and/or fetal bovine plasma.

Preferably, the protein corona modified nanometer particle comprises in vitro or isolated protein corona modified nanometer particle.

Preferably, the protein corona is modified on the surface of the nanometer particle according to the first aspect of the present invention and/or the ligand-modified nanometer particle according to the third aspect of the present invention.

Preferably, the surface comprises outer surface.

Preferably, the modification comprises physical modification and/or chemical modification.

Preferably, the modification comprises physical adsorption, chemical adsorption and/or coupling.

Preferably, the modification comprises adsorption.

In the tenth aspect of the present invention, it provides a method for preparing the protein corona modified nanometer particle according to the ninth aspect of the present invention, which comprises the following steps:

incubating the nanometer particle according to the first aspect of the present invention and/or the ligand-modified nanometer particle according to the third aspect of the present invention with the protein to obtain the protein corona modified nanometer particle.

Preferably, the method is in vitro method or in vivo method.

Preferably, the method is non-diagnostic and non-therapeutic method.

Preferably, the incubating is in vitro or in vivo incubating.

Preferably, the incubating is performed in protein-containing condition.

Preferably, the protein-containing condition comprises blood, serum, plasma and/or culture medium.

Preferably, the incubating is performed in culture medium.

Preferably, the culture medium comprises liquid culture medium.

Preferably, the culture medium comprises cell culture medium.

Preferably, the culture medium comprises protein-containing medium.

Preferably, the culture medium comprises protein.

Preferably, the protein comprises serum protein, plasma protein and/or tissue protein.

Preferably, the culture medium comprises serum protein, plasma protein and/or tissue protein.

Preferably, the serum protein, plasma protein and/or tissue protein comprise in vitro or isolated serum protein, plasma protein and/or tissue protein.

Preferably, the culture medium comprises serum, plasma and/or tissue protein-containing culture medium.

Preferably, the culture medium comprises serum-containing culture medium.

Preferably, the serum comprises fetal bovine serum.

Preferably, the plasma comprises fetal bovine plasma.

Preferably, the volume fraction of the serum is 5-15%, preferably 8-12%, more preferably 10% in the serum-containing culture medium.

Preferably, the culture comprises in vitro culture.

Preferably, the serum, plasma and/or tissue protein comprises human or non-human mammalian serum, plasma and/or tissue proteins.

Preferably, the incubating is performed in the blood, serum or plasma.

Preferably, the blood, serum or plasma comprises in vitro or isolated blood, serum or plasma.

Preferably, the blood, serum or plasma comprises human or non-human mammalian blood, serum or plasma.

Preferably, the non-human mammal comprises mice, rat, rabbit, monkey, bovine, horse, sheep, dog, cat, orangutan or baboon.

Preferably, the bovine comprises fetal bovine.

Preferably, the incubating time is 0.25-6 h, preferably 0.25-4 h, more preferably 0.25-2 h, more preferably 0.25-1 h, more preferably 0.25-0.5 h, such as 0.5-1 h.

In the eleventh aspect of the present invention, it provides a method for removing protein corona of protein corona modified nanometer particle, the method comprises the following steps:

subjecting the protein corona modified nanometer particle to ultrasound stimulation to remove the protein corona of the protein corona modified nanometer particle.

Preferably, the nanometer particle comprises perfluoropentane.

Preferably, the nanometer particle encapsulates perfluoropentane.

Preferably, the method is in vitro method or in vivo method.

Preferably, the method comprises non-therapeutic and/or non-diagnostic method.

Preferably, the protein corona modified nanometer particle is according to the ninth aspect of the present invention.

Preferably, the removing comprises decreasing, reducing or eliminating.

Preferably, the decreasing comprises the decreasing of protein content.

Preferably, the decreasing protein corona comprises the decreasing of protein content in protein corona.

Preferably, the reducing comprises the reducing of protein content.

Preferably, the reducing protein corona comprises the reducing of protein content in protein corona.

Preferably, the subjecting is performed in protein-free condition.

Preferably, the subjecting comprises subjecting in protein-free condition.

Preferably, the protein corona modified nanometer particle comprises the protein corona modified nanometer particle in protein-free condition.

Preferably, the method comprises the following steps:

subjecting the protein corona modified nanometer particle to ultrasound stimulation to remove the protein corona of the protein corona modified nanometer particle in protein-free condition.

Preferably, the protein-free condition comprises physiological saline, PBS buffer solution or serum-free culture medium.

Preferably, the subjecting is performed in protein-containing condition.

Preferably, the subjecting comprises subjecting in protein-containing condition.

Preferably, the protein corona modified nanometer particle comprises the protein corona modified nanometer particle in protein-containing condition.

Preferably, the method comprises the following steps:

subjecting the protein corona modified nanometer particle to ultrasound stimulation to remove the protein corona of the protein corona modified nanometer particle in protein-containing condition.

Preferably, the protein-containing condition comprises blood, serum, plasma, and/or culture medium.

Preferably, the protein corona modified nanometer particle comprises protein corona modified nanometer particle in blood, serum or plasma.

Preferably, the blood, serum or plasma comprises in vitro or isolated blood, serum or plasma.

Preferably, the blood, serum or plasma comprises human or non-human mammal blood, serum or plasma.

Preferably, the protein corona modified nanometer particle comprises the protein corona modified nanometer particle in culture medium.

Preferably, the protein of the protein corona comprises serum protein, plasma protein and/or tissue protein.

Preferably, the serum protein, plasma protein and/or tissue protein comprise in vitro or isolated serum protein, plasma protein and/or tissue protein.

Preferably, the serum protein, plasma protein and/or tissue protein comprise the human or non-human mammal serum protein, plasma protein and/or tissue protein.

Preferably, the non-human mammal comprises mice, rat, rabbit, monkey, bovine, horse, sheep, dog, cat, orangutan or baboon Preferably, the bovine comprises fetal bovine.

Preferably, the serum comprises fetal bovine serum.

Preferably, the plasma comprises fetal bovine plasma.

Preferably, the culture medium comprises fluid culture medium.

Preferably, the culture medium comprises cell culture medium.

Preferably, the culture medium comprises protein-containing medium.

Preferably, the culture medium comprises protein.

Preferably, the protein comprises serum protein, plasma protein and/or tissue protein.

Preferably, the culture medium comprises serum protein, plasma protein and/or tissue protein.

Preferably, the culture medium comprises serum, plasma and/or tissue protein-containing culture medium.

Preferably, the culture medium comprises serum-containing culture medium.

Preferably, the volume fraction of the serum is 5-15%, preferably 8-12%, more preferably 10% in the serum-containing culture medium.

Preferably, the cell comprise tumor cell and/or tumor vascular cell.

Preferably, the tumor vascular cell comprises tumor vascular endothelial cell.

Preferably, the tumor vascular cell comprises ECDHCC cell.

Preferably, the cell comprises the cell that need to be cultured or grown in protein-containing condition.

Preferably, the cell comprises the cell that need to be cultured or grown in serum-containing medium.

Preferably, the cell comprises the cell that need to be cultured in serum-containing medium.

Preferably, the culture comprises in vitro culture.

Preferably, the acoustic intensity of the ultrasound stimulation is 0.1-40 $W/cm^2$, preferably 0.1-20 $W/cm^2$, more preferably 0.2-15 $W/cm^2$, more preferably 0.5-10 $W/cm^2$, more preferably 1-5 $W/cm^2$, more preferably 1-3 $W/cm^2$, more preferably 1.5-2.5 $W/cm^2$, more preferably 1.8-2.2 $W/cm^2$, most preferably 2.0 $W/cm^2$.

Preferably, the frequency of the ultrasound stimulation is 0.02-30 MHz, more preferably 0.1-20 MHz, more preferably 0.2-15 MHz, more preferably 0.5-10 MHz, more preferably 1-8 MHz, more preferably 1-5 MHz, more preferably 2-4

MHz, more preferably 2.5-3.5 MHz, more preferably 2.8-3.2 MHz, most preferably 3 MHz.

Preferably, the duty cycle of the ultrasound stimulation is 10-80%, more preferably 20-80%, more preferably 30-70%, more preferably 35-65%, more preferably 40-60%, more preferably 45-55%, more preferably 48-52%, most preferably 50%.

Preferably, the time of the ultrasound stimulation is ≥2 min, more preferably ≥5 min, preferably ≥10 min, more preferably ≥15 min, more preferably ≥20 min, such as 15-30 min.

In the twelfth aspect of the present invention, it provides a method for screening or identifying potential ligand targeting cell or cell surface receptor, the method comprises the following steps:

(I) modifying the ligand on the nanometer particle to obtain ligand-modified nanometer particle;

(II) incubating the cell or cell surface receptor with the ligand-modified nanometer particle in the step (I) and then conducting ultrasound stimulation, and determining the binding of the ligand-modified nanometer particle in step (I) or the ligand of the ligand-modified nanometer particle in the step (I) to the cell or cell surface receptor, thereby screening or identifying whether the ligand in the step (I) is potential ligand targeting the cell or cell surface receptor.

Preferably, the cell surface receptor comprises receptor on the surface of cell membrane.

Preferably, the cell surface receptor comprises receptor on the outer surface of cell membrane.

Preferably, the nanometer particle comprises perfluoropentane.

Preferably, the nanometer particle encapsulates perfluoropentane.

Preferably, the nanometer particle is according to the first aspect of the present invention.

Preferably, the ligand-modified nanometer particle in the step (I) is according to the third aspect of the present invention.

Preferably, the ligand in the step (I) comprises ligand to be tested.

Preferably, the step (II) comprises:

(II) incubating the cell or cell surface receptor with the ligand-modified nanometer particle in the step (I) and then conducting ultrasound stimulation, and determining whether the ligand-modified nanometer particle in step (I) or the ligand of the ligand-modified nanometer particle in the step (I) binds to the cell or cell surface receptor, thereby screening or identifying whether the ligand in the step (I) is potential ligand targeting the cell or cell surface receptor.

Preferably, in the step (II), if the ligand-modified nanometer particle in step (I) or the ligand of the ligand-modified nanometer particle in step (I) binds to the cell or cell surface receptor, the ligand in the step (I) is potential ligand targeting the cell or cell surface receptor.

Preferably, in the step (II), if the ligand-modified nanometer particle in step (I) or the ligand of the ligand-modified nanometer particle in step (I) does not bind to the cell or cell surface receptor, the ligand in the step (I) is not potential ligand targeting the cell or cell surface receptor.

Preferably, the method further comprises setting a control group, the control group comprises a nanometer particle without ligand modification, and determining the binding of the nanometer particle without ligand modification to the cell or cell surface receptor.

Preferably, the method further comprises setting a control group, the control group comprises a nanometer particle without ligand modification and the other conditions are the same to those of the ligand-modified nanometer particle, and determining the binding of the nanometer particle without ligand modification to the cell or cell surface receptor.

Preferably, if the binding force B1 of the ligand-modified nanometer particle or the ligand of the ligand-modified nanometer particle to the cell or cell surface receptor is greater than the binding force B0 of the nanometer particle without ligand modification to the cell or cell surface receptor, the ligand in the step (I) is potential ligand targeting the cell or cell surface receptor.

Preferably, the step (II) comprises:

(II-1) in the test group, incubating the cell or cell surface receptor with the ligand-modified nanometer particle in the step (I) and then conducting ultrasound stimulation, and determining the binding force B1 of the ligand-modified nanometer particle in step (I) or the ligand of the ligand-modified nanometer particle in the step (I) to the cell or cell surface receptor; and setting a control group, the control group comprises a nanometer particle without ligand modification and the other conditions are the same to those of the test group, and determining the binding force B0 of the nanometer particle without ligand modification to the cell or cell surface receptor;

(II-2) if the binding force B1 of the ligand-modified nanometer particle in the step (I) or the ligand of the ligand-modified nanometer particle in the step (I) to the cell or cell surface receptor is greater than the binding force B0 of the nanometer particle without ligand modification to the cell or cell surface receptor, the ligand in the step (I) is potential ligand targeting the cell or cell surface receptor.

Preferably, if the binding force B1 of the ligand-modified nanometer particle in the step (I) or the ligand of the ligand-modified nanometer particle in the step (I) to the cell or cell surface receptor is similar to the binding force B0 of the nanometer particle without ligand modification to the cell or cell surface receptor, the ligand in the step (I) is not potential ligand targeting the cell or cell surface receptor.

Preferably, the targeting comprises specific targeting or non-specific targeting.

Preferably, the "greater than" comprises significantly greater than.

Preferably, the "greater than" comprises significantly greater than with statistically significant.

Preferably, "greater than" means the ratio (B1/B0) of the binding force B1 of the ligand-modified nanometer particle or the ligand of the ligand-modified nanometer particle to the cell or cell surface receptor to the binding force B0 of the nanometer particle without ligand modification to the cell or cell surface receptor is ≥1.0, preferably ≥1.2, more preferably ≥1.5, more preferably ≥2, more preferably ≥3, more preferably ≥5, more preferably ≥10, more preferably ≥15, more preferably ≥20, more preferably ≥30, more preferably ≥50, more preferably ≥80, more preferably ≥100, more preferably ≥150, more preferably ≥200, more preferably ≥500, more preferably ≥1000, more preferably ≥5000, more preferably ≥10000.

Preferably, the B1/B0 is 1.5-10,000, preferably 2-500, more preferably 2-200, more preferably 2-100, more preferably 2-50, more preferably 5-30.

Preferably, the "greater than" means that the binding force B1 of the ligand-modified nanometer particle or the ligand of the ligand-modified nanometer particle to the cell or cell surface receptor in the test group with biological replicates is greater than the binding force B0 of the nanometer particle without ligand modification to the cell or cell surface receptor in the control group with biological replicates, and the p value is $<0.05$ in t test.

Preferably, the ligand comprises peptide ligand or protein ligand.

Preferably, the receptor comprise protein receptor, lipoprotein receptor or glycoprotein receptor.

Preferably, the binding comprises affinity.

Preferably, the binding force comprises affinity force.

Preferably, the ligand comprises potential ligand.

Preferably, the ligand-modified nanometer particle comprise in vitro or isolated ligand-modified nanometer particle.

Preferably, the cell or cell surface receptor comprises in vitro or isolated cell or cell surface receptor.

Preferably, the method comprises in vitro method or in vivo method.

Preferably, the method comprises non-therapeutic and/or non-diagnostic method.

Preferably, the incubating comprises in vitro or in vivo incubating.

Preferably, the in vivo comprises in vivo in human or non-human mammal.

Preferably, the incubating comprises incubating in protein-containing condition.

Preferably, the incubating is performed in protein-containing condition.

Preferably, in the step (II), the incubating comprises incubating in protein-containing condition.

Preferably, in the step (II), the incubating is performed in protein-containing condition.

Preferably, the incubating comprises incubating the cell or cell surface receptor with the ligand-modified nanometer particle in the step (I) in protein-containing condition.

Preferably, the step (II) comprises:

incubating the cell or cell surface receptor with the ligand-modified nanometer particle in the step (I) in protein-containing condition and then conducting ultrasound stimulation, and determining the binding of the ligand-modified nanometer particle in step (I) or the ligand of the ligand-modified nanometer particle in the step (I) to the cell or cell surface receptor, thereby screening or identifying whether the ligand in the step (I) is potential ligand targeting the cell or cell surface receptor.

Preferably, the condition comprises in vivo condition or in vitro condition.

Preferably, the cell comprises the cell that need to be cultured or grown in protein-containing condition.

Preferably, the cell comprises the cell that need to be cultured or grown in serum-containing medium.

Preferably, the cell comprises the cell that need to be cultured in serum-containing medium.

Preferably, the culture comprises in vitro culture.

Preferably, the protein-containing condition comprises blood, serum, plasma, tissue microenvironment and/or culture medium.

Preferably, the blood, serum or plasma comprises in vitro or isolated blood, serum or plasma.

Preferably, the blood, serum or plasma comprises human or non-human mammalian blood, serum or plasma.

Preferably, the protein comprises serum protein, plasma protein and/or tissue protein.

Preferably, the serum protein, plasma protein and/or tissue protein comprise in vitro or isolated serum protein, plasma protein and/or tissue protein.

Preferably, the serum protein, plasma protein and/or tissue protein comprise human or non-human mammalian serum protein, plasma protein and/or tissue protein.

Preferably, the non-human mammal comprises mice, rat, rabbit, monkey, bovine, horse, sheep, dog, cat, orangutan or baboon.

Preferably, the bovine comprises fetal bovine.

Preferably, the serum comprises fetal bovine serum.

Preferably, the plasma comprises fetal bovine plasma.

Preferably, the culture medium comprises fluid culture medium.

Preferably, the culture medium comprises cell culture medium.

Preferably, the culture medium comprises protein-containing medium.

Preferably, the culture medium comprises protein.

Preferably, the culture medium comprises serum protein, plasma protein and/or tissue protein.

Preferably, the culture medium comprises serum, plasma and/or tissue protein-containing culture medium.

Preferably, the culture medium comprises serum-containing culture medium.

Preferably, the volume fraction of the serum is 5-15%, preferably 8-12%, more preferably 10% in the serum-containing culture medium.

Preferably, the incubating comprises incubating the cell or cell surface receptor with the ligand-modified nanometer particle in the step (I) in serum, plasma and/or tissue protein-containing culture medium.

Preferably, the incubating comprises incubating the cell or cell surface receptor with the ligand-modified nanometer particle in the step (I) in serum-containing culture medium Preferably, the ligand comprises ligand targeting cell or cell surface receptor.

Preferably, the cell comprise tumor cell and/or tumor vascular cell.

Preferably, the tumor vascular cell comprises tumor vascular endothelial cell.

Preferably, the tumor comprises human tumor or non-human mammalian tumor.

Preferably, the tumor comprises lowly permeable tumor.

Preferably, the tumor comprises tumor with low permeability of tumor vessel.

Preferably, the tumor comprises solid tumor.

Preferably, the tumor comprises solid tumor with low permeability of tumor vessel.

Preferably, the tumor comprises liver cancer.

Preferably, the tumor comprises human liver cancer.

Preferably, the liver cancer cell comprises Huh7 cell and/or HepG2 cell.

Preferably, the tumor comprises pancreatic cancer.

Preferably, the pancreatic cancer comprises pancreatic adenocarcinoma.

Preferably, the pancreatic cancer comprises orthotropic pancreatic cancer.

Preferably, the pancreatic cancer comprises orthotropic pancreatic adenocarcinoma.

Preferably, the pancreatic cancer comprises pancreatic ductal adenocarcinoma.

Preferably, the pancreatic cancer comprises human pancreatic ductal adenocarcinoma.

Preferably, the pancreatic cancer cell comprises BxPC-3 cell.

Preferably, the tumor vascular cell comprises ECDHCC cell.

Preferably, the tumor comprises tumor with poor Enhanced Permeability and Retention effect.

Preferably, the low permeability of tumor vessel comprises low permeability of drug from tumor vessel to tumor site.

Preferably, the low permeability of tumor vessel comprises low permeability of drug from tumor vessel cell gap to tumor site.

Preferably, the tumor vessel of the lowly permeable tumor comprises one or more features selected from the following groups:

(a) the tumor vascular cell is well organized and tightly stacked; and/or (b) the tumor vessel cell gap is small.

Preferably, the vascular cell comprises vascular endothelial cell.

Preferably, the binding comprises specific binding or non-specific binding.

Preferably, the receptor comprises receptor on the outer surface of cell membrane.

Preferably, the binding is measured by isotope disappearance assay, fluorescein assay, flow cytometry assay and/or transwell migration assay.

Preferably, the nanometer particle and/or the ligand is labeled with isotopes and/or fluorescein.

Preferably, the fluorescein comprises FITC (Fluorescein isothiocyanate), Cyanine 5 (Cy5), and/or Cyanine 5.5 (Cy5.5).

Preferably, the binding mediates the uptake of the ligand-modified nanometer particle by the cell.

Preferably, the binding mediates the endocytosis of the ligand-modified nanometer particle by the cell.

Preferably, the binding mediates the endocytosis and exocytosis of the ligand-modified nanometer particle by the cell.

Preferably, the binding is measured by determining the uptake efficiency of the ligand-modified nanometer particle in the step (I) by the cell.

Preferably, the cell does not have ability to uptake the nanometer particle without ligand modification in the control group.

Preferably, the screening or identifying whether the ligand in the step (I) is potential ligand targeting the cell or cell surface receptor comprises:

if the uptake efficiency of the ligand-modified nanometer particle in the step (I) by the cell is greater than the uptake efficiency of the nanometer particle without ligand modification in the control group by the cell, the ligand in the step (I) is potential ligand targeting the cell or cell surface receptor.

Preferably, the binding is measured by determining the endocytosis ability of the ligand-modified nanometer particle in the step (I) by the cell.

Preferably, the cell does not have endocytosis ability of the nanometer particle without ligand modification in the control group.

Preferably, the screening or identifying whether the ligand in the step (I) is potential ligand targeting the cell or cell surface receptor comprises:

if the endocytosis ability of the ligand-modified nanometer particle in the step (I) by the cell is greater than the endocytosis ability of the nanometer particle without ligand modification in the control group by the cell, the ligand in the step (I) is potential ligand targeting the cell or cell surface receptor.

Preferably, the binding is measured by determining the endocytosis and exocytosis ability of the ligand-modified nanometer particle in the step (I) by the cell.

Preferably, the cell does not have endocytosis and exocytosis ability of the nanometer particle without ligand modification in the control group.

Preferably, the screening or identifying whether the ligand in the step (I) is potential ligand targeting the cell or cell surface receptor comprises:

if the endocytosis and exocytosis ability of the ligand-modified nanometer particle in the step (I) by the cell is greater than the endocytosis and exocytosis ability of the nanometer particle without ligand modification in the control group by the cell, the ligand in the step (I) is potential ligand targeting the cell or cell surface receptor.

Preferably, the ligand in the step (I) comprises ligand mediating endocytosis of the ligand-modified nanometer particle by the cell.

Preferably, the ligand can mediate endocytosis of the ligand-modified nanometer particle by cell after the ligand-modified nanometer particle or the ligand of the ligand-modified nanometer particle binds to the cell or cell surface receptor.

Preferably, the screening or identifying whether the ligand in the step (I) is potential ligand targeting the cell or cell surface receptor comprises:

if the ligand can mediate endocytosis of the ligand-modified nanometer particle by cell after the ligand-modified nanometer particle or the ligand of the ligand-modified nanometer particle binds to the cell or cell surface receptor, the ligand in the step (I) is potential ligand targeting the cell or cell surface receptor.

Preferably, the ligand in the step (I) comprises ligand mediating endocytosis and exocytosis of the ligand-modified nanometer particle by the cell.

Preferably, the ligand can mediate endocytosis and exocytosis of the ligand-modified nanometer particle by cell after the ligand-modified nanometer particle or the ligand of the ligand-modified nanometer particle binds to the cell or cell surface receptor.

Preferably, the screening or identifying whether the ligand in the step (I) is potential ligand targeting the cell or cell surface receptor comprises:

if the ligand can mediate endocytosis and exocytosis of the ligand-modified nanometer particle by cell after the ligand-modified nanometer particle or the ligand of the ligand-modified nanometer particle binds to the cell or cell surface receptor, the ligand in the step (I) is potential ligand targeting the cell or cell surface receptor.

Preferably, the ligand can mediate endocytosis of the ligand-modified nanometer particle in the blood by tumor vascular cell after the ligand-modified nanometer particle or the ligand of the ligand-modified nanometer particle binds to the tumor vascular cell or tumor vascular cell surface receptor, then the ligand-modified nanometer particle is exocytosed to extravascular of tumor (e.g., tumor tissue microenvironment).

Preferably, the screening or identifying whether the ligand in the step (I) is potential ligand targeting the cell or cell surface receptor comprises:

if the ligand can mediate endocytosis of the ligand-modified nanometer particle in the blood by tumor vascular cell after the ligand-modified nanometer particle or the ligand of the ligand-modified nanometer particle binds to the tumor vascular cell or tumor vascular cell surface receptor, then the ligand-modified nanometer particle is exocytosed to extravascular of tumor (e.g., tumor tissue microenvironment), the ligand in the step (I) is potential ligand targeting the cell or cell surface receptor.

Preferably, the method for measuring the binding or binding force of the ligand-modified nanometer particle or the ligand of the ligand-modified nanometer particle in the step (I) to the cell or cell surface receptor comprises:

if tumor vascular cell can endocytose the ligand-modified nanometer particle in the blood, then the ligand-modified nanometer particle is exocytosed to extravascular of tumor (e.g., tumor tissue microenvironment), the ligand can bind to cell or cell surface receptor.

Preferably, the tumor vascular cell cannot endocytose the nanometer particle without ligand modification in the blood circulation.

Preferably, the ligand comprises ligand targeting receptor on the surface of tumor vascular cell.

Preferably, the ligand comprises the ligand targeting the receptor on the surface of tumor cell.

Preferably, the surface comprises outer surface.

Preferably, the ligand can mediate the penetration of the ligand-modified nanometer particle from tumor vessel into tumor site.

Preferably, the ligand can mediate the penetration of the ligand-modified nanometer particle from tumor vessel into tumor site via endocytosis and exocytosis.

Preferably, the ligand can target tumor vascular endothelial cell and mediate the endocytosis and exocytosis of the ligand-modified nanometer particle by tumor vascular endothelial cell.

Preferably, the ligand comprises ligand mediating uptake of the ligand-modified nanometer particle by cell.

Preferably, the ligand comprises ligand mediating endocytosis of the ligand-modified nanometer particle by cell.

Preferably, the ligand comprises ligand mediating endocytosis and exocytosis of the ligand-modified nanometer particle by cell.

Preferably, the ligand can mediate endocytosis of the ligand-modified nanometer particle in the blood by tumor vascular cell, then mediate exocytosis of the ligand-modified nanometer particle into extravascular of tumor (e.g., tumor tissue microenvironment).

Preferably, the incubated mixture of the cell or cell surface receptor and the ligand-modified nanometer particle is conducted ultrasound stimulation.

Preferably, the acoustic intensity of the ultrasound stimulation is 0.1-40 $W/cm^2$, preferably 0.1-20 $W/cm^2$, more preferably 0.2-15 $W/cm^2$, more preferably 0.5-10 $W/cm^2$, more preferably 1-5 $W/cm^2$, more preferably 1-3 $W/cm^2$, more preferably 1.5-2.5 $W/cm^2$, more preferably 1.8-2.2 $W/cm^2$, most preferably 2.0 $W/cm^2$.

Preferably, the frequency of the ultrasound stimulation is 0.02-30 MHz, more preferably 0.1-20 MHz, more preferably 0.2-15 MHz, more preferably 0.5-10 MHz, more preferably 1-8 MHz, more preferably 1-5 MHz, more preferably 2-4 MHz, more preferably 2.5-3.5 MHz, more preferably 2.8-3.2 MHz, most preferably 3 MHz.

Preferably, the duty cycle of the ultrasound stimulation is 10-80%, more preferably 20-80%, more preferably 30-70%, more preferably 35-65%, more preferably 40-60%, more preferably 45-55%, more preferably 48-52%, most preferably 50%.

In the thirteenth aspect of the present invention, it provides a use of the nanometer particle according to the first aspect of the present invention in the preparation of a carrier for screening or identifying potential ligand targeting cell or cell surface receptor.

Preferably, the method for screening or identifying potential ligand targeting cell or cell surface receptor comprises:

(I) modifying the ligand on the nanometer particle to obtain ligand-modified nanometer particle;

(II) incubating the cell or cell surface receptor with the ligand-modified nanometer particle in the step (I) and then conducting ultrasound stimulation, and determining the binding of the ligand-modified nanometer particle in step (I) or the ligand of the ligand-modified nanometer particle in the step (I) to the cell or cell surface receptor, thereby screening or identifying whether the ligand in the step (I) is potential ligand targeting the cell or cell surface receptor.

Preferably, the cell surface receptor comprises receptor on the surface of cell membrane.

Preferably, the cell surface receptor comprises receptor on the outer surface of cell membrane.

Preferably, the receptor comprises protein receptor, lipoprotein receptor or glycoprotein receptor.

Preferably, the method for screening or identifying potential ligand targeting cell or cell surface receptor is according to the twelfth aspect of the present invention.

In the fourteenth aspect of the present invention, it provides a method for inhibiting cell, the method comprises:

incubating the cell with the nanometer particle according to the first aspect of the present invention and/or the ligand-modified nanometer particle according to the third aspect of the present invention and then conducting ultrasound stimulation to inhibit the cell.

Preferably, the method is in vitro method or in vivo method.

Preferably, the nanometer particle comprises drug-loaded nanometer particle.

Preferably, the method comprises a method for enhancing the ligand-modified nanometer particle to inhibit cell.

Preferably, the method is non-diagnostic and non-therapeutic method.

Preferably, the ligand comprises ligand targeting cell or cell surface receptor.

Preferably, the ligand comprises ligand mediating uptake of the ligand-modified nanometer particle by cell.

Preferably, the ligand comprises ligand mediating endocytosis of the ligand-modified nanometer particle by cell.

Preferably, the ligand comprises RGD peptide and/or an NGR peptide.

Preferably, the cell comprise tumor cell and/or tumor vascular cell.

Preferably, the tumor vascular cell comprises tumor vascular endothelial cell.

Preferably, the tumor vascular cell comprises ECDHCC cell.

Preferably, the drug comprises cell inhibitor.

Preferably, the drug comprises anti-tumor drug.

Preferably, the drug is according to the first aspect of the present invention.

Preferably, the tumor is according to the sixth aspect of the present invention.

Preferably, the incubating is performed in protein-containing condition.

Preferably, the incubating comprises incubating in protein-containing condition.

Preferably, the method comprises:

incubating the cell with the nanometer particle according to the first aspect of the present invention and/or the ligand-modified nanometer particle according to the third aspect of the present invention in protein-containing condition and then conducting ultrasound stimulation to inhibit the cell.

Preferably, the cell comprises the cell that need to be cultured or grown in protein-containing condition.

Preferably, the cell comprises the cell that need to be cultured or grown in serum-containing medium.

Preferably, the cell comprises the cell that need to be cultured in serum-containing medium.

Preferably, the protein-containing condition comprises blood, serum, plasma and/or culture medium.

Preferably, the blood, serum or plasma comprise in vitro or isolated blood, serum or plasma.

Preferably, the blood, serum or plasma comprises human or non-human mammalian blood, serum or plasma.

Preferably, the non-human mammal comprises mice, rat, rabbit, monkey, bovine, horse, sheep, dog, cat, orangutan or baboon.

Preferably, the bovine comprises fetal bovine.

Preferably, the protein-containing condition is according to the twelfth aspect of the present invention.

Preferably, the culture medium comprises fluid culture medium.

Preferably, the culture medium comprises cell culture medium.

Preferably, the culture medium comprises protein-containing medium.

Preferably, the culture medium comprises protein.

Preferably, the protein comprises serum protein, plasma protein and/or tissue protein.

Preferably, the serum protein, plasma protein and/or tissue protein comprise in vitro or isolated serum protein, plasma protein and/or tissue protein.

Preferably, the serum protein, plasma protein and/or tissue protein comprise human or non-human mammalian serum protein, plasma protein and/or tissue protein.

Preferably, the culture medium comprises serum, plasma and/or tissue protein-containing culture medium.

Preferably, the culture medium comprises serum-containing culture medium.

Preferably, the volume fraction of the serum is 5-15%, preferably 8-12%, more preferably 10% in the serum-containing culture medium.

Preferably, the serum comprises fetal bovine serum.

Preferably, the plasma comprises fetal bovine plasma.

Preferably, the incubating comprises in vitro incubating.

Preferably, the culture comprises in vitro culture.

Preferably, the surface of the nanometer particle comprises protein corona in the culture medium under no ultrasound stimulation treatment.

Preferably, the protein corona is adsorbed on the surface of the nanometer particle.

Preferably, the ligand can mediate the uptake of the ligand modified nanometer particle by cell after binding to cell or cell surface receptor.

Preferably, the ligand can mediate the endocytosis of the ligand modified nanometer particle by cell after binding to cell or cell surface receptor.

Preferably, the ligand can bind to the the cell or cell surface receptor.

Preferably, the binding of the ligand to the cell or cell surface receptor can mediate the uptake of the ligand-modified nanometer particle by the cell.

Preferably, the binding of the ligand to the cell or cell surface receptor can mediate the endocytosis of the ligand-modified nanometer particle by the cell.

Preferably, the cell surface receptor comprises receptor on the surface of cell membrane.

Preferably, the cell surface receptor comprises receptor on the outer surface of cell membrane.

Preferably, the receptor comprises protein receptor, lipoprotein receptor or glycoprotein receptor.

Preferably, the incubated mixture of the cell and the nanometer particle or the ligand-modified nanometer particle is conducted ultrasound stimulation.

In the fifteenth aspect of the present invention, a use of ultrasound instrument for preparing an apparatus, the apparatus is used for:

(a) removing protein corona of the protein corona modified nanometer particle by ultrasound stimulation;

(b) screening or identifying potential ligand targeting cell or cell surface receptor;

(c) enhancing the ligand-modified nanometer particle to treat disease by performing an ultrasound stimulation on the lesion site (e.g., tumor site); and/or (d) improving the lysosome retention and/or degradation of nanometer particle, ligand-modified nanometer particle and/or protein corona modified nanometer particle by ultrasound stimulation.

Preferably, the nanometer particle comprises perfluoropentane.

Preferably, the nanometer particle encapsulates perfluoropentane.

Preferably, the nanometer particle is according to the first aspect of the present invention.

Preferably, the ligand-modified nanometer particle is according to the third aspect of the present invention.

Preferably, the protein corona modified nanometer particle is according to the ninth aspect of the present invention.

Preferably, the method for removing protein corona of the protein corona modified nanometer particle is according to the eleventh aspect of the present invention.

Preferably, the (a) comprises removing protein corona of the protein corona modified nanometer particle by ultrasound stimulation to improve the efficacy of the nanometer particle.

Preferably, the (a) removing protein corona of the protein corona modified nanometer particle by ultrasound stimulation comprises:

subjecting the protein corona modified nanometer particle to ultrasound stimulation to remove the protein corona of the protein corona modified nanometer particle.

Preferably, the method for screening or identifying potential ligand targeting cell or cell surface receptor is according to the twelfth aspect of the present invention.

Preferably, the cell surface receptor comprises receptor on the surface of cell membrane.

Preferably, the cell surface receptor comprises receptor on the outer surface of cell membrane.

Preferably, the receptor comprises protein receptor, lipoprotein receptor or glycoprotein receptor.

Preferably, the (d) improving the lysosome retention and/or degradation of nanometer particle, ligand-modified nanometer particle and/or protein corona modified nanometer particle by ultrasound stimulation comprises:

incubating the cell with the nanometer particle, ligand-modified nanometer particle and/or protein corona modified nanometer particle and then conducting ultrasound stimulation to improve the lysosome retention and/or degradation of nanometer particle, ligand-modified nanometer particle and/or protein corona modified nanometer particle.

Preferably, the method is in vitro method or in vivo method.

Preferably, the method is non-diagnostic and non-therapeutic method.

Preferably, the incubating is in vivo incubating or in vitro incubating.

Preferably, the incubating comprises incubating in protein-containing condition.

Preferably, the incubating comprises incubating in serum-containing medium.

Preferably, the incubating is according to the twelfth aspect of the present invention.

Preferably, the cell comprises the cell that need to be cultured or grown in protein-containing condition.

Preferably, the cell comprises the cell that need to be cultured or grown in serum-containing medium.

Preferably, the cell comprises the cell that need to be cultured in serum-containing medium.

Preferably, the protein-containing condition is according to the twelfth aspect of the present invention.

Preferably, the nanometer particle comprises drug-loaded nanometer particle.

Preferably, the drug is according to the first aspect of the present invention.

Preferably, the disease is an indication disease of the drug.

Preferably, the cell comprise tumor cell and/or tumor vascular cell.

Preferably, the tumor vascular cell comprise tumor vascular endothelial cell.

Preferably, the tumor vascular cell comprises ECDHCC cell.

Preferably, the disease comprises tumor.

Preferably, the tumor is as described in a sixth aspect of the present invention.

Preferably, the administration is injection administration, oral administration or external administration.

Preferably, the injection administration is intravenous injection administration, arterial injection administration, intratumoral injection administration, tumor intravascular injection administration or tumor microenvironment injection administration.

Preferably, the injection administration is intravascular injection administration.

Preferably, the improving comprises avoiding or overcoming.

Preferably, the degradation comprises degradation by lysosomal enzyme.

In the sixteenth aspect of the present invention, a use of the system or device according to the seventh aspect of the present invention for preparing an apparatus, the apparatus is used for to treating disease.

Preferably, the apparatus further comprises a specification or label, the specification or label records that an ultrasound stimulation is carried out on the lesion site (e.g., tumor site) during the administration of the nanometer particle according to the first aspect of the present invention and/or the ligand-modified nanometer particle according to the third aspect of the present invention to a subject in need for the treatment of disease.

Preferably, the nanometer particle is drug-loaded nanometer particle.

Preferably, the nanometer particle is drug-loaded nanoparticle or drug-loaded liposome.

Preferably, the subject comprises human and non-human mammal.

Preferably, the non-human mammal comprises mice, rat, rabbit, monkey, bovine, horse, sheep, dog, cat, orangutan or baboon.

Preferably, the disease is an indication disease of the drug.

Preferably, the drug comprises anticancer drug.

Preferably, the drug is according to the first aspect of the present invention.

Preferably, the disease comprises tumor.

Preferably, the tumor is according to the sixth aspect of the present invention.

Preferably, the administration is injection administration, oral administration or external administration.

Preferably, the injection administration is intravenous injection administration, arterial injection administration, intratumoral injection administration, tumor intravascular injection administration or tumor microenvironment injection administration.

Preferably, the injection administration is intravascular injection administration.

It should be understood that, in the present invention, each of the technical features specifically described above and below (e.g., those in the Examples) can be combined with each other, thereby constituting new or preferred technical solutions.

DESCRIPTION OF THE DRAWINGS

FIG. 8 shows the subcellular distribution of Cy5-labeled LPGL liposome under the condition that the mixture of Cy5-labeled LPGL liposome and serum-free medium or 10% FBS (fetal bovine serum)-containing medium is incubated with BxPC3 cells, and treated with or without ultrasound stimulation. (8A) The mixture of Cy5-labeled LPGL lysosome and serum-free medium or 10% FBS (fetal bovine serum)-containing medium is incubated with BxPC3 cells, and treated with or without ultrasound stimulation (acoustic intensity: 2 W/$cm^2$, frequency: 3 MHz, duty cycle: 50%, duration time: 5 min), and continuously incubated for 1 h, the subcellular distribution images of Cy5-labeled LPGL liposome in BxPC3 cells are photographed using CLSM. (8B) The Mander's overlap coefficient (MOC) of Cy5-labeled LPGL liposome with lysosomes as shown in FIG. 8A is analyzed using the image analysis software Cellprofiler V2.2.0, Scale bar=25 μm. *: $P<0.05$, "ns" represents Not Statistically.

FIG. 10 shows the cytotoxicity and penetration of free GEM and different liposome on the three-dimensional (3D) multicellular tumor spheroids. (10A) shows the inhibitory effect of gemcitabine (GEM) and different liposomes on the three-dimensional (3D) multicellular tumor spheroids of BxPC3 or Huh7 under the condition the mixture of LPGL liposome, PGL liposome, LGL liposome, GL liposome or free gemcitabine (GEM) and serum-containing medium is incubated with three-dimensional (3D) multicellular tumor spheroids of BxPC3 or Huh7, and treated with ultrasound stimulation (acoustic intensity: 2 W/$cm^2$, frequency: 3 MHz, duty cycle: 50%, duration time: 5 min). (10B) shows the $IC_{50}$ (50% inhibiting concentration) value of free gemcitabine (GEM) and different liposomes on the three-dimensional (3D) multicellular tumor spheroids of BxPC3 or Huh7 under the condition the mixture of LPGL liposome, PGL liposome, LGL liposome, GL liposome or free gemcitabine (GEM) and serum-containing medium is incubated with three-dimensional (3D) multicellular tumor spheroids of BxPC3 or Huh7, and treated with ultrasound stimulation (acoustic intensity: 2 W/$cm^2$, frequency: 3 MHz, duty cycle:

50%, duration time: 5 min). (1° C.) shows the apoptosis of 3D multicellular tumor spheroids of BxPC3 before and after treatment of LPGL, PGL, LGL, GL liposome or free gemcitabine (GEM) using light microscope and TUNEL staining. The method for inhibiting 3D multicellular tumor spheroids of BxPC3 with free GEM and different liposomes is as follows: the mixture of LPGL, PGL, LGL, GL liposome, free gemcitabine (GEM) or PBS and serum-containing medium was incubated with 3D multicellular tumor spheroids of BxPC3 at the final testing concentrations (equivalent to GEM: 0.1 μM), and treated with ultrasound stimulation (acoustic intensity: 2 $W/cm^2$, frequency: 3 MHz, duty cycle: 50%, duration time: 5 min), then incubated for 72 h, the morphology of 3D multicellular tumor spheroids of BxPC3 in different treatment group was observed using light microscope and TUNEL staining, scale bar=500 μm. (10D) shows the mixture of different Cy5-labeled liposome and serum-containing medium was incubated with 3D multicellular tumor spheroids of BxPC3 pretreated with or without exocytosis inhibitor EXO1, and treated with ultrasound stimulation (acoustic intensity: 2 $W/cm^2$, frequency: 3 MHz, duty cycle: 50%, duration time: 5 min), then incubated for 6 h, CLSM images was obtained to determine the permeability of different Cy5-labeled liposome in 3D multicellular tumor spheroids of BxPC3, scale bar=500 μm. (10E) The mean integrated optical density (IOD) of fluorescence in two inner layers of 75 μm and 100 μm (as shown in FIG. 10 D) in 3D multicellular tumor spheroids of BxPC3 was analyzed using Image-pro Plus 6.0 software to evaluate the penetration ability of liposome.

Figure 11:
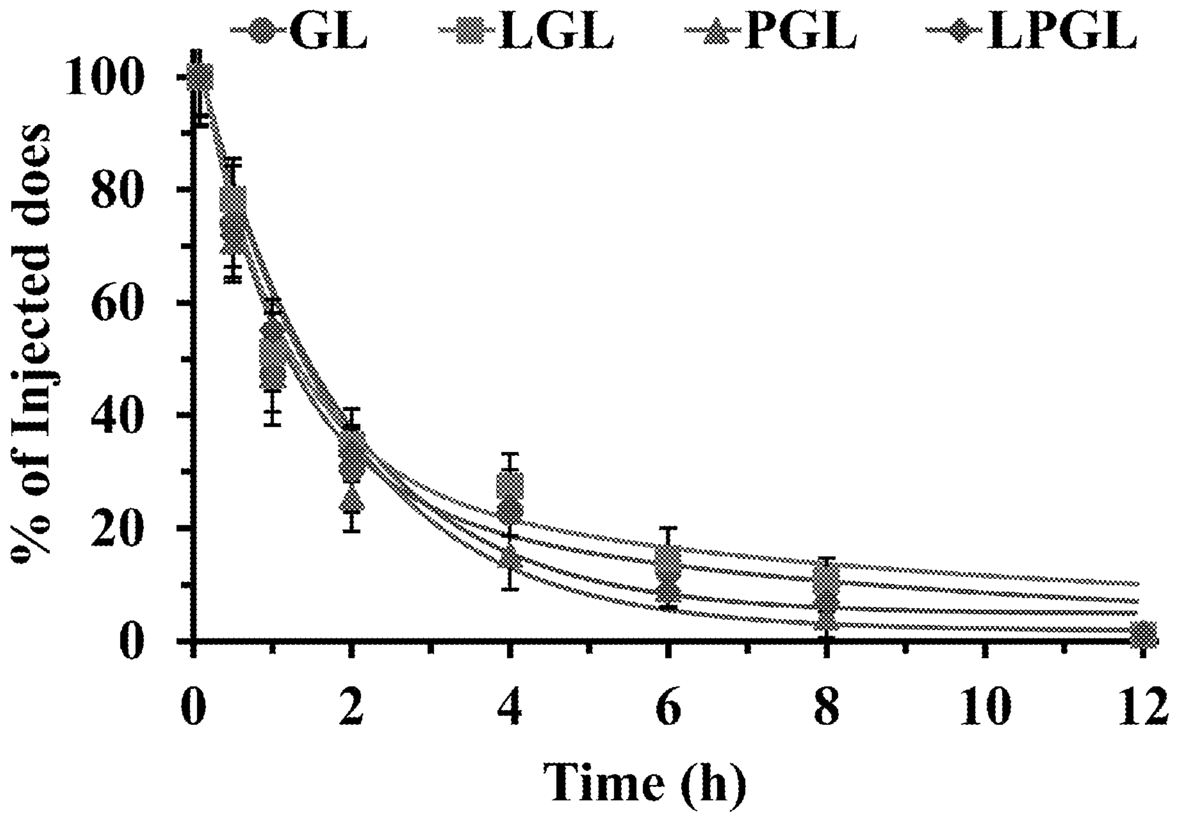

FIG. 11 shows the blood content of CP4126 at different time after intravenous injection of GL, LGL, PGL or LPGL liposome.

Figure 12:
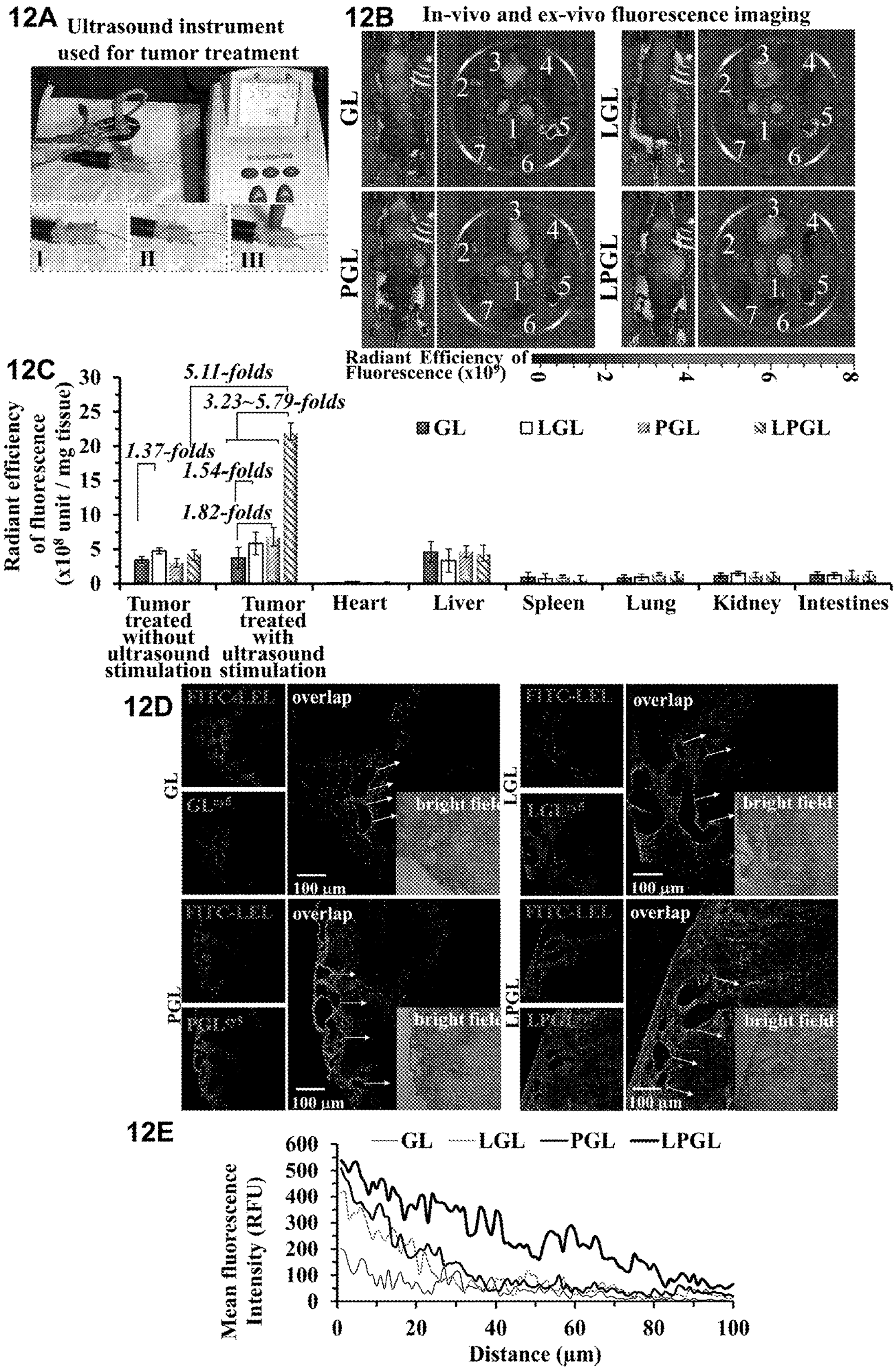

FIG. 12 shows the biodistribution, tumor accumulation and penetration of different Cy5-labeled liposome in BALB/c nude mice subcutaneously bearing human-derived tumor xenograft of PDA. (12A) is ultrasound instrument used for tumor treatment. (12B) After the mice subcutaneously bearing human-derived tumor xenograft of PDA were intravenously injected with different Cy5-labeled liposome, the PDA tumor on the right flank was treated with ultrasound stimulation (acoustic intensity: 2 $W/cm^2$, frequency: 3 MHz, duty cycle: 50%, duration time: 20 min) and the PDA tumor on the left flank was not treated with ultrasound stimulation, the fluorescence image of BALB/c nude mice bearing PDA tumors and excised tissues (1 represents tumor treated with and without ultrasound stimulation, 2 represents heart, 3 represents liver, 4 represents spleen, 5 represents lung, 6 represents kidney, 7 represents small intestine) was obtained at 12 h of post-injection using a fluorescent spectral imager of Caliper IVIS Lumina II. (12C) The fluorescence intensity of the tumor treated with and without ultrasound stimulation, heart, liver, spleen, lung, kidney and small intestine (as shown in FIG. 12B) was quantitatively analyzed using Living Image®-4.5 software. (12D) The CLSM images of the penetration of different Cy5-labeled liposome into tumor treated with ultrasound stimulation, the method is as follows: the mice subcutaneously bearing human-derived tumor xenograft of PDA were intravenously injected with the different Cy5-labeled liposome, the PDA tumor on the right flank was treated with ultrasound stimulation (acoustic intensity: 2 $W/cm^2$, frequency: 3 MHz, duty cycle: 50%, duration time: 20 min), and the PDA tumor on the left flank was not treated with ultrasound stimulation. At 12 h of post-injection, each mouse was intravenously injected with FITC-labeled *Lycopersicon esculentum* lectin to stain the blood vessel, and cardiac perfusion with 2% glutaraldehyde solution was performed. The tumor tissues treated with ultrasound stimulation were then collected, the collected tumor treated with ultrasound stimulation was frozen in Tissue OCT-Freeze Medium. After sectioning into 10-μm thick slices, the penetration image of liposome in the tumor treated with ultrasound stimulation were photographed using CLSM, scale bar=100 μm. (12E) The mean fluorescence intensity gradient from the tumor vessel to the deep tumor indicated by the arrow in FIG. 12D.

Figure 13:
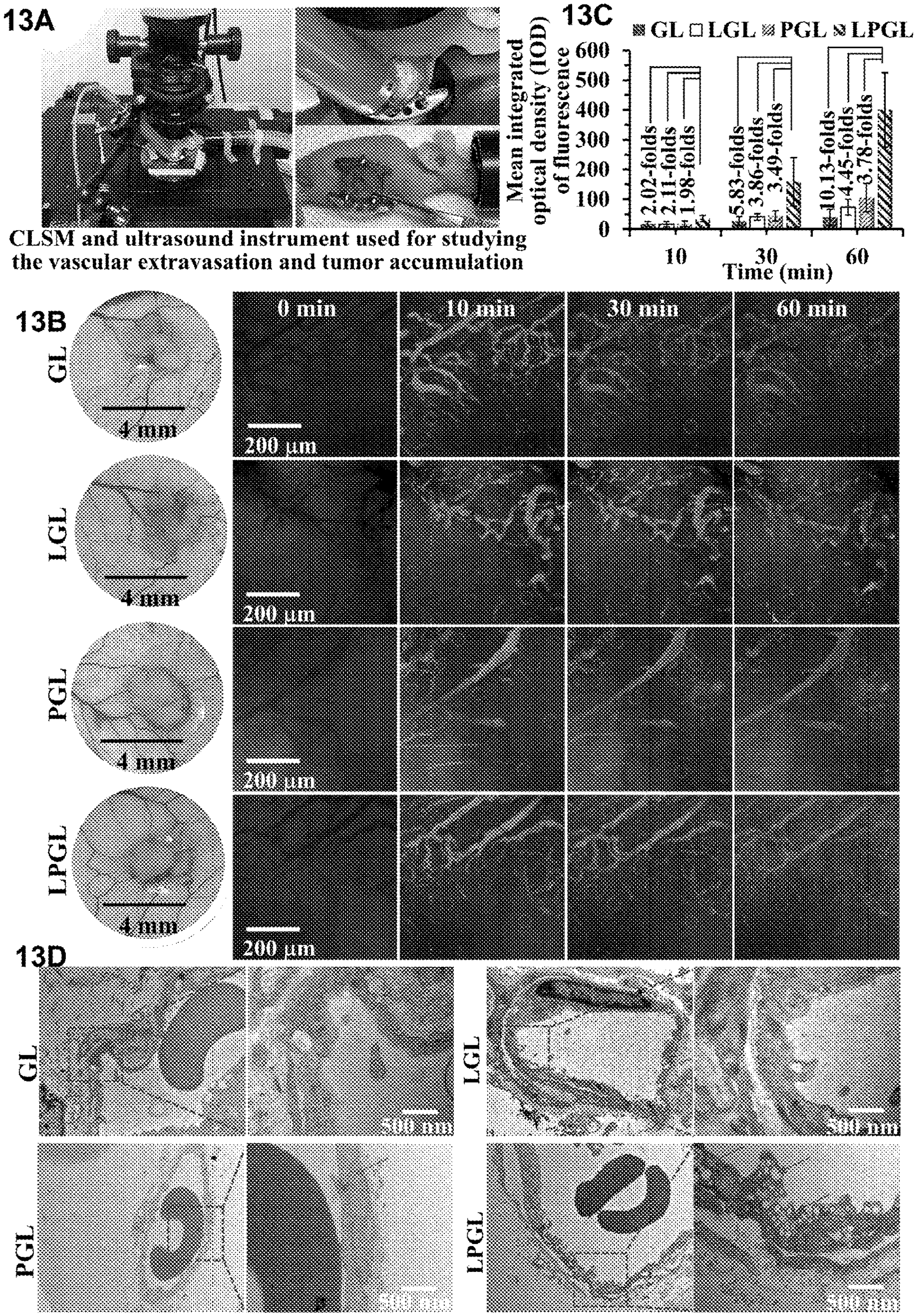

FIG. 13 shows the in vivo real-time vascular extravasation and tumor accumulation of different Cy5-labeled liposome in BALB/c nude mice subcutaneously bearing human-derived tumor xenograft of PDA. (13A) shows the CLSM and ultrasound instrument is used to study the in vivo real-time vascular extravasation and tumor accumulation of different Cy5-labeled liposome in BALB/c nude mice subcutaneously bearing human-derived tumor xenograft of PDA. (13B) shows after intravenous injection of different Cy5-labeled liposome, the tumor site is treated with ultrasound stimulation (acoustic intensity: 2 $W/cm^2$, frequency: 3 MHz, duty cycle: 50%, duration time: 20 min), the extravasation of different Cy5-labeled liposome from the vessels of PDA tumor to PDA tumor at 10 min, 30 min and 60 min of post-injection of different Cy5-labeled liposome was observed using CLSM, scale bar=200 μm. (13C) The mean integrated optical density (IOD) of fluorescence in the selected area (circle marking) of the FIG. 13B was quantitatively analyzed at 10 min, 30 min and 60 min of post-injection of different Cy5-labeled liposome. (13D) shows the ultrastructure of tumor vessels at 60 min of post-injection of different Cy5-labeled liposome (as shown in 13B) using Transmission electron microscope (TEM), the arrow shows the transendothelial transporter of the vesicle, scale bar=500 μm.

Figure 14:
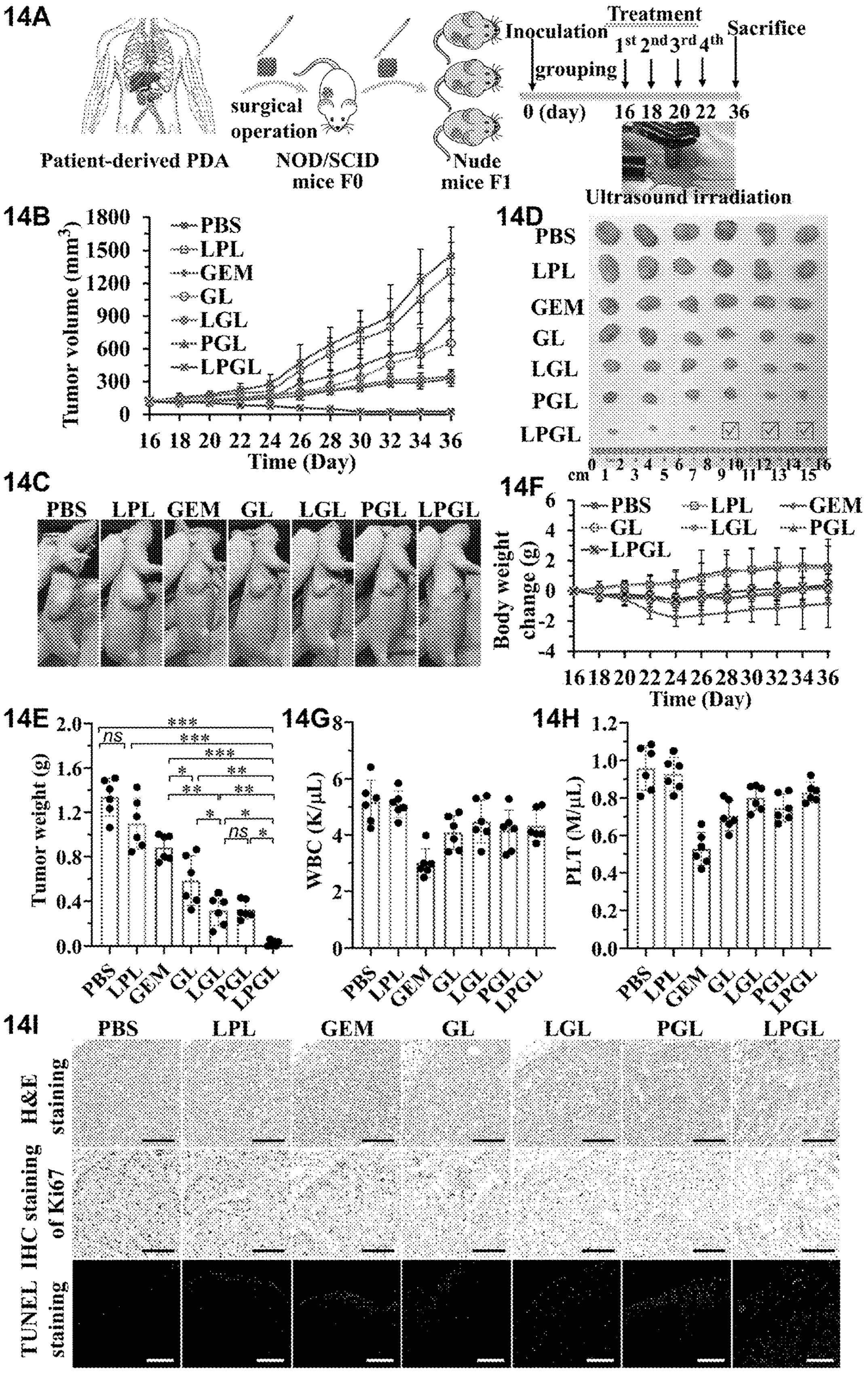

FIG. 14 shows the antitumor activity of the free GEM or different liposome in BALB/c nude mice subcutaneously bearing human-derived tumor xenograft of PDA. (14A) The establishment of BALB/c nude mice model subcutaneously bearing human-derived PDA tumor, experimental schedule and tumor treatment plan. After mice was intravenously injected with free GEM, GL liposome, LGL liposome, PGL liposome, LPGL liposome, LPL liposome or PBS 7.4, the tumor site was treated with ultrasound stimulation (acoustic intensity: 2 $W/cm^2$, frequency: 3 MHz, duty cycle: 50%, duration time: 20 min). (14B) The change of tumor volume in each group during treatment. (14C) Photos of mice in each group at the end of the 36-day experiment. (14D) Photos of excised tumor in each group at the end of the 36-day experiment. (14E) The average tumor weight of excised tumor in each group at the end of the 36-day experiment. (14F) The change of body weight in each group during treatment. (14G) The value of white blood cell (WBC) in each group at the end of the 36-day experiment. (14H) The value of blood platelet (PLT) in each group at the end of the 36-day experiment. (14I) The H&E staining, immunohistochemistry (IHC) staining of Ki67 and TUNEL staining of the excised tumors at the end of the 36-day experiment, scale bar==100 μm. *: $P<0.05$, : $P<0.01$, *: $P<0.001$, "ns" represents Not Statistically.

Figure 15:
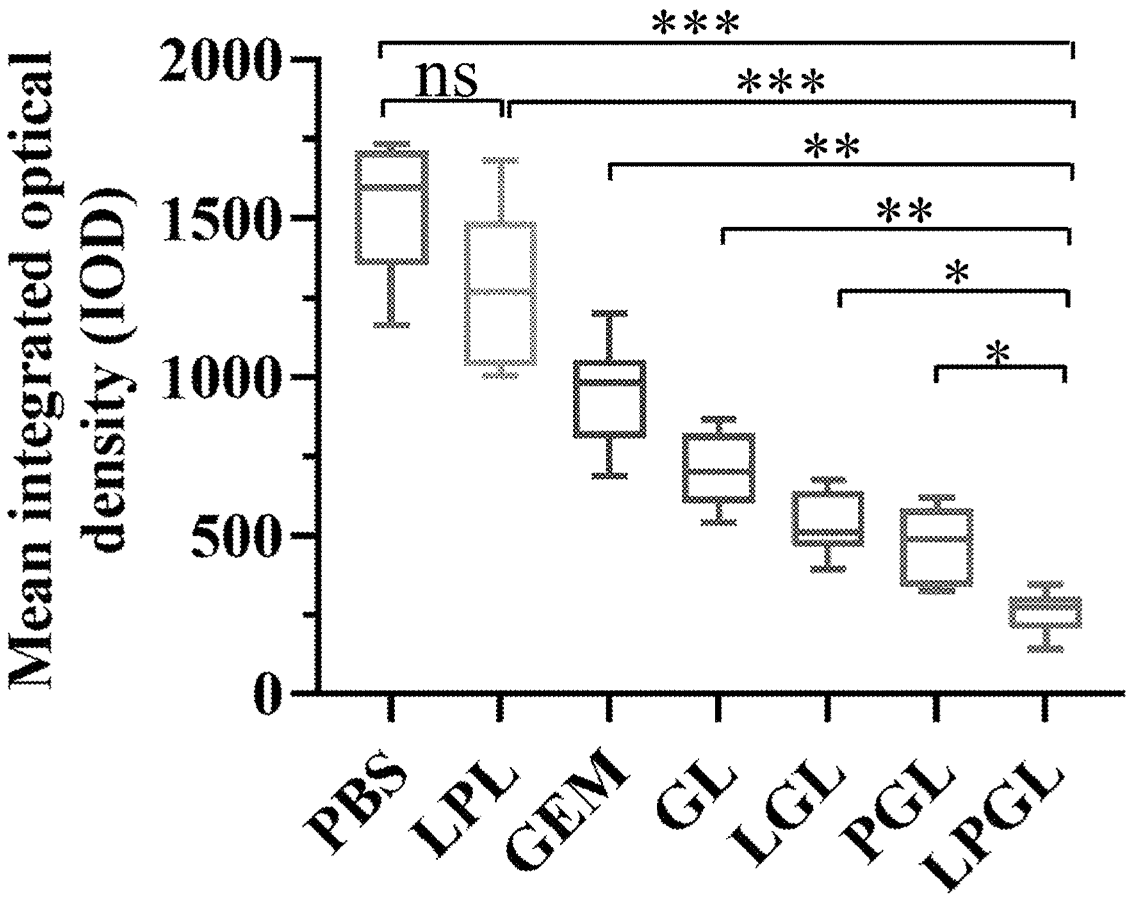

FIG. 15 shows the mean integrated optical density of Ki67-positive tumor cell in each group at the end of the 36-day experiment. *: $P<0.05$, : $P<0.01$, *: $P<0.001$, "ns" represents Not Statistically.

Figure 16:
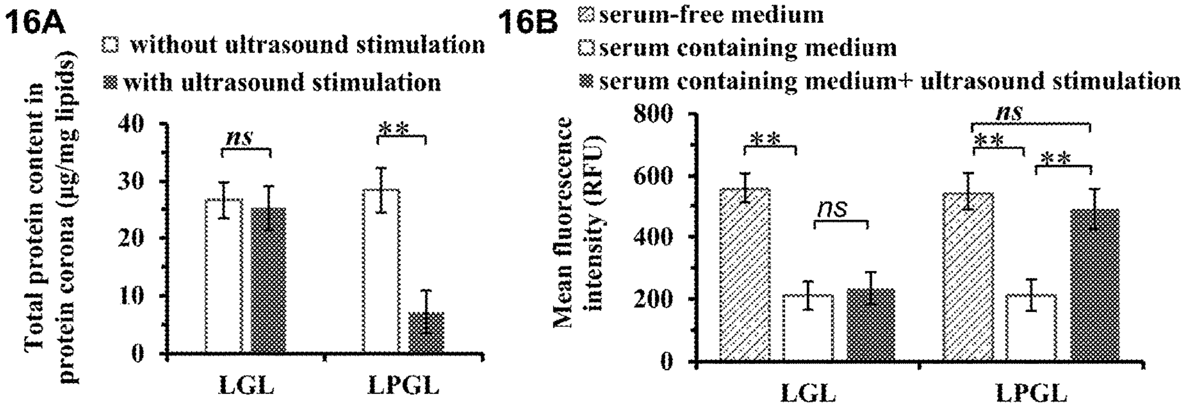

FIG. 16 shows the removal of protein corona on the surface of nanometer particle by ultrasound stimulation treatment and the uptake of nanometer particle in Huh7 cells. (16A) The NGR modified LPGL liposome or NGR modified LGL liposome is mixed with mouse plasma for 30 min, the mixture is treated with or without ultrasound stimulation (acoustic intensity: 2 $W/cm^2$, frequency: 3 MHz, duty cycle: 50%, duration time: 5 min), the total content of protein in protein corona of NGR modified LPGL liposome or NGR modified LGL liposome, wherein, the "+US" means the mixture is treated with ultrasound stimulation; "—US" means the mixture is treated without ultrasound stimulation. (16B) shows the mean fluorescence intensity of NGR modified LGL liposome or NGR modified LPGL liposome in Huh7 cells under the condition the mixture of NGR modified LGL liposome or NGR modified LPGL liposome and serum-free medium or 10% FBS (fetal bovine serum)-containing medium is incubated with Huh7 cells and then treated with or without ultrasound stimulation (acoustic intensity: 2 $W/cm^2$, frequency: 3 MHz, duty cycle: 50%, duration time: 5 min). Wherein, the "serum-free medium" means the mixture of NGR modified LGL liposome or NGR modified LPGL liposome and serum-free medium is incubated with Huh7 cells, and treated without ultrasound stimulation, then continuously incubated for 1 h, the mean fluorescence intensity of NGR modified LGL liposome or NGR modified LPGL liposome in Huh7 cells was detected using flow cytometry; the "serum-containing medium" means the mixture of NGR modified LGL liposome or NGR modified LPGL liposome and 10% FBS (fetal bovine serum)-containing medium is incubated with Huh7 cells, and treated without ultrasound stimulation, then continuously incubated for 1 h, the mean fluorescence intensity of NGR modified LGL liposome or NGR modified LPGL liposome in Huh7 cells was detected using flow cytometry; "serum-containing medium+ultrasound stimulation" means the mixture of NGR modified LGL liposome or NGR modified LPGL liposome and 10% FBS (fetal bovine serum)-containing medium is incubated with Huh7 cells, and then treated with ultrasound stimulation (acoustic intensity: 2 $W/cm^2$, frequency: 3 MHz, duty cycle: 50%, duration time: 5 min), then continuously incubated for 1 h, the mean fluorescence intensity of Cy5-labeled NGR modified LGL liposome or NGR modified LPGL liposome in Huh7 cells was detected using flow cytometry. **: $P<0.01$, "ns" represents Not Statistically.

Figure 17:
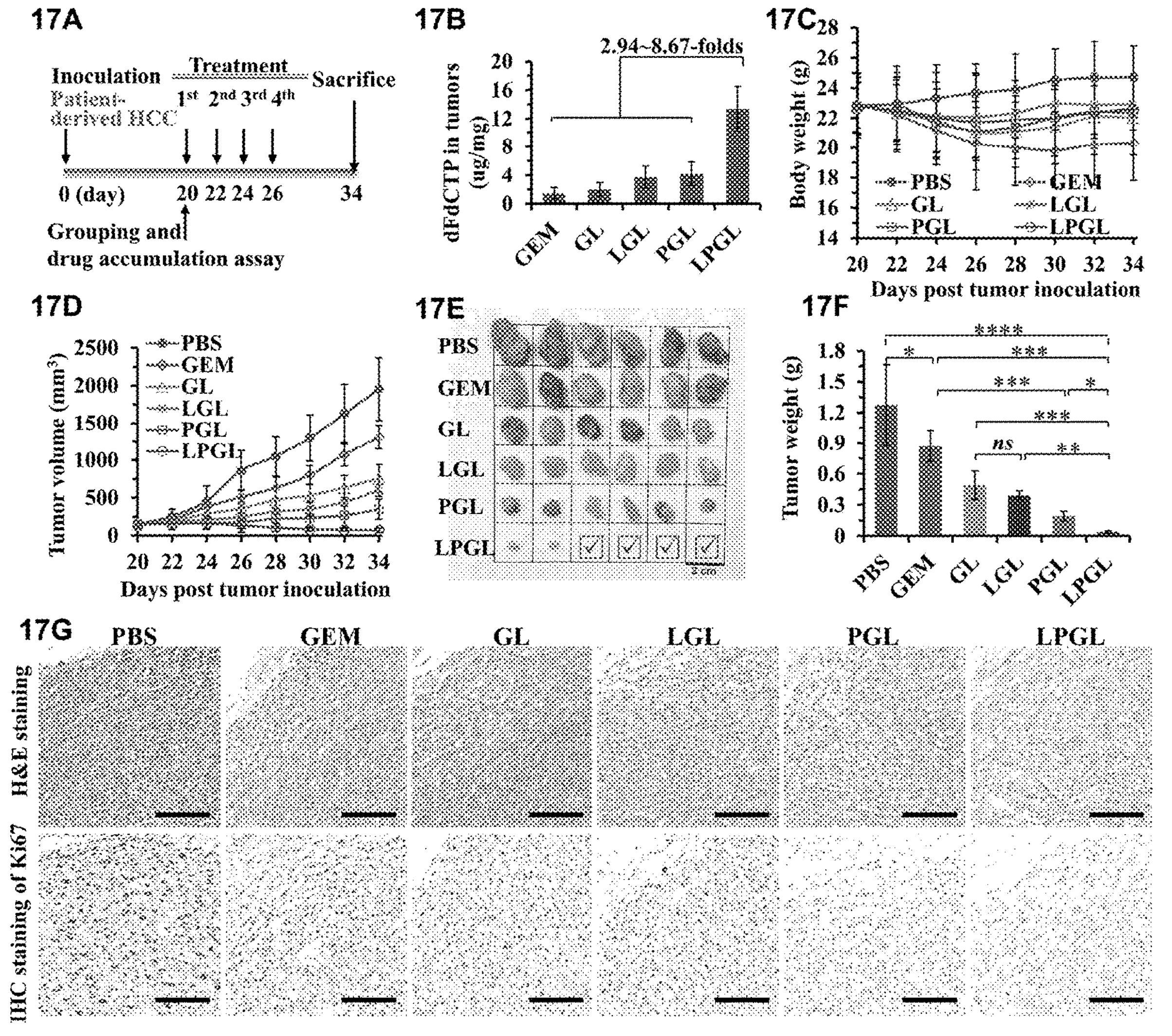

FIG. 17 shows the antitumor activity of the free GEM, GL liposome, NGR modified LGL, PGL liposome, NGR modified LPGL liposome or PBS 7.4 in BALB/c nude mice subcutaneously bearing human-derived tumor xenograft of HCC, wherein, the dose calculated by GEM in free GEM, GL liposome, NGR modified LGL, PGL liposome and NGR modified LPGL liposome group is the same. (17A) The experimental schedule and tumor treatment plan in BALB/c nude mice model subcutaneously bearing human-derived HCC tumor. After mice was intravenously injected with free GEM, GL liposome, NGR modified LGL, PGL liposome, NGR modified LPGL liposome or PBS 7.4, the tumor site was treated with ultrasound stimulation (acoustic intensity: 2 $W/cm^2$, frequency: 3 MHz, duty cycle: 50%, duration time: 20 min). (17B) The accumulation content of gemcitabine triphosphate active metabolite (dFdCTP) in the tumor after 24 h of first intravenous injection in each group. (17C) The change of body weight in each group during treatment. (17D) The change of tumor volume in each group during treatment. (17E) Photos of excised tumor in each group at the end of the 34-day experiment. (17F) The average weight of excised tumor at the end of the 34-day experiment. (17G) The H&E staining and immunohistochemistry (IHC) staining of Ki67 of the excised tumors at the end of the 34-day experiment, scale bar=100 μm. *: $P<0.05$, : $P<0.01$, *: $P<0.001$, "ns" represents Not Statistically.

EMBODIMENTS FOR CARRYING OUT THE INVENTION

The present invention develops a nanometer particle, the nanometer particle comprises perfluoropentane. Ultrasound stimulation can remove protein corona on the surface of nanometer particle, overcome the masking effect of the protein corona on the ligand of the nanometer particle surface, recover the binding of the ligand modified on the surface of nanometer particle to the receptor of target cell (e.g., tumor vascular cell or tumor cell), improve the uptake of the ligand-modified nanometer particle in cell, thus enhancing the antitumor effect of anti-tumor drug loaded in nanometer particle. Moreover, the nanometer particle of the present invention can be used as a carrier for screening or identifying potential ligand targeting cell or cell surface receptor under ultrasound stimulation. Additionally, the nanometer particle has excellent lysosomal escape ability to avoid lysosome retention and degradation under ultrasound stimulation, lysosomal escape can effectively protect the nanometer particle and drug loaded in the nanometer particle from being damaged and degraded by lysosome enzyme, thus enhancing the stability of nanometer particle and drug loaded in the nanometer particle in the cell and improving the therapeutic effect of drug.

Terms

Unless otherwise defined, all technical and scientific terms used herein have the same meaning as commonly understood by those skilled in the art of the invention.

As used herein, the term "comprise", "comprising", and "containing" are used interchangeably, which not only comprise closed definitions, but also semi-closed and open definitions. In other words, the term comprises "consisting of" and "essentially consisting of".

As used herein, the term "cancer" and "tumor" are used interchangeably.

As used herein, "Cryo-TEM" refers to Cryo-transmission electron microscope.

As used herein, "DSPE-PEG" refers to 1,2-distearoyl-sn-glycero-3-phosphoethanolamine-N-[methoxy (polyethylene glycol)].

As used herein, "DSPE-PEG2000" refers to 1,2-distearoyl-sn-glycero-3-phosphoethanolamine-N-[methoxy (polyethylene glycol)-2000].

As used herein, "DPPC" refers to 1,2-dipalmitoyl-sn-glycero-3-phosphocholine.

As used herein, "FBS" refers to fetal bovine serum.

As used herein, "GEM" refers to gemcitabine.

As used herein, "Cy5" refers to Cyanine 5.

As used herein, "Cy5.5" refers to Cyanine 5.5.

As used herein, "TUNEL" refers to TdT-mediated dUTP nick end labeling.

As used herein, the term "CLSM" refers to confocal laser scanning microscope.

As used herein, the term "$IC_{50}$" refers to 50% inhibiting concentration, ie, the concentration of the inhibitor at which 50% inhibition is achieved.

As used herein, the terms "gemcitabine prodrug CP4126" and "CP4126" are used interchangeably, and the structure of gemcitabine prodrug CP4126 is as follows.

CP4126

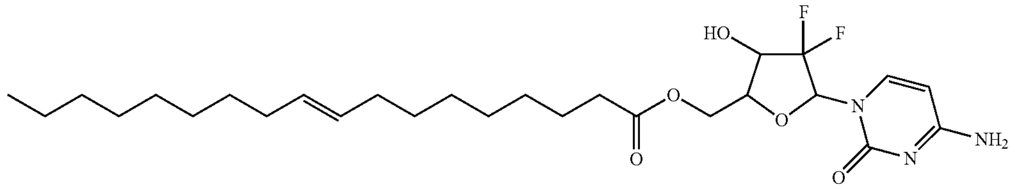

As used herein, the term "glycerol-containing phosphate buffer saline" refers to a phosphate buffer saline solution containing glycerol, wherein the concentration (e.g., mM) refers to the concentration of phosphate radical.

As used herein, the term "+US" refers to the treatment with ultrasound irradiation.

As used herein, the term "−US" refers to the treatment without ultrasound irradiation.

As used herein, the term "PBS", "phosphate buffer saline" and "PBS buffer" are used interchangeably, and refer to phosphate buffer saline aqueous solution.

As used herein, the term "serum-containing medium" and "serum-containing culture medium" are used interchangeably.

As used herein, the term "serum-free medium" and "serum-free culture medium" are used interchangeably.

As used herein, the term "protein-containing medium" and "protein-containing culture medium" are used interchangeably.

As used herein, the term "10% FBS-containing medium" and "10% FBS-containing culture medium" are used interchangeably.

As used herein, the term "RPMI 1640 medium" and "RPMI 1640 culture medium" are used interchangeably, and refer to Roswell Park Memorial Institute 1640 medium.

As used herein, the term "DMEM medium" and "DMEM culture medium" are used interchangeably, and refer to Dulbecco's Modified Eagle Medium.

As used herein, the term "RGD", "RGD peptide", "RGD targeting peptide" and "RGD ligand" are used interchangeably and have the amino acid sequence Cys (cysteine)-Arg (arginine)-Gly (glycine)-Asp (aspartic acid)-Lys (lysine)-Gly (glycine)-Pro (proline)-Asp (aspartic acid)-Cys (cysteine).

As used herein, the terms "NGR", "NGR peptide", "NGR targeting peptide" and "NGR ligand" are used interchangeably and have the amino acid sequence Gly (glycine)-Gly (glycine)-Cys (cysteine)-Asn (asparagine)-Gly (glycine)-Arg (arginine)-Cys (cysteine).

As used herein, the term "DSPE-PEG-ligand" refers to the ligand coupled to DSPE-PEG, e.g.

DSPE-PEG2000-RGD (1,2-distearoyl-sn-glycero-3-phosphoethanolamine-N-[methoxy (polyethylene glycol)-2000]-RGD) refers to RGD coupled to DSPE-PEG2000. DSPE-PEG2000-NGR (1,2-distearoyl-sn-glycero-3-phosphoethanolamine-N-[methoxy (polyethylene glycol)-2000]-NGR) refers to NGR coupled to DSPE-PEG2000.

As used herein, the term "ultrasound irradiation" and "ultrasound stimulation" are used interchangeably.

As used herein, the term "LPGL" and "LPGL liposome" are used interchangeably.

As used herein, the term "LGL" and "LGL liposome" are used interchangeably.

As used herein, the term "PGL" and "PGL liposome" are used interchangeably.

As used herein, the term "GL" and "GL liposome" are used interchangeably.

As used herein, the term "LPL" and "LPL liposome" are used interchangeably.

As used herein, the term "protein corona modified nanometer particle" and "nanometer particle modified by protein corona" are used interchangeably.

In the present invention, the term "prevention" refers to a method of preventing the occurrence of disease and/or its complications, or protecting a subject from getting disease.

In the present invention, the term "treatment" comprises inhibiting, alleviating, relieving, reversing or eradication the progression of the disease, and does not require 100% inhibition, elimination and reversal.

In some embodiments, compared to the level observed in the absence of the drug-loaded nanometer particle of the present invention, the drug-loaded nanometer particle of the present invention alleviates, inhibits and/or reverses related diseases (e.g., tumor) and its complications such as at least about 30%, at least about 50%, at least about 80%, at least about 90%, at least about 95%, or at least about 100%.

In the present invention, the term "removing" comprises decreasing, reducing, or eliminating, and does not require 100% elimination. In some embodiments, compared to the protein content of protein corona observed in the protein corona modified nanometer particle treated without ultrasound stimulation, the protein content of protein corona observed in the protein corona modified nanometer particle treated with ultrasound stimulation decreases by such as at least 70%, at least 80%, at least 90%, at least 95%, or 100%, such as 80-90%.

Tumor

The tumor of the present invention can comprise but be not limited to human tumor or non-human mammalian tumor.

Preferably, the non-human mammal comprises mice, rat, rabbit, monkey, bovine, horse, sheep, dog, cat, orangutan or baboon.

In a preferred embodiment, the tumor comprises lowly permeable tumor.

Preferably, the tumor comprises tumor with low permeability of tumor vessel.

Preferably, the tumor comprises solid tumor.

Preferably, the tumor comprises solid tumor with low permeability of tumor vessel.

In a preferred embodiment, the tumor comprises liver cancer.

Preferably, the tumor comprises human liver cancer.

Preferably, the liver cancer cell comprises Huh7 cell and/or HepG2 cell.

In a preferred embodiment, the tumor comprises pancreatic cancer.

Preferably, the pancreatic cancer comprises pancreatic adenocarcinoma.

Preferably, the pancreatic cancer comprises orthotropic pancreatic cancer.

Preferably, the pancreatic cancer comprises orthotropic pancreatic adenocarcinoma.

Preferably, the pancreatic cancer comprises pancreatic ductal adenocarcinoma.

Preferably, the pancreatic cancer comprises human pancreatic ductal adenocarcinoma.

Preferably, the pancreatic cancer cell comprises BxPC-3 cell.

In a preferred embodiment, the tumor comprises tumor with poor Enhanced Permeability and Retention effect.

Preferably, the low permeability of tumor vessel comprises low permeability of drug from tumor vessel to tumor site.

Preferably, the low permeability of tumor vessel comprises low permeability of drug from tumor vessel cell gap to tumor site.

In a preferred embodiment, the tumor vessel of the lowly permeable tumor comprises one or more features selected from the following groups:

(a) the tumor vascular cell is well organized and tightly stacked; and/or (b) the tumor vessel cell gap is small.

Preferably, the vascular cell comprises vascular endothelial cell.

Cell

The cell of the present invention can comprise but be not limited to tumor cell and/or tumor vascular cells, etc.

In a preferred embodiment, the cell comprises tumor cell.

Preferably, the tumor cell comprises Huh7 cell, HepG2 cell and/or BxPC-3 cell.

In a preferred embodiment, the cell comprise tumor vascular cell.

Preferably, the tumor vascular cell comprises tumor vascular endothelial cell.

Preferably, the tumor vascular cell comprises ECDHCC cell.

Preferably, the cell comprises the cell that need to be cultured or grown in protein-containing condition.

Preferably, the cell comprises the cell that need to be cultured or grown in serum-containing medium.

Preferably, the serum comprises fetal bovine serum.

Preferably, the volume fraction of the serum is 5-15%, preferably 8-12%, more preferably 10% in the serum-containing culture medium.

Ligand

The ligand of the present invention can comprise but be not limited to polypeptide ligand or protein ligand.

In a preferred embodiment, the ligand comprises the ligand targeting cell receptor or cell surface receptor.

Preferably, the cell surface receptor comprises receptor on the surface of cell membrane.

Preferably, the cell surface receptor comprises receptor on the outer surface of cell membrane.

Preferably, the surface comprises outer surface.

In a preferred embodiment, the ligand comprises ligand mediating uptake of the ligand-modified nanometer particle by cell.

In a preferred embodiment, the ligand comprises ligand mediating endocytosis of the ligand-modified nanometer particle by cell.

In a preferred embodiment, the ligand comprises ligand mediating endocytosis and exocytosis of the ligand-modified nanometer particle by cell.

In a preferred embodiment, the ligand can mediate the penetration of the ligand-modified nanometer particle from tumor vessel into tumor site.

In a preferred embodiment, the ligand can mediate the penetration of the ligand-modified nanometer particle from tumor vessel into tumor site via endocytosis and exocytosis.

In a preferred embodiment, the ligand can target tumor vascular endothelial cell and mediate the endocytosis and exocytosis of the ligand-modified nanometer particle by tumor vascular endothelial cell.

In a preferred embodiment, the ligand can mediate endocytosis of the ligand-modified nanometer particle in the blood by tumor vascular endothelial cell, then mediate exocytosis of the ligand-modified nanometer particle into extravascular of tumor (e.g., tumor tissue microenvironment).

Preferably, the ligand comprises RGD polypeptide and/or NGR polypeptide.

Drug

The drug of the present invention is not specially limited, the drug can comprise but be not limited to anti-tumor drug.

In a preferred embodiment, the drug comprises a drug unstable in the lysosome of cell.

Preferably, the drug comprises a drug retained and/or degraded by the lysosome of cell.

Preferably, the degradation comprises lysosomal enzyme degradation.

Preferably, the drug comprises a drug degraded by the lysosomal enzyme.

In a preferred embodiment, the action target of the drug is in the cytoplasm or nucleus.

In a preferred embodiment, the drug comprises gene or protein.

Preferably, the gene comprises but is not limited to DNA, RNA, and combinations thereof.

In a preferred embodiment, the drug comprises anticancer drug.

Preferably, the anticancer drugs comprises chemical drug.

Representatively, the anticancer drug comprises but is not limited to gemcitabine, cytarabine, adriamycin, fluorouracil, and combinations thereof.

In a preferred embodiment, the drug comprises free drug or prodrug.

Preferably, the drug comprises prodrug.

Preferably, the prodrug comprises the prodrug obtained by modifying the free drug on the prodrug carrier.

Preferably, the prodrug comprises the prodrug obtained by connecting the free drug with the prodrug carrier via chemical bonds.

In a preferred embodiment, the drug comprises hydrophobic drug or hydrophilic drug.

Preferably, the free drug comprises hydrophobic drug or hydrophilic drug.

Preferably, the free drug comprises anticancer drug.

Preferably, the prodrug carrier comprises hydrophobic carrier or hydrophilic carrier.

Preferably, the prodrug carrier comprises higher fatty acid carrier or higher fatty alcohol carrier.

Preferably, the prodrug carrier comprises higher fatty acid containing 12-26 (preferably 14-22, more preferably 16-20) carbon atoms.

Preferably, the prodrug carrier comprises higher fatty alcohol containing 12-26 (preferably 14-22, more preferably 16-20) carbon atoms.

Representatively, the higher fatty acid carrier comprises but is not limited to palmitic acid (hexadecanoic acid), margaric acid (heptadecanoic acid), stearic acid (octadecanoic acid), oleic acid (octadecenoic acid), linoleic acid (octadecadienoic acid), linolenic acid (octadecatrienoic acid), arachidic acid (eicosanoic acid), eicosapentaenoic acid, behenic acid (docosanoic acid), DHA (docosahexaenoic acid), lignoceric acid (tetracosanoic acid), and combinations thereof.

Preferably, the oleic acid comprises elaidic acid.

Representatively, the higher fatty alcohol comprises but is not limited to palmityl alcohol, stearyl alcohol, oleyl alcohol, linoleic alcohol, linolenic alcohol, arachidyl alcohol, eicosapentaenol, behenyl alcohol, docosahexaenol, and combinations thereof.

In a preferred embodiment, the prodrug comprises amphiphilic prodrug.

Preferably, the amphiphilic prodrug is used as nanomaterial of the nanometer particle.

Preferably, the amphiphilic prodrug is used as nanomaterial of the nanoparticle.

Preferably, the amphiphilic prodrug is used as lipid material of the liposome.

Preferably, the drug active ingredient comprises anticancer drug.

Preferably, the prodrug comprises:

(I)

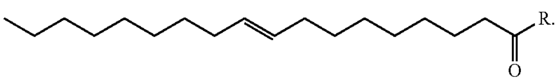

wherein, R is anticancer drug.

Preferably, the anticancer drug comprises gemcitabine, cytarabine, adriamycin, fluorouracil, and combinations thereof.

Preferably, the drug comprises gemcitabine elaidate.

Preferably, the prodrug comprises gemcitabine elaidate.

Preferably, the gemcitabine elaidate has the structure as follows:

CP4126

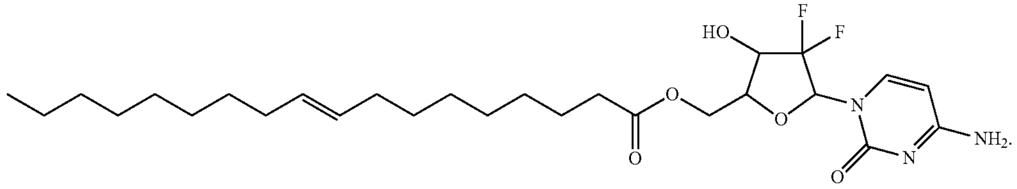

Preferably, the amphiphilic prodrug is used as lipid bilayer.

Preferably, the amphiphilic prodrug comprises a drug active ingredient as hydrophilic part and the prodrug carrier as hydrophobic part.

Preferably, the amphiphilic prodrug comprises a drug active ingredient as hydrophobic part and the prodrug carrier as hydrophilic part.

Representatively, the prodrug comprises:

D—C wherein, "D" is drug active ingredient, "C" is prodrug carrier, and "–" is connection bond.

Preferably, the drug active ingredient comprises a drug active ingredient unstable in the lysosome of cell.

Preferably, the drug active ingredient comprises hydrophobic drug active ingredient or hydrophilic drug active ingredient.

Preferably, the drug active ingredient comprises a drug active ingredient retained and/or degraded by the lysosome of cell.

Preferably, the degradation comprises lysosomal enzyme degradation.

Preferably, the drug active ingredient comprises a drug active ingredient degraded by the lysosomal enzyme.

Preferably, the action target of the drug active ingredient is in the cytoplasm or nucleus.

Preferably, the drug active ingredient comprises gene or protein.

Preferably, the gene comprises but is not limited to DNA, RNA, and combinations thereof.

Non-Human Mammal

The non-human mammal of the present invention is not specially limited, the non-human mammal can comprise but be not limited to mice, rat, rabbit, monkey, bovine, horse, sheep, dog, cat, orangutan or baboon.

Preferably, the bovine comprises fetal bovine.

Ultrasound Stimulation

The acoustic intensity, frequency, duty cycle and time of ultrasound stimulation can be determined according to specific requirements.

Preferably, the acoustic intensity of ultrasound stimulation is 0.1-40 W/$cm^2$, preferably 0.1-20 W/$cm^2$, more preferably 0.2-15 W/$cm^2$, more preferably 0.5-10 W/$cm^2$, more preferably 1-5 W/$cm^2$, more preferably 1-3 W/$cm^2$, more preferably 1.5-2.5 W/$cm^2$, more preferably 1.8-2.2 W/$cm^2$, most preferably 2.0 W/$cm^2$.

Preferably, the frequency of ultrasound stimulation is 0.02-30 MHz, preferably 0.1-20 MHz, more preferably 0.2-15 MHz, more preferably 0.5-10 MHz, more preferably 1-8 MHz, more preferably 1-5 MHz, more preferably 2-4 MHz, more preferably 2.5-3.5 MHz, more preferably 2.8-3.2 MHz, most preferably 3 MHz.

Preferably, the duty cycle of ultrasound stimulation is 10-80%, preferably 20-80%, more preferably 30-70%, more preferably 35-65%, more preferably 40-60%, more preferably 45-55%, more preferably 48-52%, most preferably 50%.

Preferably, the time of ultrasound stimulation is $\geq$2 min, preferably $\geq$5 min, preferably $\geq$10 min, preferably $\geq$15 min, such as 15-20 min or 25-35 min.

Protein-Containing Condition

The protein-containing condition of the present invention can comprise but be not limited to blood, serum, plasma, tissue microenvironment and/or culture medium.

In a preferred embodiment, the blood, serum or plasma comprises in vitro or isolated blood, serum or plasma.

Preferably, the blood, serum or plasma comprises human or non-human mammalian blood, serum or plasma.

In a preferred embodiment, the protein comprises serum protein, plasma protein and/or tissue protein.

In a preferred embodiment, the serum protein, plasma protein and/or tissue protein comprise in vitro or isolated serum protein, plasma protein and/or tissue protein.

Preferably, the serum protein, plasma protein and/or tissue protein comprise human or non-human mammalian serum protein, plasma protein and/or tissue protein.

Preferably, the non-human mammal comprises mice, rat, rabbit, monkey, bovine, horse, sheep, dog, cat, orangutan or baboon.

Preferably, the bovine comprises fetal bovine.

Preferably, the serum comprises fetal bovine serum.

Preferably, the plasma comprises fetal bovine plasma.

In a preferred embodiment, the culture medium comprises fluid culture medium.

In a preferred embodiment, the culture medium comprises cell culture medium.

In a preferred embodiment, the culture medium comprises protein-containing medium.

In a preferred embodiment, the culture medium comprises protein.

In a preferred embodiment, the culture medium comprises serum protein, plasma protein and/or tissue protein.

In a preferred embodiment, the culture medium comprises serum, plasma and/or tissue protein-containing culture medium.

Preferably, the culture medium comprises serum-containing culture medium.

Preferably, the volume fraction of the serum is 5-15%, preferably 8-12%, more preferably 10% in the serum-containing culture medium.

Nanometer Particle and Preparation Method

The nanometer particle of the present invention refers to micro particle in nanometer scale.

In a preferred embodiment, the nanometer particle comprises perfluoropentane.

In a preferred embodiment, the nanometer particle encapsulates perfluoropentane.

In a preferred embodiment, the nanometer particle is nanoparticle or liposome.

In a preferred embodiment, the nanometer particle of the present invention is nanoparticle. The nanoparticle is colloidal particle made of natural or synthetic polymer materials.

In a preferred embodiment, the nanometer particle of the present invention is liposome. The liposome is a particle with a bilayer structure, and is similar to a cell membrane.

In a preferred embodiment, the nanoparticle comprises nanomaterial.

Preferably, the nanomaterial comprises amphiphilic nanomaterial.

Preferably, the nanomaterial comprises nanomaterial of the nanoparticle and/or lipid material of the liposome.

Preferably, the liposome comprises lipid material.

In a preferred embodiment, the lipid material comprises 1,2-dipalmitoyl-sn-glycero-3-phosphocholine (DPPC), 1,2-distearoyl-sn-glycero-3-phosphoethanolamine-N-[methoxy (polyethylene glycol)] (DSPE-PEG), 1,2-dioleoyl-sn-glycero-3-phosphoethanolamine (DOPE), soy bean phospholipid, phosphatidylcholine (PC, lecithin), cholesterol, phosphatidylethanolamine (PE, cephalin), phosphatidylserine (PS), phosphatidylinositol (PI), phosphatidylglycerol (PG), dicetyl phosphate (DCP), dimyristoylphosphatidylcholine (DMPC), distearoylphosphatidylcholine (DSPC), dilaurylphosphatidylcholine (DLPC), dioleoylphosphatidylcholine (DOPC), and combinations thereof.

Preferably, the lipid material comprises 1,2-dipalmitoyl-sn-glycero-3-phosphocholine (DPPC) and 1,2-distearoyl-sn-glycero-3-phosphoethanolamine-N-[methoxy (polyethylene glycol)] (DSPE-PEG).

Preferably, the 1,2-distearoyl-sn-glycero-3-phosphoethanolamine-N-[methoxy (polyethylene glycol)](DSPE-PEG) is selected from the group consisting of DSPE-PEG600, DSPE-PEG800, DSPE-PEG1000, DSPE-PEG2000, DSPE-PEG4000, DSPE-PEG6000, and combinations thereof.

In a preferred embodiment, the DPPC is 1-10 parts by weight, preferably 2-8 parts by weight, more preferably 4-6 parts by weight, most preferably 3 parts by weight.

In a preferred embodiment, the DSPE-PEG is 0.5-8 parts by weight, preferably 1-5 parts by weight, more preferably 1-3 parts by weight, most preferably 2 parts by weight.

In a preferred embodiment, the perfluoropentane is 0.01-0.5 parts by weight, preferably 0.02-0.2 parts by weight, more preferably 0.05-0.15 parts by weight, more preferably 0.08-0.12 parts by weight, most preferably 0.1 parts by weight.

Preferably, the weight ratio of the DPPC to the DSPE-PEG is 0.2-8:1, preferably 0.5-5:1, more preferably 1-2:1, more preferably 1.3-1.7:1, most preferably 1.5:1.

Preferably, the volume weight ratio (ml:mg) of the perfluoropentane to the DPPC is 1:20-40, preferably 1:25-35, more preferably 1:27-32, most preferably 1:30.

In a preferred embodiment, the nanometer particle comprises drug-loaded nanometer particle.

Preferably, the nanometer particle comprises drug-loaded nanoparticle or drug-loaded liposome.

Preferably, the drug is 0.5-8 parts by weight, preferably 1-5 parts by weight, more preferably 1-3 parts by weight, most preferably 2 parts by weight.

Preferably, the weight ratio of the DPPC to the drug is 0.2-8:1, preferably 0.5-5:1, more preferably 1-2:1, more preferably 1.3-1.7:1, most preferably 1.5:1.

Preferably, the nanometer particle further comprises water, buffer solution and/or perfluoropentane.

Preferably, the nanometer particle encapsulates water, buffer solution and/or perfluoropentane.

Preferably, the lipid bilayer of the liposome encapsulates water, buffer solution and/or perfluoropentane.

Preferably, the buffer solution comprises glycerol-containing phosphate buffer saline.

Preferably, the volume fraction of the glycerol is 5-15%, preferably 8-12%, more preferably 10% in the glycerol-containing phosphate buffer saline.

Preferably, the concentration of the glycerol-containing phosphate buffer saline is 5-15 mM, preferably 8-12 mM, more preferably 10 mM, based on the concentration of phosphate radical.

Preferably, the pH of the glycerol-containing phosphate buffer saline is 7.2-7.6, preferably 7.4.

Preferably, the lipid bilayer encapsulates perfluoropentane and/or glycerol-containing phosphate buffer saline.

Preferably, the encapsulated rate of the drug-loaded nanometer particle is ≥90%, preferably ≥95%, more preferably ≥99%, most preferably 100%.

Preferably, the drug loading rate of the drug-loaded nanometer particle is 8-15 wt %, preferably 9-11 wt %.

The present invention provides a method for preparing the nanometer particle of the present invention, which comprises the following steps:

(1) dissolving the nanomaterial in an organic solvent, and removing the organic solvent to obtain a nanometer particle film;

(2) immersing the perfluoropentane into the nanometer particle film, and hydrating the nanometer particle film with buffer solution, then stirring to obtain the nanometer particle.

In a preferred embodiment, the nanometer particle is drug-loaded nanometer particle, the method for preparing the drug-loaded nanometer particle comprises the following steps:

(1) dissolving the nanomaterial and drug in an organic solvent, and removing the organic solvent to obtain a nanometer particle film;

(2) immersing the perfluoropentane into the nanometer particle film, and hydrating the nanometer particle film with buffer solution, then stirring to obtain the drug-loaded nanometer particle.

Preferably, the nanometer particle is liposome, the method for preparing the liposome comprises the following steps:

(1) dissolving the lipid material in an organic solvent, and removing the organic solvent to obtain a lipid film;

(2) immersing the perfluoropentane into the lipid film, and hydrating the lipid film with buffer solution, then stirring to obtain the liposome.

Preferably, the nanometer particle is drug-loaded liposome, the method for preparing the drug-loaded liposome comprises the following steps:

(1) dissolving the lipid material and drug in an organic solvent, and removing the organic solvent to obtain a lipid film;

(2) immersing the perfluoropentane into the lipid film, and hydrating the lipid film with buffer solution, then stirring to obtain the drug-loaded liposome.

In a preferred embodiment, in the step (1), the organic solvent is selected from the group consisting of chloroform, dichloromethane, and combinations thereof.

In a preferred embodiment, in the step (1), the weight volume ratio (mg:ml) of the DPPC to the organic solvent is 1:0.2-5, preferably 1:0.5-2, more preferably 1:0.5-1.5, more preferably 1:0.8-1.2, most preferably 1:1.

Preferably, the volume ratio of the perfluoropentane to the buffer solution is 1:30-70, preferably 1:40-60, more preferably 1:45-55, most preferably 1:48-52.

In a preferred embodiment, in the step (1), the weight volume ratio (mg:ml) of the drug to the organic solvent is 1:2-5, preferably 1:1-2, more preferably 1:1.3-1.7, more preferably 1:1.5.

Preferably, in the step (1), the organic solvent is removed by rotary evaporation under reduced pressure.

Preferably, in the step (1), the organic solvent is removed by rotary evaporation under reduced pressure at 35-40° C.

Preferably, in the step (2), the perfluoropentane is immersed into the lipid film at a low temperature.

Preferably, in the step (2), the hydration is carried out at low temperature.

Preferably, in the step (2), the stirring comprises the following steps:

stirring at low temperature firstly, and then stirring at rising temperature.

Preferably, the low temperature is 2-10° C., preferably 2-6° C., most preferably 4° C.

Preferably, the stirring time under the low temperature is 0.2-0.8 h, preferably 0.4-0.6 h, more preferably 0.5 h.

Preferably, the rising temperature is 20-40° C., preferably 25-35° C., more preferably 28-32° C.

Preferably, the stirring time under the rising temperature is 0.5-1.5 h, preferably 0.8-1.2 h, more preferably 1 h.

Preferably, the stirring comprises magnetic stirrer stirring.

Preferably, in the stirring at rising temperature, the container in which the stirring solution is placed is open.

Preferably, the stirring at rising temperature can remove the unencapsulated perfluoropentane.

Preferably, the liposome is in the form of liposome nanodroplet.

Representatively, the method for preparing the liposome comprises the following steps:

(i) dissolving the DPPC and DSPE-PEG in an organic solvent, and removing the organic solvent by rotary evaporation under reduced pressure to obtain a lipid film in round bottom flask;

(ii) cooling the lipid film to low temperature and adding perfluoropentane to immerse the lipid film, then adding buffer solution to hydrate, stirring for 0.2-0.8 h at 2-6° C., and then stirring for 0.8-1.2 h at 25-35° C. in the open round bottom flask to obtain the liposome.

Typically, the method for preparing the liposome comprises the following steps:

(i) dissolving 2.8-3.2 mg of DPPC and 1.8-2.2 mg of DSPE-PEG in an organic solvent in round bottom flask, and removing the organic solvent by rotary evaporation under reduced pressure to obtain a lipid film in round bottom flask;

(ii) cooling the lipid film to 2-6° C. and adding 90-110 L of perfluoropentane to immerse the lipid film, then adding 4.5-5.5 ml of buffer solution to hydrate, stirring for 0.3-0.7 h at 2-6° C., and then stirring for 0.8-1.2 h at 28-32° C. in the open round bottom flask to obtain the liposome.

Representatively, the method for preparing the drug-loaded liposome comprises the following steps:

(i) dissolving the DPPC, DSPE-PEG and drug in an organic solvent, and removing the organic solvent by rotary evaporation under reduced pressure to obtain a lipid film in round bottom flask;

(ii) cooling the lipid film to low temperature and adding perfluoropentane to immerse the lipid film, then adding buffer solution to hydrate, stirring for 0.2-0.8 h at 2-6° C., and then stirring for 0.8-1.2 h at 25-35° C. in the open round bottom flask to obtain the drug-loaded liposome.

Typically, the method for preparing the drug-loaded liposome comprises the following steps:

(i) dissolving 2.8-3.2 mg of DPPC, 1.2-1.8 mg of DSPE-PEG and 1.8-2.2 mg of drug in an organic solvent in round bottom flask, and removing the organic solvent by rotary evaporation under reduced pressure to obtain a lipid film in round bottom flask;

(ii) cooling the lipid film to 2-6° C. and adding 90-110 L of perfluoropentane to immerse the lipid film, then adding 4.5-5.5 ml of buffer solution to hydrate, stirring for 0.3-0.7 h at 2-6° C., and then stirring for 0.8-1.2 h at 28-32° C. in the open round bottom flask to obtain the drug-loaded liposome.

Ligand-Modified Nanometer Particle and Preparation Method

The present invention provides a ligand-modified nanometer particle, ligand-modified nanometer particle comprises the nanometer particle of the present invention; and a ligand.

Preferably, the ligand-modified nanometer particle comprises ligand-modified nanoparticle or ligand-modified liposome.

In a preferred embodiment, the ligand comprises target ligand.

In a preferred embodiment, the surface of the nanometer particle comprises the ligand.

Preferably, the surface comprises outer surface.

Preferably, the surface of the nanometer particle comprises outer surface of the nanometer particle.

Preferably, the outer surface of the nanometer particle comprises ligand.

In a preferred embodiment, the ligand is modified on the nanometer particle.

Preferably, the ligand is modified on the nanomaterial of the nanometer particle.

Preferably, the ligand is modified on the surface of the nanometer particle.

Preferably, the modification comprises physical modification and/or chemical modification.

Preferably, the modification comprises physical adsorption, chemical adsorption and/or coupling.

Preferably, the ligand is adsorbed on the surface of the nanometer particle.

Preferably, the adsorption comprises physical adsorption and/or chemical adsorption.

Preferably, the ligand is coupled to the nanomaterial of the surface of the nanometer particle.

In a preferred embodiment, the ligand comprises the ligand targeting cell receptor or cell surface receptor.

Preferably, the ligand comprises the ligand targeting tumor vascular cell and/or tumor cell.

Preferably, the ligand comprises peptide ligand or protein ligand.

Preferably, the ligand comprises RGD polypeptide and/or NGR polypeptide.

In a preferred embodiment, the lipid material comprises ligand-modified lipid material.

Preferably, the ligand is coupled on the nanomaterial of the nanometer particle.

Preferably, the ligand is coupled to the lipid material.

Preferably, the coupling comprises chemical coupling.

In a preferred embodiment, the ligand is coupled on the 1,2-distearoyl-sn-glycero-3-phosphoethanolamine-N-[methoxy (polyethylene glycol)] (DSPE-PEG) to form DSPE-PEG-ligand.

In a preferred embodiment, the ligand is coupled on nanomaterial (e.g., lipid material).

Preferably, DSPE-PEG-ligand comprises DSPE-PEG-RGD and/or DSPE-PEG-NGR.

Preferably, the ligand coupled on the lipid material comprises DSPE-PEG-RGD and/or DSPE-PEG-NGR.

Preferably, the DSPE-PEG-RGD is selected from the group consisting of DSPE-PEG600-RGD, DSPE-PEG800-RGD, DSPE-PEG1000-RGD, DSPE-PEG2000-RGD, DSPE-PEG4000-RGD, DSPE-PEG6000-RGD, and combinations thereof.

Preferably, the DSPE-PEG-NGR is selected from the group consisting of DSPE-PEG600-NGR, DSPE-PEG800-NGR, DSPE-PEG1000-NGR, DSPE-PEG2000-NGR, DSPE-PEG4000NGR, DSPE-PEG6000-NGR, and combinations thereof.

In a preferred embodiment, the DSPE-PEG-ligand is 1-10 parts by weight, preferably 2-8 parts by weight, more preferably 4-6 parts by weight, most preferably 3 parts by weight.

In a preferred embodiment, the weight ratio of the DSPE-PEG-ligand to the DPPC is 1:0.2-5, preferably 1:0.5-2, more preferably 1:0.5-1.5, more preferably 1:0.8-1.2, most preferably 1:1.

In a preferred embodiment, the particle size of the ligand-modified nanometer particle is 120-260 nm, preferably 160-210 nm, more preferably 170-200 nm, most preferably 180-200 nm.

In a preferred embodiment, the potential of the ligand-modified nanometer particle is −2 mV to −18 mV, preferably −2 mV to −15 mV, most preferably −5 mV to −12 mV.

Preferably, the ligand comprises the ligand targeting the cell surface receptor.

Preferably, the ligand comprises the ligand targeting the receptor on the surface of tumor vascular cell.

Preferably, the ligand comprises the ligand targeting the receptor on the surface of tumor cell.

Preferably, the surface comprises outer surface.

Preferably, the cell surface receptor comprises receptor on the surface of cell membrane.

Preferably, the cell surface receptor comprises receptor on the outer surface of cell membrane.

Preferably, the receptor comprises protein receptor, lipoprotein receptor or glycoprotein receptor.

Preferably, the ligand comprises ligand mediating uptake of the ligand-modified nanometer particle by cell.

Preferably, the ligand comprises ligand mediating endocytosis of the ligand-modified nanometer particle by cell.

Preferably, the ligand comprises ligand mediating endocytosis and exocytosis of the ligand-modified nanometer particle by cell.

Preferably, the ligand can mediate the penetration of the ligand-modified nanometer particle from tumor vessel into tumor site.

Preferably, the ligand can mediate the penetration of the ligand-modified nanometer particle from tumor vessel into tumor site via endocytosis and exocytosis.

Preferably, the ligand can target tumor vascular endothelial cell and mediate the endocytosis and exocytosis of the ligand-modified nanometer particle by tumor vascular endothelial cell.

Preferably, the ligand can mediate endocytosis of the ligand-modified nanometer particle in the blood by tumor vascular endothelial cell, then mediate exocytosis of the ligand-modified nanometer particle into extravascular of tumor (e.g., tumor tissue microenvironment).

The present invention provides a method for preparing the ligand-modified nanometer particle of the present invention, which comprises the following steps:

modifying the ligand on the nanometer particle to obtain the ligand-modified nanometer particle.

In a preferred embodiment, the method for preparing the ligand-modified nanometer particle comprises the following steps:

(1) dissolving nanomaterial comprising the ligand-modified nanomaterial in an organic solvent, removing the organic solvent to obtain a nanometer particle film;

(2) immersing the perfluoropentane into the nanometer particle film, and hydrating the nanometer particle film with buffer solution, then stirring to obtain the ligand-modified nanometer particle.

Typically, the method for preparing the ligand-modified nanometer particle comprises the following steps:

(1) dissolving the nanomaterial comprising the ligand-modified nanomaterial and drug in an organic solvent, removing the organic solvent to obtain a nanometer particle film;

(2) immersing the perfluoropentane into the nanometer particle film, and hydrating the nanometer particle film with buffer solution, then stirring to obtain the ligand-modified nanometer particle.

Preferably, the nanomaterial comprising the ligand-modified nanomaterial comprises one or more of DPPC, DSPE-PEG and DSPE-PEG ligand.

Preferably, the nanomaterial comprising the ligand-modified nanomaterial comprises one or more of DPPC, DSPE-PEG, DSPE-PEG-RGD and DSPE-PEG-NGR.

Representatively, the method for preparing the ligand-modified liposome comprises the following steps:

(i) dissolving the DPPC, DSPE-PEG-ligand and DSPE-PEG in an organic solvent, and removing the organic solvent by rotary evaporation under reduced pressure to obtain a lipid film in round bottom flask;

(ii) cooling the lipid film to low temperature and adding perfluoropentane to immerse the lipid film, then adding buffer solution to hydrate, stirring for 0.2-0.8 h at 2-6° C., and then stirring for 0.8-1.2 h at 25-35° C. in the open round bottom flask to obtain the ligand-modified liposome.

Typically, the method for preparing the ligand-modified liposome comprises the following steps:

(i) dissolving 2.8-3.2 mg of DPPC, 2.8-3.2 mg of DSPE-PEG-ligand and 1.8-2.2 mg of DSPE-PEG in an organic solvent in round bottom flask, and removing the organic solvent by rotary evaporation under reduced pressure to obtain a lipid film in round bottom flask;

(ii) cooling the lipid film to 2-6° C. and adding 90-110 μL of perfluoropentane to immerse the lipid film, then adding 4.5-5.5 ml of buffer solution to hydrate, stirring at 2-6° C., and then stirring at 28-32° C. in the open round bottom flask to obtain the ligand-modified liposome.

Representatively, the method for preparing the ligand-modified liposome comprises the following steps:

(i) dissolving the DPPC, DSPE-PEG-ligand, DSPE-PEG and drug in an organic solvent, and removing the organic solvent by rotary evaporation under reduced pressure to obtain a lipid film in round bottom flask;

(ii) cooling the lipid film to low temperature and adding perfluoropentane to immerse the lipid film, then adding buffer solution to hydrate, stirring for 0.2-0.8 h at 2-6° C., and then stirring for 0.8-1.2 h at 25-35° C. in the open round bottom flask to obtain the ligand-modified liposome.

Typically, the method for preparing the ligand-modified liposome comprises the following steps:

(i) dissolving 2.8-3.2 mg of DPPC, 2.8-3.2 mg of DSPE-PEG-ligand, 1.8-2.2 mg of DSPE-PEG and 1.8-2.2 mg of drug in an organic solvent in round bottom flask, and removing the organic solvent by rotary evaporation under reduced pressure to obtain a lipid film in round bottom flask;

(ii) cooling the lipid film to 2-6° C. and adding 90-110 μL of perfluoropentane to immerse the lipid film, then adding 4.5-5.5 ml of buffer solution to hydrate, stirring at 2-6° C., and then stirring at 28-32° C. in the open round bottom flask to obtain the ligand-modified liposome.

Protein Corona Modified Nanometer Particle and Preparation Method

The present invention provides a protein corona modified nanometer particle, the protein corona modified nanometer particle comprises the nanometer particle of the present invention and/or the ligand-modified nanometer particle of the present invention; and a protein corona.

Preferably, the nanometer particle comprises perfluoropentane.

Preferably, the nanometer particle encapsulates perfluoropentane.

In a preferred embodiment, the protein of the protein corona comprises serum protein, plasma protein and/or tissue protein.

Preferably, the serum protein, plasma protein and/or tissue protein comprise human or non-human mammalian serum protein, plasma protein and/or tissue protein.

Preferably, the serum protein, plasma protein and/or tissue protein comprise in vitro or isolated serum protein, plasma protein and/or tissue protein.

In a preferred embodiment, the non-human mammal comprises mice, rat, rabbit, monkey, bovine, horse, sheep, dog, cat, orangutan or baboon.

Preferably, the bovine comprises fetal bovine.

Preferably, the serum and/or plasma comprises fetal bovine serum and/or fetal bovine plasma.

In a preferred embodiment, the protein corona modified nanometer particle comprises in vitro or isolated protein corona modified nanometer particle.

Preferably, the protein corona is modified on the the nanometer particle of the present invention and/or the ligand-modified nanometer particle of the present invention.

Preferably, the protein corona is modified on the surface of the nanometer particle of the present invention and/or the ligand-modified nanometer particle of the present invention.

Preferably, the surface comprises outer surface.

Preferably, the modification comprises physical modification and/or chemical modification.

Preferably, the modification comprises physical adsorption, chemical adsorption and/or coupling.

Preferably, the modification comprises adsorption.

The present invention provides a method for preparing the protein corona modified nanometer particle of the present invention, which comprises the following steps:

contacting the nanometer particle of the present invention and/or the ligand-modified nanometer particle of the present invention with the protein to obtain the protein corona modified nanometer particle.

Preferably, the method is in vitro method or in vivo method.

Preferably, the method is non-diagnostic and non-therapeutic method.

Preferably, the contacting is in vitro or in vivo contacting.

Preferably, the contacting is performed in protein-containing condition.

Preferably, the protein-containing condition comprises blood, serum, plasma and/or culture medium.

In a preferred embodiment, the contacting is performed in culture medium.

Preferably, the culture medium comprises liquid culture medium.

Preferably, the culture medium comprises cell culture medium.

Preferably, the culture medium comprises protein-containing medium.

Preferably, the culture medium comprises protein.

Preferably, the protein comprises serum protein, plasma protein and/or tissue protein.

Preferably, the culture medium comprises serum protein, plasma protein and/or tissue protein.

Preferably, the serum protein, plasma protein and/or tissue protein comprise in vitro or isolated serum protein, plasma protein and/or tissue protein.

Preferably, the culture medium comprises serum, plasma and/or tissue protein-containing culture medium.

Preferably, the culture medium comprises serum-containing culture medium.

Preferably, the serum comprises fetal bovine serum.

Preferably, the plasma comprises fetal bovine plasma.

Preferably, the volume fraction of the serum is 5-15%, preferably 8-12%, more preferably 10% in the serum-containing culture medium.

Preferably, the culture comprises in vitro culture.

In a preferred embodiment, the serum, plasma and/or tissue protein comprises human or non-human mammalian serum, plasma and/or tissue proteins.

Preferably, the contacting is performed in the blood, serum or plasma.

Preferably, the blood, serum or plasma comprises in vitro or isolated blood, serum or plasma.

Preferably, the blood, serum or plasma comprises human or non-human mammalian blood, serum or plasma.

Preferably, the non-human mammal comprises mice, rat, rabbit, monkey, bovine, horse, sheep, dog, cat, orangutan or baboon.

Preferably, the bovine comprises fetal bovine.

Preferably, the contacting time is 0.25-6 h, preferably 0.25-4 h, more preferably 0.25-2 h, more preferably 0.25-1 h, more preferably 0.25-0.5 h, such as 0.5-1 h.

Method for Removing Protein Corona of the Protein Corona Modified Nanometer Particle The present invention provides a method for removing protein corona of protein corona modified nanometer particle, which comprises the following steps:

subjecting the protein corona modified nanometer particle to ultrasound stimulation to remove the protein corona of the protein corona modified nanometer particle.

Ultrasound stimulation can remove the protein corona on the surface of nanometer particle, so the masking effect of the protein corona on the ligand modified on the surface of nanometer particle can be overcome, and the binding of ligand modified on the surface of nanometer particle to the receptor of target cell (e.g., tumor vascular cell or tumor cell) is recovered, thus enhancing the uptake of the ligand-modified nanometer particle by cell.

Preferably, the nanometer particle comprises perfluoropentane.

Preferably, the nanometer particle encapsulates perfluoropentane.

Preferably, the method is in vitro method or in vivo method.

Preferably, the method comprises non-therapeutic and/or non-diagnostic method.

In a preferred embodiment, the removing comprises decreasing, reducing or eliminating.

Preferably, the decreasing comprises the decreasing of protein content.

Preferably, the decreasing protein corona comprises the decreasing of protein content in protein corona.

Preferably, the reducing comprises the reducing of protein content.

Preferably, the reducing protein corona comprises the reducing of protein content in protein corona.

In a preferred embodiment, the subjecting is performed in protein-free condition.

In a preferred embodiment, the subjecting comprises subjecting in protein-free condition.

In a preferred embodiment, the protein corona modified nanometer particle comprises the protein corona modified nanometer particle in protein-free condition.

Preferably, the method comprises the following steps:

subjecting the protein corona modified nanometer particle to ultrasound stimulation to remove the protein corona of the protein corona modified nanometer particle in protein-free condition.

Preferably, the protein-free condition comprises physiological saline, PBS buffer solution or serum-free culture medium.

In a preferred embodiment, the subjecting is performed in protein-containing condition.

Preferably, the subjecting comprises subjecting in protein-containing condition.

In a preferred embodiment, the protein corona modified nanometer particle comprises protein corona modified nanometer particle in protein-containing condition.

Preferably, the method comprises the following steps:

subjecting the protein corona modified nanometer particle to ultrasound stimulation to remove the protein corona of the protein corona modified nanometer particle in protein-containing condition.

Preferably, the protein-containing condition comprises blood, serum, plasma, and/or culture medium.

Preferably, the protein corona modified nanometer particle comprises protein corona modified nanometer particle in blood, serum or plasma.

Preferably, the blood, serum or plasma comprises in vitro or isolated blood, serum or plasma.

Preferably, the blood, serum or plasma comprises human or non-human mammal blood, serum or plasma.

Preferably, the protein corona modified nanometer particle comprises the protein corona modified nanometer particle in culture medium.

Preferably, the protein of the protein corona comprises serum protein, plasma protein and/or tissue protein.

In a preferred embodiment, the serum protein, plasma protein and/or tissue protein comprise in vitro or isolated serum protein, plasma protein and/or tissue protein.

In a preferred embodiment, the serum protein, plasma protein and/or tissue protein comprise the human or non-human mammal serum protein, plasma protein and/or tissue protein.

Preferably, the non-human mammal comprises mice, rat, rabbit, monkey, bovine, horse, sheep, dog, cat, orangutan or baboon.

Preferably, the bovine comprises fetal bovine.

Preferably, the serum comprises fetal bovine serum.

Preferably, the plasma comprises fetal bovine plasma.

In a preferred embodiment, the culture medium comprises fluid culture medium.

In a preferred embodiment, the culture medium comprises cell culture medium.

Preferably, the culture medium comprises protein-containing medium.

Preferably, the culture medium comprises protein.

Preferably, the protein comprises serum protein, plasma protein and/or tissue protein.

Preferably, the culture medium comprises serum protein, plasma protein and/or tissue protein.

Preferably, the culture medium comprises serum, plasma and/or tissue protein-containing culture medium.

Preferably, the culture medium comprises serum-containing culture medium.

Preferably, the volume fraction of the serum is 5-15%, preferably 8-12%, more preferably 10% in the serum-containing culture medium.

In a preferred embodiment, the cell comprise tumor cell and/or tumor vascular cell.

Preferably, the tumor vascular cell comprises tumor vascular endothelial cell.

Preferably, the tumor vascular cell comprises ECDHCC cell.

In a preferred embodiment, the cell comprises the cell that need to be cultured or grown in protein-containing condition.

In a preferred embodiment, the cell comprises the cell that need to be cultured or grown in serum-containing medium.

Preferably, the cell comprises the cell that need to be cultured in serum-containing medium.

Preferably, the culture comprises in vitro culture.

Ultrasound stimulation can effectively remove the protein corona of the protein corona modified nanometer particle. As for cell that is need to be cultured in the protein-containing medium (e.g., serum-containing medium), ultrasound stimulation can overcome the masking effect of the protein corona on the ligand modified on the surface of nanometer particle, and avoid the protein corona blocking the binding of the ligand modified on the surface of nanometer particle to cell receptor in the protein-containing condition (e.g., serum-containing medium), thus accurately determining whether the ligand to be tested modified on the surface of nanometer particle can bind to the cell or cell surface receptor, and then accurately screening or identifying the potential ligand targeting at the cell or cell surface receptor to avoid false negative results, especially in the condition with low amount of ligand to be tested.

Screening or Identifying Potential Ligand Targeting Cell or Cell Surface Receptor The present invention provides a method for screening or identifying potential ligand targeting cell or cell surface receptor, which comprises the following steps:

(I) modifying the ligand on the nanometer particle to obtain ligand-modified nanometer particle;

(II) incubating the cell or cell surface receptor with the ligand-modified nanometer particle in the step (I) and then conducting ultrasound stimulation, and determining the binding of the ligand-modified nanometer particle in step (I) or the ligand of the ligand-modified nanometer particle in the step (I) to the cell or cell surface receptor, thereby screening or identifying whether the ligand in the step (I) is potential ligand targeting the cell or cell surface receptor.

Preferably, the cell surface receptor comprises receptor on the surface of cell membrane.

Preferably, the cell surface receptor comprises receptor on the outer surface of cell membrane.

Preferably, the nanometer particle comprises perfluoropentane.

Preferably, the nanometer particle encapsulates perfluoropentane.

Preferably, the nanometer particle is as described above.

Preferably, the ligand-modified nanometer particle in the step (I) is as described above.

Preferably, the ligand in the step (I) comprises ligand to be tested.

In a preferred embodiment, the step (II) comprises.

(II) incubating the cell or cell surface receptor with the ligand-modified nanometer particle in the step (I) and then conducting ultrasound stimulation, and determining whether the ligand-modified nanometer particle in step (I) or the ligand of the ligand-modified nanometer particle in the step (I) binds to the cell or cell surface receptor, thereby screening or identifying whether the ligand in the step (I) is potential ligand targeting the cell or cell surface receptor.

Preferably, in the step (II), if the ligand-modified nanometer particle in step (I) or the ligand of the ligand-modified nanometer particle in step (I) binds to the cell or cell surface receptor, the ligand in the step (I) is potential ligand targeting the cell or cell surface receptor.

Preferably, in the step (II), if the ligand-modified nanometer particle in step (I) or the ligand of the ligand-modified nanometer particle in step (I) does not bind to the cell or cell surface receptor, the ligand in the step (I) is not potential ligand targeting the cell or cell surface receptor.

In a preferred embodiment, the method further comprises setting a control group, the control group comprises a nanometer particle without ligand modification, and determining the binding of the nanometer particle without ligand modification to the cell or cell surface receptor.

Preferably, the method further comprises setting a control group, the control group comprises a nanometer particle without ligand modification and the other conditions are the same to those of the ligand-modified nanometer particle, and determining the binding of the nanometer particle without ligand modification to the cell or cell surface receptor.

In a preferred embodiment, if the binding force B1 of the ligand-modified nanometer particle or the ligand of the ligand-modified nanometer particle to the cell or cell surface receptor is greater than the binding force B0 of the nanometer particle without ligand modification to the cell or cell surface receptor, the ligand in the step (I) is potential ligand targeting the cell or cell surface receptor.

In a preferred embodiment, the step (II) comprises:

(II-1) in the test group, incubating the cell or cell surface receptor with the ligand-modified nanometer particle in the step (I) and then conducting ultrasound stimulation, and determining the binding force B1 of the ligand-modified nanometer particle in step (I) or the ligand of the ligand-modified nanometer particle in the step (I) to the cell or cell surface receptor; and setting a control group, the control group comprises a nanometer particle without ligand modification and the other conditions are the same to those of the test group, and determining the binding force B0 of the nanometer particle without ligand modification to the cell or cell surface receptor (II-2) if the binding force B1 of the ligand-modified nanometer particle in the step (I) or the ligand of the ligand-modified nanometer particle in the step (I) to the cell or cell surface receptor is greater than the binding force B0 of the nanometer particle without ligand modification to the cell or cell surface receptor, the ligand in the step (I) is potential ligand targeting the cell or cell surface receptor.

Preferably, if the binding force B1 of the ligand-modified nanometer particle in the step (I) or the ligand of the ligand-modified nanometer particle in the step (I) to the cell or cell surface receptor is similar to the binding force B0 of the nanometer particle without ligand modification to the cell or cell surface receptor, the ligand in the step (I) is not potential ligand targeting the cell or cell surface receptor.

In a preferred embodiment, the targeting comprises specific targeting or non-specific targeting.

Preferably, the "greater than" comprises significantly greater than.

Preferably, the "greater than" comprises significantly greater than with statistically significant.

Preferably, "greater than" means the ratio (B1/B0) of the binding force B1 of the ligand-modified nanometer particle or the ligand of the ligand-modified nanometer particle to the cell or cell surface receptor to the binding force B0 of the nanometer particle without ligand modification to the cell or cell surface receptor is ≥1.0, preferably ≥1.2, more preferably ≥1.5, more preferably ≥2, more preferably ≥3, more preferably ≥5, more preferably ≥10, more preferably ≥15, more preferably ≥20, more preferably ≥30, more preferably ≥50, more preferably ≥80, more preferably ≥100, more preferably ≥150, more preferably ≥200, more preferably ≥500, more preferably ≥1000, more preferably ≥5000, more preferably ≥10000.

Preferably, the B1/B0 is 1.5-10,000, preferably 2-500, more preferably 2-200, more preferably 2-100, more preferably 2-50, more preferably 5-30.

Preferably, the "greater than" means that the binding force B1 of the ligand-modified nanometer particle or the ligand of the ligand-modified nanometer particle to the cell or cell surface receptor in the test group with biological replicates is greater than the binding force B0 of the nanometer particle without ligand modification to the cell or cell surface receptor in the control group with biological replicates, and the p value is <0.05 in t test.

In a preferred embodiment, the ligand comprises peptide ligand or protein ligand.

In a preferred embodiment, the receptor comprise protein receptor, lipoprotein receptor or glycoprotein receptor.

In a preferred embodiment, the binding comprises affinity.

Preferably, the binding force comprises affinity force.

In a preferred embodiment, the ligand comprises potential ligand.

In a preferred embodiment, the ligand-modified nanometer particle comprise in vitro or isolated ligand-modified nanometer particle.

In a preferred embodiment, the cell or cell surface receptor comprises in vitro or isolated cell or cell surface receptor.

In a preferred embodiment, the method comprises in vitro method or in vivo method.

In a preferred embodiment, the method comprises non-therapeutic and/or non-diagnostic method.

In a preferred embodiment, the incubating comprises in vitro or in vivo incubating.

Preferably, the in vivo comprises in vivo in human or non-human mammal.

In a preferred embodiment, the incubating comprises incubating in protein-containing condition.

Preferably, the incubating is performed in protein-containing condition.

Preferably, in the step (II), the incubating comprises incubating in protein-containing condition.

Preferably, in the step (II), the incubating is performed in protein-containing condition.

Preferably, the step (II) comprises:

incubating the cell or cell surface receptor with the ligand-modified nanometer particle in the step (I) in protein-containing condition and then conducting ultrasound stimulation, and determining the binding of the ligand-modified nanometer particle in step (I) or the ligand of the ligand-modified nanometer particle in the step (I) to the cell or cell surface receptor, thereby screening or identifying whether the ligand in the step (I) is potential ligand targeting the cell or cell surface receptor.

In a preferred embodiment, the incubating comprises incubating the cell or cell surface receptor with the ligand-modified nanometer particle in the step (I) in protein-containing condition.

Preferably, the condition comprises in vivo condition or in vitro condition.

In a preferred embodiment, the cell comprises the cell that need to be cultured or grown in protein-containing condition.

Preferably, the cell comprises the cell that need to be cultured or grown in serum-containing medium.

Preferably, the cell comprises the cell that need to be cultured in serum-containing medium.

Preferably, the culture comprises in vitro culture.

In a preferred embodiment, the protein-containing condition comprises blood, serum, plasma, tissue microenvironment and/or culture medium.

Preferably, the blood, serum or plasma comprises in vitro or isolated blood, serum or plasma.

Preferably, the blood, serum or plasma comprises human or non-human mammalian blood, serum or plasma.

In a preferred embodiment, the protein comprises serum protein, plasma protein and/or tissue protein.

In a preferred embodiment, the serum protein, plasma protein and/or tissue protein comprise in vitro or isolated serum protein, plasma protein and/or tissue protein.

Preferably, the serum protein, plasma protein and/or tissue protein comprise human or non-human mammalian serum protein, plasma protein and/or tissue protein.

Preferably, the non-human mammal comprises mice, rat, rabbit, monkey, bovine, horse, sheep, dog, cat, orangutan or baboon.

Preferably, the bovine comprises fetal bovine.

Preferably, the serum comprises fetal bovine serum.

Preferably, the plasma comprises fetal bovine plasma.

In a preferred embodiment, the culture medium comprises fluid culture medium.

In a preferred embodiment, the culture medium comprises cell culture medium.

In a preferred embodiment, the culture medium comprises protein-containing medium.

In a preferred embodiment, the culture medium comprises protein.

In a preferred embodiment, the culture medium comprises serum protein, plasma protein and/or tissue protein.

In a preferred embodiment, the culture medium comprises serum, plasma and/or tissue protein-containing culture medium.

Preferably, the culture medium comprises serum-containing culture medium.

Preferably, the volume fraction of the serum is 5-15%, preferably 8-12%, more preferably 10% in the serum-containing culture medium.

In a preferred embodiment, the incubating comprises incubating the cell or cell surface receptor with the ligand-modified nanometer particle in the step (I) in serum, plasma and/or tissue protein-containing culture medium.

In a preferred embodiment, the incubating comprises incubating the cell or cell surface receptor with the ligand-modified nanometer particle in the step (I) in serum-containing culture medium.

In a preferred embodiment, the ligand comprises ligand targeting cell or cell surface receptor.

In a preferred embodiment, the cell comprise tumor cell and/or tumor vascular cell.

Preferably, the tumor vascular cell comprises tumor vascular endothelial cell.

In a preferred embodiment, the binding comprises specific binding or non-specific binding.

In a preferred embodiment, the receptor comprises receptor on the outer surface of cell membrane.

In a preferred embodiment, the binding is measured by isotope disappearance assay, fluorescein assay, flow cytometry assay and/or transwell migration assay.

Preferably, the nanometer particle and/or the ligand is labeled with isotopes and/or fluorescein.

Preferably, the fluorescein comprises FITC (Fluorescein isothiocyanate), Cyanine 5 (Cy5), and/or Cyanine 5.5 (Cy5.5).

In a preferred embodiment, the binding mediates the uptake of the ligand-modified nanometer particle by the cell.

In a preferred embodiment, the binding mediates the endocytosis of the ligand-modified nanometer particle by the cell.

In a preferred embodiment, the binding mediates the endocytosis and exocytosis of the ligand-modified nanometer particle by the cell.

In a preferred embodiment, the binding is measured by determining the uptake efficiency of the ligand-modified nanometer particle in the step (I) by the cell.

Preferably, the cell does not have ability to uptake the nanometer particle without ligand modification in the control group.

In a preferred embodiment, the screening or identifying whether the ligand in the step (I) is potential ligand targeting the cell or cell surface receptor comprises:

if the uptake efficiency of the ligand-modified nanometer particle in the step (I) by the cell is greater than the uptake efficiency of the nanometer particle without ligand modification in the control group by the cell, the ligand in the step (I) is potential ligand targeting the cell or cell surface receptor.

In a preferred embodiment, the binding is measured by determining the endocytosis ability of the ligand-modified nanometer particle in the step (I) by the cell.

Preferably, the cell does not have endocytosis ability of the nanometer particle without ligand modification in the control group.

In a preferred embodiment, the screening or identifying whether the ligand in the step (I) is potential ligand targeting the cell or cell surface receptor comprises:

if the endocytosis ability of the ligand-modified nanometer particle in the step (I) by the cell is greater than the endocytosis ability of the nanometer particle without ligand modification in the control group by the cell, the ligand in the step (I) is potential ligand targeting the cell or cell surface receptor.

In a preferred embodiment, the binding is measured by determining the endocytosis and exocytosis ability of the ligand-modified nanometer particle in the step (I) by the cell.

Preferably, the cell does not have endocytosis and exocytosis ability of the nanometer particle without ligand modification in the control group.

In a preferred embodiment, the screening or identifying whether the ligand in the step (I) is potential ligand targeting the cell or cell surface receptor comprises:

if the endocytosis and exocytosis ability of the ligand-modified nanometer particle in the step (I) by the cell is greater than the endocytosis and exocytosis ability of the nanometer particle without ligand modification in the control group by the cell, the ligand in the step (I) is potential ligand targeting the cell or cell surface receptor.

In a preferred embodiment, the ligand in the step (I) comprises ligand mediating endocytosis of the ligand-modified nanometer particle by the cell.

Preferably, the ligand can mediate endocytosis of the ligand-modified nanometer particle by cell after the ligand-modified nanometer particle or the ligand of the ligand-modified nanometer particle binds to the cell or cell surface receptor.

In a preferred embodiment, the screening or identifying whether the ligand in the step (I) is potential ligand targeting the cell or cell surface receptor comprises:

if the ligand can mediate endocytosis of the ligand-modified nanometer particle by cell after the ligand-modified nanometer particle or the ligand of the ligand-modified nanometer particle binds to the cell or cell surface receptor, the ligand in the step (I) is potential ligand targeting the cell or cell surface receptor.

In a preferred embodiment, the ligand in the step (I) comprises ligand mediating endocytosis and exocytosis of the ligand-modified nanometer particle by the cell.

Preferably, the ligand can mediate endocytosis and exocytosis of the ligand-modified nanometer particle by cell after the ligand-modified nanometer particle or the ligand of the ligand-modified nanometer particle binds to the cell or cell surface receptor.

In a preferred embodiment, the screening or identifying whether the ligand in the step (I) is potential ligand targeting the cell or cell surface receptor comprises:

if the ligand can mediate endocytosis and exocytosis of the ligand-modified nanometer particle by cell after the ligand-modified nanometer particle or the ligand of the ligand-modified nanometer particle binds to the cell or cell surface receptor, the ligand in the step (I) is potential ligand targeting the cell or cell surface receptor.

In a preferred embodiment, the ligand can mediate endocytosis of the ligand-modified nanometer particle in the blood by tumor vascular cell after the ligand-modified nanometer particle or the ligand of the ligand-modified nanometer particle binds to the tumor vascular cell or tumor vascular cell surface receptor, then the ligand-modified nanometer particle is exocytosed to extravascular of tumor (e.g., tumor tissue microenvironment).

In a preferred embodiment, the screening or identifying whether the ligand in the step (I) is potential ligand targeting the cell or cell surface receptor comprises:

if the ligand can mediate endocytosis of the ligand-modified nanometer particle in the blood by tumor vascular cell after the ligand-modified nanometer particle or the ligand of the ligand-modified nanometer particle binds to the tumor vascular cell or tumor vascular cell surface receptor, then the ligand-modified nanometer particle is exocytosed to extravascular of tumor (e.g., tumor tissue microenvironment), the ligand in the step (I) is potential ligand targeting the cell or cell surface receptor.

In a preferred embodiment, the method for measuring the binding or binding force of the ligand-modified nanometer particle or the ligand of the ligand-modified nanometer particle in the step (I) to the cell or cell surface receptor comprises:

if tumor vascular cell can endocytose the ligand-modified nanometer particle in the blood, then the ligand-modified nanometer particle is exocytosed to extravascular of tumor (e.g., tumor tissue microenvironment), the ligand can bind to cell or cell surface receptor.

Preferably, the tumor vascular cell cannot endocytose the nanometer particle without ligand modification in the blood circulation.

In a preferred embodiment, the ligand comprises ligand targeting receptor on the surface of tumor vascular cell.

In a preferred embodiment, the ligand comprises the ligand targeting the receptor on the surface of tumor cell.

Preferably, the surface comprises outer surface.

In a preferred embodiment, the ligand can mediate the penetration of the ligand-modified nanometer particle from tumor vessel into tumor site.

In a preferred embodiment, the ligand can mediate the penetration of the ligand-modified nanometer particle from tumor vessel into tumor site via endocytosis and exocytosis.

In a preferred embodiment, the ligand can target tumor vascular endothelial cell and mediate the endocytosis and exocytosis of the ligand-modified nanometer particle by tumor vascular endothelial cell.

In a preferred embodiment, the ligand comprises ligand mediating uptake of the ligand-modified nanometer particle by cell.

In a preferred embodiment, the ligand comprises ligand mediating endocytosis of the ligand-modified nanometer particle by cell.

In a preferred embodiment, the ligand comprises ligand mediating endocytosis and exocytosis of the ligand-modified nanometer particle by cell.

In a preferred embodiment, the ligand can mediate endocytosis of the ligand-modified nanometer particle in the blood by tumor vascular cell, then mediate exocytosis of the ligand-modified nanometer particle into extravascular of tumor (e.g., tumor tissue microenvironment).

Preferably, the incubated mixture of the cell or cell surface receptor and the ligand-modified nanometer particle is conducted ultrasound stimulation.

Use

The present invention provides a use of the nanometer particle of the present invention and/or the ligand-modified nanometer particle of the present invention in the preparation of a composition for the prevention and/or treatment of disease.

In a preferred embodiment, the nanometer particle is drug-loaded nanometer particle.

Preferably, the nanometer particle is drug-loaded nanometer particle or drug-loaded liposome.

In a preferred embodiment, the disease is an indication disease of the drug

In a preferred embodiment, the drug comprises anticancer drug.

In a preferred embodiment, the disease comprises tumor.

In a preferred embodiment, the composition is a pharmaceutical composition.

In a preferred embodiment, the pharmaceutical composition further comprises a pharmaceutically acceptable carrier.

In a preferred embodiment, the composition comprises but is not limited to solid preparation, liquid preparation or semi-solid preparation.

In a preferred embodiment, the composition comprises but is not limited to injection preparation, oral preparation or external preparation.

Preferably, the injection preparation comprises but is not limited to intravascular injection preparation.

In a preferred embodiment, the injection preparation comprises but is not limited to intravenous injection preparation, arterial injection preparation, intratumoral injection preparation, tumor intravascular injection preparation or tumor microenvironment injection preparation.

In a preferred embodiment, the treatment comprises inhibition, alleviation, relief, reversal or eradication.

The present invention further provides a method for preventing and/or treating disease, which comprises administering the nanometer particle of the present invention and/or the ligand-modified nanometer particle of the present invention to a subject in need, thereby preventing and/or treating disease.

In a preferred embodiment, the nanometer particle is drug-loaded nanometer particle.

Preferably, the nanometer particle is drug-loaded nanometer particle or drug-loaded liposome.

In a preferred embodiment, the subject comprises human and non-human mammal.

In a preferred embodiment the disease is an indication disease of the drug.

Preferably, the disease comprises tumor.

In a preferred embodiment, the drug comprises anticancer drug.

In a preferred embodiment, an ultrasound stimulation is carried out on the lesion site (e.g., tumor site) during the administration of the nanometer of the present invention and/or the ligand-modified nanometer particle of the present invention to a subject in need.

In a preferred embodiment, the administration comprises but is not limited to injection administration, oral administration or external administration.

In a preferred embodiment, the injection administration comprises but is not limited to intravenous injection administration, arterial injection administration, intratumoral injection administration, tumor intravascular injection administration or tumor microenvironment injection administration.

Preferably, the injection administration comprises but is not limited to intravascular injection administration.

The present invention further provides a use of the nanometer particle of the present invention in the preparation of a carrier for screening or identifying potential ligand targeting cell or cell surface receptor.

In a preferred embodiment, the method for screening or identifying potential ligand targeting cell or cell surface receptor comprises:

(I) modifying the ligand on the nanometer particle to obtain ligand-modified nanometer particle;

(II) incubating the cell or cell surface receptor with the ligand-modified nanometer particle in the step (I) and then conducting ultrasound stimulation, and determining the binding of the ligand-modified nanometer particle in step (I) or the ligand of the ligand-modified nanometer particle in the step (I) to the cell or cell surface receptor, thereby screening or identifying whether the ligand in the step (I) is potential ligand targeting the cell or cell surface receptor.

In a preferred embodiment, the cell surface receptor comprises receptor on the surface of cell membrane.

In a preferred embodiment, the cell surface receptor comprises receptor on the outer surface of cell membrane.

In a preferred embodiment, the receptor comprises protein receptor, lipoprotein receptor or glycoprotein receptor.

The present invention further provides a use of ultrasound instrument for preparing an apparatus, the apparatus is used for:

(a) removing protein corona of the protein corona modified nanometer particle by ultrasound stimulation;

(b) screening or identifying potential ligand targeting cell or cell surface receptor;

(c) enhancing the ligand-modified nanometer particle to treat disease by performing an ultrasound stimulation on the lesion site (e.g., tumor site); and/or (d) improving the lysosome retention and/or degradation of nanometer particle, ligand-modified nanometer particle and/or protein corona modified nanometer particle by ultrasound stimulation.

Preferably, the nanometer particle, ligand-modified nanometer particle and/or protein corona modified nanometer particle is as described above.

Preferably, the nanometer particle encapsulates perfluoropentane.

In a preferred embodiment, the (a) comprises removing protein corona of the protein corona modified nanometer particle by ultrasound stimulation to improve the efficacy of the nanometer particle.

In a preferred embodiment, the (a) removing protein corona of the protein corona modified nanometer particle by ultrasound stimulation comprises:

subjecting the protein corona modified nanometer particle to ultrasound stimulation to remove the protein corona of the protein corona modified nanometer particle.

In a preferred embodiment, the cell surface receptor comprises receptor on the surface of cell membrane.

In a preferred embodiment, the cell surface receptor comprises receptor on the outer surface of cell membrane.

In a preferred embodiment, the (d) improving the lysosome retention and/or degradation of nanometer particle, ligand-modified nanometer particle and/or protein corona modified nanometer particle by ultrasound stimulation comprises:

contacting the cell with the nanometer particle, ligand-modified nanometer particle and/or protein corona modified nanometer particle and then conducting ultrasound stimulation to improve the lysosome retention and/or degradation of nanometer particle, ligand-modified nanometer particle and/or protein corona modified nanometer particle.

Preferably, the method is in vitro method or in vivo method.

Preferably, the method is non-diagnostic and non-therapeutic method.

Preferably, the contacting is in vivo contacting or in vitro contacting.

In a preferred embodiment, the contacting comprises contacting in protein-containing condition.

In a preferred embodiment, the contacting comprises contacting in serum-containing medium.

In a preferred embodiment, the cell comprises the cell that need to be cultured or grown in protein-containing condition.

Preferably, the cell comprises the cell that need to be cultured or grown in serum-containing medium.

Preferably, the cell comprises the cell that need to be cultured in serum-containing medium.

In a preferred embodiment, the nanometer particle comprises drug-loaded nanometer particle.

In a preferred embodiment, the drug is antitumor drug.

In a preferred embodiment, the disease is an indication disease of the drug.

In a preferred embodiment, the cell comprise tumor cell and/or tumor vascular cell.

Preferably, the tumor vascular cell comprise tumor vascular endothelial cell.

Preferably, the tumor vascular cell comprises ECDHCC cell.

Preferably, the disease comprises tumor.

Preferably, the tumor is as described above.

In a preferred embodiment, the administration comprises but is not limited to injection administration, oral administration or external administration.

Preferably, the injection administration comprises but is not limited to intravenous injection administration, arterial injection administration, intratumoral injection administration, tumor intravascular injection administration or tumor microenvironment injection administration.

Preferably, the injection administration comprises but is not limited to intravascular injection administration.

In a preferred embodiment, the improving comprises avoiding or overcoming.

In a preferred embodiment, the degradation comprises degradation by lysosomal enzyme.

Method for Inhibiting Cell

The present invention provides a method for inhibiting cell, which can be used to study the inhibition mechanism of inhibitor.

In a preferred embodiment, the method for inhibiting cell comprises:

contacting the cell with the nanometer particle of the present invention and/or the ligand-modified nanometer particle of the present invention and then conducting ultrasound stimulation to inhibit the cell.

In a preferred embodiment, the method is in vitro method or in vivo method.

In a preferred embodiment, the nanometer particle comprises drug-loaded nanometer particle.

In a preferred embodiment, the method comprises a method for enhancing the ligand-modified nanometer particle to inhibit cell.

In a preferred embodiment, the method is non-diagnostic and non-therapeutic method.

In a preferred embodiment, the ligand comprises ligand targeting cell or cell surface receptor.

Preferably, the contacting is performed in protein-containing condition.

In a preferred embodiment, the method comprises:

contacting the cell with the nanometer particle of the present invention and/or the ligand-modified nanometer particle of the present invention in protein-containing condition and then conducting ultrasound stimulation to inhibit the cell.

In a preferred embodiment, the cell comprises the cell that need to be cultured or grown in protein-containing condition.

In a preferred embodiment, the ligand comprises ligand mediating uptake of the ligand-modified nanometer particle by cell.

In a preferred embodiment, the ligand comprises ligand mediating endocytosis of the ligand-modified nanometer particle by cell.

Preferably, the ligand comprises RGD peptide and/or an NGR peptide.

In a preferred embodiment, the cell comprise tumor cell and/or tumor vascular cell.

Preferably, the tumor vascular cell comprises tumor vascular endothelial cell.

Preferably, the tumor vascular cell comprises ECDHCC cell.

In a preferred embodiment, the drug comprises cell inhibitor.

Preferably, the drug comprises anti-tumor drug.

In a preferred embodiment, the contacting is performed in protein-containing condition.

In a preferred embodiment, the contacting comprises contacting in protein-containing condition.

In a preferred embodiment, the cell comprises the cell that need to be cultured or grown in protein-containing condition.

Preferably, the cell comprises the cell that need to be cultured or grown in serum-containing medium.

Preferably, the cell comprises the cell that need to be cultured in serum-containing medium.

In a preferred embodiment, the protein-containing condition comprises blood, serum, plasma and/or culture medium.

Preferably, the blood, serum or plasma comprise in vitro or isolated blood, serum or plasma.

Preferably, the blood, serum or plasma comprises human or non-human mammalian blood, serum or plasma.

Preferably, the non-human mammal comprises mice, rat, rabbit, monkey, bovine, horse, sheep, dog, cat, orangutan or baboon.

Preferably, the bovine comprises fetal bovine.

In a preferred embodiment, the culture medium comprises fluid culture medium.

In a preferred embodiment, the culture medium comprises cell culture medium.

In a preferred embodiment, the culture medium comprises protein.

Preferably, the protein comprises serum protein, plasma protein and/or tissue protein.

Preferably, the serum protein, plasma protein and/or tissue protein comprise in vitro or isolated serum protein, plasma protein and/or tissue protein.

Preferably, the serum protein, plasma protein and/or tissue protein comprise human or non-human mammalian serum protein, plasma protein and/or tissue protein.

In a preferred embodiment, the culture medium comprises serum, plasma and/or tissue protein-containing culture medium.

Preferably, the culture medium comprises serum-containing culture medium.

In a preferred embodiment, the volume fraction of the serum is 5-15%, preferably 8-12%, more preferably 10% in the serum-containing culture medium.

Preferably, the serum comprises fetal bovine serum.

Preferably, the plasma comprises fetal bovine plasma.

In a preferred embodiment, the contacting comprises in vitro contacting.

In a preferred embodiment, the culture comprises in vitro culture.

In a preferred embodiment, the surface of the nanometer particle comprises protein corona in the culture medium under no ultrasound stimulation treatment.

Preferably, the protein corona is adsorbed on the surface of the nanometer particle.

Preferably, the ligand can mediate the uptake of the ligand modified nanometer particle by cell after binding to cell or cell surface receptor.

Preferably, the ligand can mediate the endocytosis of the ligand modified nanometer particle by cell after binding to cell or cell surface receptor.

In a preferred embodiment, the surface of the nanometer particle comprises protein corona in the culture medium under no ultrasound stimulation treatment.

Preferably, the protein corona is adsorbed on the surface of the nanometer particle.

In a preferred embodiment, the binding of the ligand to the cell or cell surface receptor can mediate the uptake of the ligand-modified nanometer particle by the cell.

In a preferred embodiment, the ligand can bind to the the cell or cell surface receptor.

In a preferred embodiment, the binding of the ligand to the cell or cell surface receptor can mediate the endocytosis of the ligand-modified nanometer particle by the cell.

In a preferred embodiment, the cell surface receptor comprises receptor on the surface of cell membrane.

Preferably, the cell surface receptor comprises receptor on the outer surface of cell membrane.

Preferably, the receptor comprises protein receptor, lipoprotein receptor or glycoprotein receptor.

In a preferred embodiment, the incubated mixture of the cell and the nanometer particle or the ligand-modified nanometer particle is conducted ultrasound stimulation.

System or Device

The present invention provides a system or device, the system or device comprises the nanometer particle of the present invention and/or the ligand-modified nanometer particle of the present invention; and an ultrasound instrument.

In a preferred embodiment, the system or device further comprises a specification or label, the specification or label records that an ultrasound stimulation is carried out on the lesion site (e.g., tumor site) during the administration of the nanometer particle of the present invention and/or the ligand-modified nanometer particle of the present invention to a subject in need for the treatment of disease.

In a preferred embodiment, the nanometer particle is drug-loaded nanometer particle.

Preferably, the nanometer particle is drug-loaded nanoparticle or drug-loaded liposome.

In a preferred embodiment, the ultrasound instrument comprises ultrasonic device.

In a preferred embodiment, the subject comprises human and non-human mammal.

In a preferred embodiment, the disease is an indication disease of the drug

In a preferred embodiment, the drug comprises anticancer drug.

Preferably, the disease comprises tumor.

In a preferred embodiment, the administration comprises but is not limited to injection administration, oral administration or external administration.

Preferably, the injection administration can comprise but be not limited to intravenous injection administration, arterial injection administration, intratumoral injection administration, tumor intravascular injection administration or tumor microenvironment injection administration.

Preferably, the injection administration can comprise but be not limited to intravascular injection administration.

Composition

The composition of the present invention can comprise but be not limited to pharmaceutical composition.

The composition of the present invention can further comprises a pharmaceutically acceptable carrier. The term "pharmaceutically acceptable carrier" refers to one or more compatible solid or liquid fillers or gel materials, which are suitable for use in human and must have sufficient purity and sufficiently low toxicity. The "compatible" means each ingredient of the composition can be blended with each other without significantly reducing the efficacy. Some examples of the pharmaceutically acceptable carriers are cellulose and its derivatives (e.g. sodium carboxymethylcellulose, ethylcellulose, cellulose acetate, etc.), gelatin, talc, solid lubricants (e.g. stearic acid, magnesium stearate), calcium sulfate, plant oil (e.g. soybean oil, sesame oil, peanut oil, olive oil, etc.), polyols (e.g. propylene glycol, glycerin, mannitol, sorbitol, etc.), emulsifier (e.g. Tween®), wetting agent (e.g. sodium lauryl sulfate), colorant, flavoring agent, stabilizer, antioxidant, preservative, pyrogen-free water, etc.

The administration mode of the composition of the present invention has no special limitation. Representative mode of administration is injection administration, oral administration or external administration. Preferably, the injection administration comprises intravenous injection administration, arterial injection administration, intratumoral injection administration, tumor intravascular injection administration or tumor microenvironment injection administration.

The dosage form of the composition or preparation of the present invention is oral preparation, external preparation or injection preparation. Representatively, the solid dosage form used for oral administration comprises capsule, tablet, pill, powder and granule. In the solid dosage form, the active ingredient is mixed with at least one conventional inert excipient (or carrier), such as sodium citrate or dicalcium phosphate, or with the components as follows: (a) fillers or compatibilizers, such as starch, lactose, sucrose, glucose, mannitol and silicic acid; (b) binders, such as hydroxymethyl cellulose, alginate, gelatin, polyvinylpyrrolidone, sucrose and arabic gum; (c) humectants, such as glycerin; (d) disintegrants, such as agar, calcium carbonate, potato starch or cassava starch, alginic acid, some composite silicates, and sodium carbonate; (e) slow corrosion agents, such as paraffin; (f) absorption accelerators, such as quaternary amine compounds; (g) wetting agents, such as cetyl alcohol and glyceryl monostearate; (h) adsorbents, such as kaolin; and (i) lubricants, such as talc, calcium stearate, magnesium stearate, solid polyethylene glycol, sodium dodecyl sulfate, or mixtures thereof. In the capsule, tablet and pill, the dosage form can further contain a buffer.

The parenteral injection composition can comprise physiologically acceptable sterile aqueous or anhydrous solution, dispersion, suspension or emulsion, and sterile powders for redissolution into sterile injectable solution or dispersion. Suitable aqueous and non-aqueous carrier, diluent, solvent or excipient comprise water, ethanol, polyols and suitable mixtures thereof.

The dosage form of topical application or administration comprises ointment, powder, patch, spray and inhalation. The active ingredient can be mixed with physiologically acceptable carrier and any preservative, buffer or propellant under sterile condition.

The composition is administered by applying a safe and effective amount of the nanometer particle or liposome of the present application to a human or non-human animal (e.g., mice, rat, rabbit, monkey, bovine, horse, sheep, dog, cat, orangutan or baboon, etc.) in need, wherein the administration dose is a pharmaceutically acceptable effective amount. As used herein, the term "safe and effective amount" refers to an amount that has a function or activity in human and/or animal and is acceptable to human and/or animal. It should be understand in the art that the "safe and effective amount" can vary depending on the form of the pharmaceutical composition, the route of administration, the excipients of the drug, the severity of the disease, and the combination with other drugs, etc. For example, for a person with a body weight of 60 kg, the daily dose is usually 0.1 to 1000 mg, preferably 1 to 600 mg, more preferably 2 to 300 mg. Of course, the specific dose should also take into account the route of administration, the patient's health and other factors, which are within the skill range of skilled doctor.

The Main Advantages of the Present Invention Comprise:

1. The present invention develops a method for removing protein corona of the protein corona modified nanometer particle by ultrasound stimulation treatment. Ultrasound stimulation can overcome the masking effect of the protein corona on the ligand of the nanometer particle surface, recover the binding of the ligand modified on the surface of the nanometer particle to the receptor of target cell (e.g., tumor vascular cell or tumor cell), enhance the uptake of the nanometer particle by cell, promote the endocytosis and exocytosis of drug-loaded nanometer particle by tumor vascular endothelial cell via the binding of the ligand modified on the surface of the nanometer particle to the receptor on the surface of tumor vascular endothelial cell, promote the penetration of the ligand-modified nanometer particle from blood to tumor site through tumor vessel (especially tumor vessel with low permeability), and promote the uptake of the nanometer particle by tumor cell via ligand/receptor-mediated endocytosis, thus enhancing the antitumor effect of anti-tumor drug loaded in the nanometer particle.
2. The present invention develops a nanometer particle. After intravenous administration of the nanometer particle, ultrasound stimulation treatment on tumor site can significantly recover and enhance the binding of the ligand modified on the surface of the nanometer particle to the receptor on the surface of tumor vascular endothelial cell, promote the penetration of the ligand-modified nanometer particle from tumor vessel (especially tumor vessel with low permeability) to tumor site, and promote the uptake of the nanometer particle by tumor cell via ligand/receptor-mediated endocytosis, thus enhancing the antitumor effect of anti-tumor drug. In addition, the nanometer particle has excellent lysosomal escape ability to avoid lysosome retention and degradation under ultrasound stimulation treatment, lysosomal escape can effectively protect the nanometer particle and drug loaded in the nanometer particle from being damaged and degraded by lysosome enzyme, thus enhancing the stability of the nanometer particle and drug loaded in the nanometer particle in the cell and improving the therapeutic effect of drug. Furthermore, the nanometer particle of the present invention has excellent blood clearance half-life, good biocompatibility, high safety and little side effects.
3. Ultrasound stimulation can remove protein corona of the nanometer particle modified by ligand to be tested in protein-containing condition (e.g., serum-containing culture medium), overcome the masking effect of the protein corona on the ligand modified on the surface of the nanometer particle, and void the protein corona blocking the contacting of the ligand to be tested modified on the surface of the nanometer particle with cell receptor in the protein-containing condition (e.g., serum-containing medium), thus efficiently and accurately determining whether the ligand to be tested modified on the surface of the nanometer particle can bind to cell or cell surface receptor that need to be cultured or grown in protein-containing condition (e.g., serum-containing culture medium), and accurately screening or identifying potential ligand targeting cell or cell surface receptor to avoid false negative results, especially in the condition with low amount of ligand to be tested.

4. The present invention develops a method for screening or identifying potential ligand targeting cell or cell surface receptor. The cell or cell surface receptor can be incubated with the nanometer particle modified by the ligand to be tested in protein-containing condition (e.g., serum-containing culture medium) and then ultrasound stimulation is performed, ultrasound stimulation can effectively remove protein corona of the nanometer particle modified by the ligand to be tested, overcome the masking effect of the protein corona on the ligand to be tested modified on the surface of the nanometer particle, and void the protein corona blocking the contacting of the ligand to be tested modified on the surface of the nanometer particle with cell receptor in protein-containing condition (e.g., serum-containing medium), thus efficiently and accurately determining whether the ligand to be tested modified on the surface of the nanometer particle can bind to cell or cell surface receptor that need to be cultured or grown in protein-containing condition (e.g., serum-containing culture medium), and accurately screening or identifying whether the ligand to be tested is a potential ligand targeting cell or cell surface receptors. Therefore, the nanometer particle of the present invention can be used as a carrier for screening or identifying potential ligand targeting cell or cell surface receptor under ultrasound stimulation treatment. The method for screening or identifying potential ligand targeting cell or cell surface receptor is simple, the protein corona modified on the surface of the nanometer particle can be effectively removed by ultrasound stimulation treatment, thus overcoming the masking effect of the protein corona on the ligand to be tested modified on the surface of the nanometer particle, and effectively and accurately determining whether the ligand to be tested modified on the surface of the nanometer particle can bind to cell or cell surface receptor, particularly screening or identifying whether the ligand to be tested can target cell or cell surface receptor that need to be cultured or grown in protein-containing condition (e.g., serum-containing culture medium), thus accurately screening or identifying potential ligand targeting cell or cell surface receptor to avoid false negative results caused by the masking effect of protein corona on the ligand to be tested modified on the surface of the nanometer particle, especially in the condition with low amount of ligand to be tested.
5. The present invention provides a use of ultrasound instrument, the ultrasound stimulation can be used to remove protein corona of the protein corona modified nanometer particle, screen or identify potential ligand targeting cell or cell surface receptor, improve the lysosome retention and/or degradation of the nanometer particle, ligand-modified nanometer particle and/or protein corona modified nanometer particle, and enhance the ligand-modified nanometer particle to treat disease (e.g., tumor) by performing an ultrasound stimulation on the lesion site.

The present invention will be further illustrated below with reference to the specific examples. It should be understood that these examples give a detailed implementation mode and specific operation process based on the technical solution but are not to limit the scope of the invention

Example 1

1. Materials and Instruments

DPPC (1,2-dipalmitoyl-sn-glycero-3-phosphocholine) and DSPE-PEG2000 (1,2-distearoyl-sn-glycero-3-phosphoethanolamine-N-[methoxy (polyethylene glycol)-2000]) were purchased from Avanti Lipids Inc.

DSPE-PEG2000-RGD, Cyanine 5 (Cy5)-labeled DSPE-PEG2000 (DSPE-PEG2000$^{Cy5}$) and Cyanine 5.5 (Cy5.5)-labeled DSPE-PEG2000 (DSPE-PEG2000$^{Cy5}$-5) were purchased from Xi'an Ruixi Biological Technology Co. Ltd. DSPE-PEG2000-RGD was 1,2-distearoyl-sn-glycero-3-phosphoethanolamine-N-[methoxy (polyethylene glycol)-2000]-RGD targeting peptide, the amino acid sequence of RGD targeting peptide was Cys (cysteine)-Arg (arginine)-Gly (glycine)-Asp (aspartic acid)-Lys (lysine)-Gly (glycine)-Pro (proline)-Asp (aspartic acid)-Cys (cysteine) with the amino acid sequence CRGDKGPDC (SEQ ID NO: 1).

Chlorpromazine and cytochalasin D were purchased from Santa Cruz Biotechnology.

RPMI 1640 medium, DMEM medium, fetal bovine serum (FBS) and 0.25% trypsin solution were purchased from GIBCO (USA).

The serum-free medium was mainly consisted of water, glucose, amino acids and inorganic salts and did not contain protein components.

The serum-containing medium was a culture medium containing 10% (v/v) fetal bovine serum.

Alamar Blue Cell Viability Reagent, Hoechst 33342 and LysoTracker® Green DND 26 were purchased from Thermo Fisher Scientific Inc.

Ki67 antibody was purchased from Proteintech Group.

TUNEL Apoptosis Assay Kit was purchased from Roche.

Enhanced BCA Protein Assay Kit and Golgi-Tracker Green were purchased from Beyotime Biotechnology.

Matrigel basement membrane matrix was purchased from BD Biosciences.

EXO1 and gemcitabine prodrug CP4126 were purchased from Med-chem Express. gemcitabine prodrug CP4126, abbreviated as "CP4126", was gemcitabine elaidate with the structure as follows:

CP4126

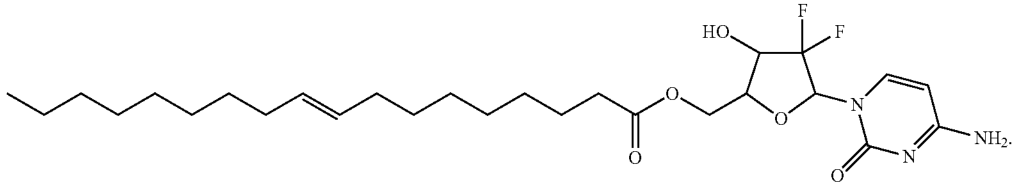

The ultrasound instrument was Mettler Sonicator-740.

Gemcitabine was abbreviated as GEM.

2. Cell and Animal Model

Human pancreatic ductal adenocarcinoma (PDA) cell line BxPC3, hepatocellular carcinoma (HCC) cell line Huh7, hepatocellular carcinoma-derived endothelial cell (ECDHCC) were purchased from American Type Culture Collection.

Male BALB/c nude mice (6-8 weeks) and male NOD/SCID mice (6-8 weeks) were supplied by the Laboratory Animal Center of Zhejiang Chinese Medical University. Mice were housed in approved animal-care facilities on a 12 h light/dark cycle and were free to food and water. The animal experiments were approved by the Animal Ethics Committee. The uses of clinical PDA and HCC patients' tumor specimens were approved by the Human Research Ethics Committees.

The BALB/c nude mice bearing human-derived tumor xenograft of PDA or HCC in the subcutaneous region were established by following procedures:

The clinical PDA or HCC tumor specimens were obtained from the patients diagnosed as PDA or HCC tumor without any radiation or chemical therapy before the surgery. In the sterile condition, the PDA or HCC tumor specimens were immediately washed with PBS and cut into small pieces (1×1×1 mm). The tumor pieces were dipped in the Matrigel basement membrane matrix and then transplanted into NOD/SCID mice subcutaneously on their right flanks. When the tumor diameter reached 6-8 mm, the NOD/SCID mice were sacrificed, and the tumor tissue were excised. Then, the tumor tissues were immediately washed with PBS and cut into small pieces (1×1×1 mm) for transplantation into BALB/c nude mice subcutaneously on their right or (and) left flanks or beside the abdominal blood vessel. Within two weeks, the BALB/c nude mice bearing human-derived tumor xenograft of PDA or HCC in the subcutaneous region were established.

3. Preparation and Characterization of Liposome

3.1 Preparation of Liposome

3.1.1 Preparation of LPGL Liposome (1) 3.0 mg of DPPC, 3.0 mg of DSPE-PEG2000-RGD, 2.0 mg of DSPE-PEG2000 and 2 mg of gemcitabine prodrug CP4126 were dissolved in 3 mL of chloroform in a 10 ml of round bottom flask, the organic solvent was removed by rotary evaporation under reduced pressure at 40° C., and a lipid film was obtained in the round flask.

(2) The lipid film was cooled to 4° C., 100 μL of perfluoropentane was added to immerse the lipid film, and 5 mL of glycerol-containing phosphate buffer saline (10 mM, pH=7.4, the volume fraction of glycerol was 10 v/v %) was added for hydration, the mixture was stirred with magnetic stirrer at 4° C. for 30 min, then the mixture was stirred with magnetic stirrer at 30° C. for 1 h in open round bottom flask, and the LPGL liposome dispersion was obtained.

3.1.2 Preparation of LGL Liposome (1) 3.0 mg of DPPC, 3.0 mg of DSPE-PEG2000-RGD, 2.0 mg of DSPE-PEG2000 and 2 mg of gemcitabine prodrug CP4126 were dissolved in 3 mL of chloroform in a 10 ml of round bottom flask, the organic solvent was removed by rotary evaporation under reduced pressure at 40° C., and a lipid film was obtained in the round flask.

(2) The lipid film was cooled to 4° C., and 5 mL of glycerol-containing phosphate buffer saline (10 mM, pH=7.4, the volume fraction of glycerol was 10 v/v %) was added for hydration, the mixture was stirred with magnetic stirrer at 4° C. for 30 min, then the mixture was stirred with magnetic stirrer at 30° C. for 1 h in open round bottom flask, and the LGL liposome dispersion was obtained.

3.1.3 Preparation of PGL Liposome (1) 4.8 mg of DPPC, 3.2 mg of DSPE-PEG2000 and 2 mg of gemcitabine prodrug CP4126 were dissolved in 3 mL of chloroform in a 10 ml of round bottom flask, the organic solvent was removed by rotary evaporation under reduced pressure at 40° C., and a lipid film was obtained in the round flask.

(2) The lipid film was cooled to 4° C., 100 μL of perfluoropentane was added to immerse the lipid film, and 5 mL of glycerol-containing phosphate buffer saline (10 mM, pH=7.4, the volume fraction of glycerol was 10 v/v %) was added for hydration, the mixture was stirred with magnetic stirrer at 4° C. for 30 min, then the mixture was stirred with magnetic stirrer at 30° C. for 1 h in open round bottom flask, and the PGL liposome dispersion was obtained.

3.1.4 Preparation of GL Liposome (1) 4.8 mg of DPPC, 3.2 mg of DSPE-PEG2000 and 2 mg of gemcitabine prodrug CP4126 were dissolved in 3 mL of chloroform in a 10 ml of round bottom flask, the organic solvent was removed by rotary evaporation under reduced pressure at 40° C., and a lipid film was obtained in the round flask.

(2) The lipid film was cooled to 4° C., and 5 mL of glycerol-containing phosphate buffer saline (10 mM, pH=7.4, the volume fraction of glycerol was 10 v/v %) was added for hydration, the mixture was stirred with magnetic stirrer at 4° C. for 30 min, then the mixture was stirred with magnetic stirrer at 30° C. for 1 h in open round bottom flask, and the GL liposome dispersion was obtained.

3.1.5 Preparation of LPL Liposome (1) 5.0 mg of DPPC, 3.0 mg of DSPE-PEG2000-RGD and 2.0 mg of DSPE-PEG2000 were dissolved in 3 mL of chloroform in a 10 ml of round bottom flask, the organic solvent was removed by rotary evaporation under reduced pressure at 40° C., and a lipid film was obtained in the round flask.

(2) The lipid film was cooled to 4° C., 100 μL of perfluoropentane was added to immerse the lipid film, and 5 mL of glycerol-containing phosphate buffer saline (10 mM, pH=7.4, the volume fraction of glycerol was 10 v/v %) was added for hydration, the mixture was stirred with magnetic stirrer at 4° C. for 30 min, then the mixture was stirred with magnetic stirrer at 30° C. for 1 h in open round bottom flask, and the LPL liposome dispersion was obtained.

3.1.6 Preparation of Cy5 or CY5.5-Labeled Liposome

The preparation of Cy5-labeled liposome dispersion or Cy5.5-labeled liposome dispersion was similar to the preparation of liposome dispersion as described above, the difference was that the 0.3 mg of DSPE-PEG2000 was replaced with 0.3 mg of Cy5-labeled DSPE-PEG2000 (DSPE-$PEG2000^{Cy5}$) or 0.3 mg of Cy5.5-labeled DSPE-PEG2000 (DSPE-$PEG2000^{Cy5}$) to obtain Cy5 or Cy5.5 labeled LPGL, LGL, PGL, GL or LPL liposome dispersion.

3.2 Characterization of Liposome

The particle size and zeta potential of the liposome were measured using a dynamic light scattering analyzer (Nano- ZS 90, Malvern). The refractive index of the liposome was selected to be 1.59 to determine the particle size by intensity percent (intensity %).

The morphology of the liposome was imaged by Cryo-transmission electron microscope (Cryo-TEM) (Talos F200C 200 kv, FEI Inc.) in a carbon-coated 200-mesh copper TEM grid.

The fluorescence spectra and fluorescence intensity of Cy5 or Cy5.5 labeled liposome were detected with a micro-plate reader (SpectraMax M5, Molecular Devices).

The liposome dispersion (1 mL) was dialysed (Mw cut-off 3.5 kDa) in 100 mL PBS solution (containing 5 vol % glycerol) for 24 h, and the concentration of CP4126 (molar equivalent to GEM) in dialyzate was determined by high performance liquid chromatography. The encapsulation efficiency (EE) and GEM-loading rate (LR) were respectively calculated using the equations (1) and (2). The loading content (LC) of perfluoropentane was measured using the gas chromatographic-mass spectrometric method and calculated using the equations (3):

$$\text{“}EE = \text{mass of GEM in liposome/mass of total GEM} \times 100\%\text{”} \quad (1)$$

$$\text{“}LR = \text{mass of GEM in liposome/mass of total (lipids} + CP4126) \times 100\%\text{”} \quad (2)$$

$$\text{“}LC = \text{volume of perfluoropentane/(volume of perfluoropentane} + \text{volume of } PBS) \times 100\%\text{”} \quad (3)$$

The encapsulation efficiency (EE) of liposome was >99.5%, and the GEM-loading rate (LR) was >9.5%.

Figure 1:
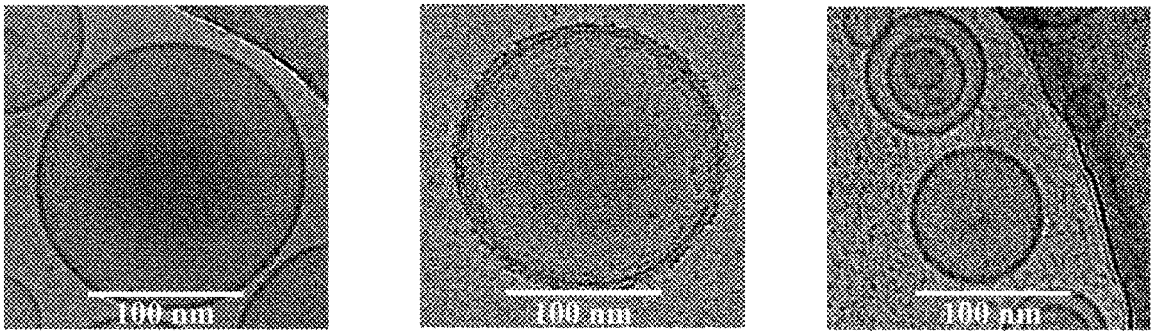
FIG. 1 shows the Cryo-transmission electron microscopy (Cryo-TEM) of LPGL liposome incubated in PBS 7.4 or mouse plasma, wherein the incubated mixture of LPGL liposome and PBS 7.4 or mouse plasma was treated with or without ultrasound stimulation (acoustic intensity: 2 $W/cm^2$, frequency: 3 MHz, duty cycle: 50%, duration time: 5 min).
Figure 2:
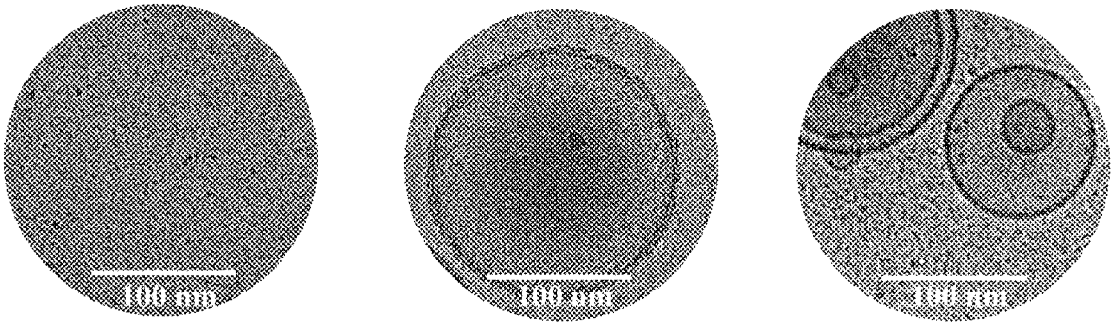
FIG. 2 shows the Cryo-transmission electron microscopy (Cryo-TEM) of PGL liposome incubated in mouse plasma, the incubated mixture of PGL liposome and mouse plasma was treated with or without ultrasound stimulation (acoustic intensity: 2 $W/cm^2$, frequency: 3 MHz, duty cycle: 50%, duration time: 5 min).

The FIG. 1 showed the Cryo-TEM of LPGL liposome under different treatment conditions. The particle size and zeta potentia of the GL, LGL, PGL and LPGL liposome incubated in PBS 7.4 buffer or mouse plasma were shown in Table 1. The table 1 showed compared with the particle size and zeta potential in PBS 7.4 buffer, the particle size of GL, LGL, PGL and LPGL liposome increased and the zeta potential of GL, LGL, PGL and LPGL liposome decreased in plasma, indicating GL, LGL, PGL and LPGL liposome absorbed plasma protein. The FIG. 2 showed the Cryo-TEM of PGL liposome incubated in mouse plasma before and after treatment with ultrasound stimulation (acoustic intensity: 2 W/cm$^2$, frequency: 3 MHz, duty cycle: 50%, duration time: 5 min). The FIG. 1 and FIG. 2 showed plasma protein was adsorbed on the surface of liposome to form protein corona after incubation of liposome with plasma, which further confirmed that plasma protein was adsorbed on the surface of liposome. The FIG. 1 and FIG. 2 further showed after the incubated mixture of LPGL or PGL liposome and plasma was treated with ultrasound stimulation (acoustic intensity: 2 W/cm$^2$, frequency: 3 MHz, duty cycle: 50%, duration time: 5 min), the protein corona on the surface of liposome disappeared.

The Cryo-TEM in FIG. 1 showed LPGL liposome had uniform monolayer lipid membrane in PBS 7.4 and plasma, a distinct ice-cloud shadow was within the perfluoropentane-loaded LPGL liposome, the loading content (LC) of perfluoropentane was 0.16 vol %.

Figure 3:
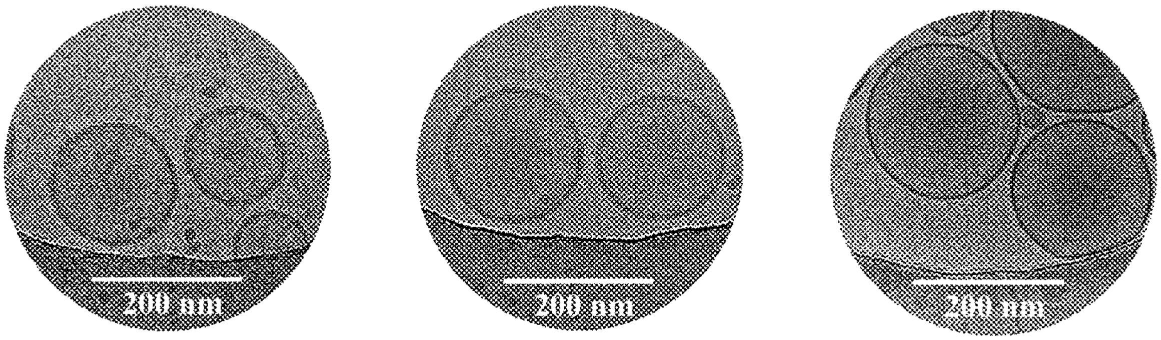
FIG. 3 shows the Cryo-transmission electron microscopy (Cryo-TEM) of GL, LGL and PGL liposome dispersion.

The Cryo-TEM of GL, LGL and PGL liposome dispersion was shown in FIG. 3. The FIG. 1 and FIG. 3 showed the GL and LGL liposome without perfluoropentane presented clear empty in the intra-capsule compared with LPGL liposome, while a distinct ice-cloud shadow of perfluoropentane was within the PGL liposome, the PGL liposome had uniform monolayer lipid membrane.

TABLE 1

Particle size and zeta potential of GL, LGL, PGL or LPGL liposome incubated in PBS 7.4 or plasma

| Liposome | Characterization | In PBS 7.4 | In plasma |
|---|---|---|---|
| GL | particle size (nm) | 149.4 ± 11.7 | 161.6 ± 12.2 |
| | zeta potential (mV) | −6.6 ± 2.1 | −10.2 ± 2.4 |
| LGL | particle size (nm) | 154.1 ± 14.5 | 166.7 ± 18.8 |
| | zeta potential (mV) | −8.3 ± 2.2 | −13.4 ± 2.8 |
| PGL | particle size (nm) | 185.7 ± 13.3 | 197.6 ± 15.1 |
| | zeta potential (mV) | −6.4 ± 1.4 | −9.8 ± 2.0 |
| LPGL | particle size (nm) | 188.4 ± 14.5 | 205.5 ± 12.2 |
| | zeta potential (mV) | −9.1 ± 2.7 | −13.7 ± 5.6 |

Note:
the incubation of liposome in plasma was performed as follows: GL, LGL, PGL or LPGL liposome dispersion was mixed with mouse plasma at the lipid/protein mass ratio of 1/50, and then incubated for 30 min in a shaker (60 rmp) at 37° C.

4. Protein Corona Preparation and Acquisition

Mice blood were collected via the orbital venous plexus, and then mixed with heparin solution (1 mg/mL, 50 μL). The mice plasma was separated from the blood by centrifuge at 5,000 rpm for 5 min at 4° C., and stored at −80° C. The plasma was centrifuged for 30 min at 20,000 g before use to remove any aggregated proteins. The protein concentration in plasma was 61 mg/mL using Enhanced BCA Protein Assay Kit with bovine serum albumin (BSA) as a standard. The Cy5-labeled GL, LGL, PGL or LPGL liposome was mixed with plasma at the lipid/protein mass ratio of 1/50 respectively, and then incubated in a shaker (60 rmp) at 37° C. 1 mL of the mixture was sampled and treated with or without ultrasound stimulation (acoustic intensity: 2 W/cm$^2$, frequency: 3 MHz, duty cycle: 50%, duration time: 5 min), and then immediately poured into the Sephadex G200 chromatography and separated with eluting 5-fold volume of PBS buffer. The eluate was lyophilized using a lyophilizer and then redissolved in 200 μL RIPA Lysis Buffer to obtain a solution of protein corona of liposome, the protein content in protein corona solution was determined using Enhanced BCA Protein Assay Kit with BSA as a standard.

Figure 4:
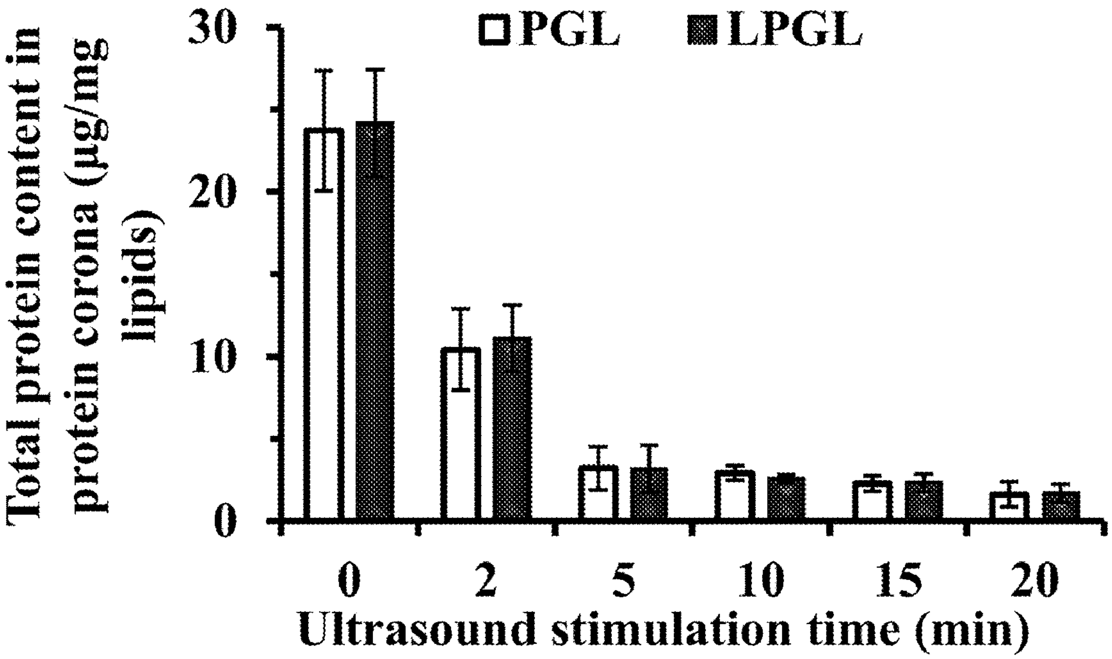
FIG. 4 shows the total content of protein in protein corona of PGL or LPGL liposome after the protein corona modified PGL or LPGL liposome was treated with ultrasound stimulation (acoustic intensity: 2 $W/cm^2$, frequency: 3 MHz, duty cycle: 50%) for different times.

Additionally, the Cy5-labeled PGL or LPGL liposome was mixed with plasma at the lipid/protein mass ratio of 1/50, and then incubated in a shaker (60 rmp) at 37° C. for 15 min, the mixture was sampled and treated without ultrasound stimulation, then the mixture was separated by Sephadex G200 chromatography to obtain PGL or LPGL liposome containing protein corona. The PGL or LPGL liposome containing protein corona was added to PBS 7.4 buffer solution, and the mixture was treated with ultrasound stimulation (acoustic intensity: 2 W/cm$^2$, frequency: 3 MHz, duty cycle: 50%) for different times, and then immediately poured into the Sephadex G200 chromatography and separated with eluting 5-fold volume of PBS buffer. The eluate was lyophilized using a lyophilizer and then redissolved in 200 μL RIPA Lysis Buffer to obtain a solution of protein corona of liposome, the protein content in protein corona solution was determined using Enhanced BCA Protein Assay Kit with BSA as a standard, the total content of protein in protein corona of PGL or LPGL liposome after the protein corona modified PGL or LPGL liposome was treated with ultrasound stimulation for different times was shown in FIG. 4. The FIG. 4 showed that ultrasound stimulation can remove up to 90% of protein corona on the surface of PGL or LPGL liposome.

Figure 5:
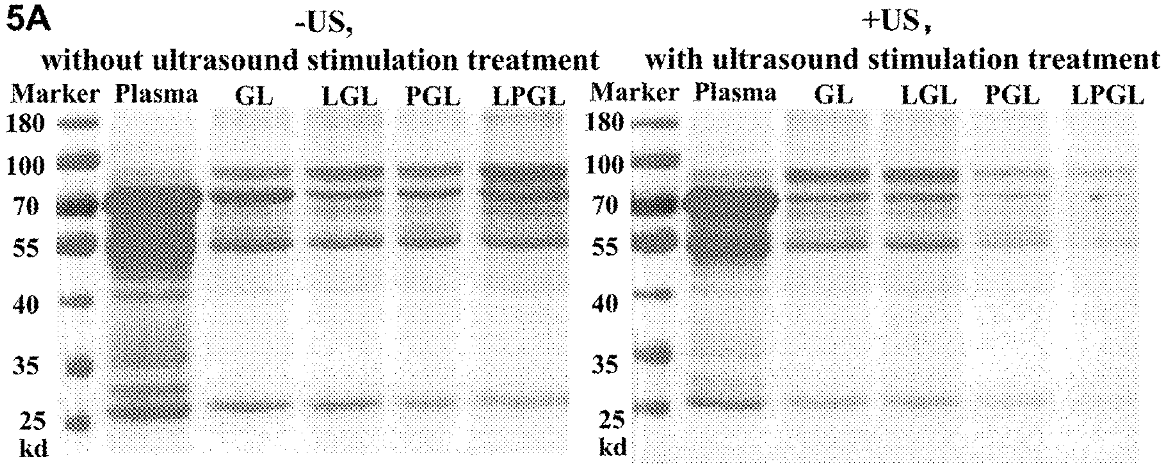
FIG. 5 shows the ultrasound stimulation removes protein corona on the surface of nanometer particle. (5A) shows the SDS-PAGE assay of protein corona on the surface of GL, LGL, PGL or LPGL liposome, the protein corona was obtained by separate the mixture of GL, LGL, PGL or LPGL liposome and plasma using Sephadex G200 chromatography, wherein the mixture of GL, LGL, PGL or LPGL liposome and plasma was treated with or without ultrasound stimulation; the (+US) means that the mixture of GL, LGL, PGL or LPGL liposome and plasma was treated with ultrasound stimulation (acoustic intensity: 2 $W/cm^2$, frequency: 3 MHz, duty cycle: 50%, duration time: 5 min); the (−US) means that the mixture of GL, LGL, PGL or LPGL liposome and plasma was treated without ultrasound stimulation. (5B) shows the HPLC-MS assay of the total content of protein in protein corona of GL, LGL, PGL or LPGL liposome, the protein corona of GL, LGL, PGL or LPGL liposome was obtained by separate the mixture of GL, LGL, PGL or LPGL liposome and mouse plasma using Sephadex G200 chromatography, wherein the mixture of GL, LGL, PGL or LPGL liposome and mouse plasma was treated with or without ultrasound stimulation (acoustic intensity: 2 W/$cm^2$, frequency: 3 MHz, duty cycle: 50%, duration time: 5 min).

5. Sodium Dodecyl Sulfate-Polyacrylamide Gel Electrophoresis (SDS-PAGE) Assay of Protein Corona For the SDS-PAGE assay of protein corona, the GL, LGL, PGL or LPGL liposome was mixed with mouse plasma at the lipid/protein mass ratio of 1/50 respectively, and then incubated in a shaker (60 rmp) for 15 min at 37° C., the mixture was treated with or without ultrasound stimulation (acoustic intensity: 2 W/cm$^2$, frequency: 3 MHz, duty cycle: 50%, duration time: 5 min), then the mixture was separated using Sephadex G200 chromatography to obtain a solution of protein corona of liposome. 20 μL of the protein corona solution was mixed with 4 μL SDS-PAGE sample loading buffer and applied onto a Tris-Gly Protein Gel (BeyoGel™ Plus Precast PAGE Gel). The electrophoresis was carried out in Tris-Glycine Running Buffer at 140 V for 60 min with Prestained Color Protein Standard Marker (10-180 kDa) as a molecular marker. The gel was then stained using SimplyBlue SafeStain and analyzed using the Azure c600 Imager The FIG. 5A in FIG. 5 showed the SDS-PAGE assay of protein corona on the surface of GL, LGL, PGL or LPGL liposome, the protein corona of GL, LGL, PGL or LPGL liposome was obtained by separate the mixture of GL, LGL, PGL or LPGL liposome and mouse plasma using Sephadex G200 chromatography, wherein the mixture of GL, LGL, PGL or LPGL liposome and mouse plasma was treated with or without ultrasound stimulation (acoustic intensity: 2 W/cm$^2$, frequency: 3 MHz, duty cycle: 50%, duration time: 5 min). As shown in FIG. 5A, the surface of GL, LGL, PGL and LPGL liposome absorbed a large amount of protein (molecular weight from 25 kDa to 180 kDa) after the liposome were incubated with plasma for 15 min, whereas compared with the protein content on the surface of PGL or LPGL liposome under the condition the mixture of PGL or LPGL liposome and plasma was treated without ultrasound stimulation, the protein content on the surface of PGL or LPGL liposome significantly decreased under the condition the mixture of PGL or LPGL liposome and plasma was treated with ultrasound stimulation, while the protein content on the surface of GL or LGL liposome had no significant change under the condition the mixture of GL or LGL liposome and plasma was treated with or without ultrasound stimulation, indicating the ultrasound stimulation could significantly reduce the protein content on the surface of PGL and LPGL liposome. Thus, the ultrasound stimulation could remove protein corona on the surface of PGL and LPGL liposome 6. High Performance Liquid Chromatography-Mass Spectrometry (HPLC-MS) Assay of Protein Corona The GL, LGL, PGL or LPGL liposome was mixed with mouse plasma at the lipid/protein mass ratio of 1/50 respectively, and then incubated in a shaker (60 rmp) for 15 min at 37° C., the mixture was treated with or without ultrasound stimulation (acoustic intensity: 2 W/cm$^2$, frequency: 3 MHz, duty cycle: 50%, duration time: 5 min), then the mixture was separated by Sephadex G200 chromatography to obtain a solution of protein corona of liposome. The protein corona solution was digested after mixing with trypsin in 1/50 mass ratio (enzyme/protein) and then diluted to 5-fold volume with 0.1% formic acid aqueous solution and spiked with 100 fmol/μL Hi3 *E. Coli* Standard for absolute quantification. Quantitative analysis of protein samples was performed using a HPLC coupled with a mass spectrometer (HPLC-MS).

The FIG. 5B in FIG. 5 showed the total content of protein in protein corona of GL, LGL, PGL or LPGL liposome using HPLC-MS, the protein corona of GL, LGL, PGL or LPGL liposome was obtained by separate the mixture of GL, LGL, PGL or LPGL liposome and mouse plasma using Sephadex G200 chromatography, wherein the mixture of GL, LGL, PGL or LPGL liposome and mouse plasma was treated with or without ultrasound stimulation (acoustic intensity: 2 W/cm$^2$, frequency: 3 MHz, duty cycle: 50%, duration time: 5 min). As shown in the FIG. 5B, the surface of GL, LGL, PGL and LPGL liposome absorbed a large amount of protein with the total content of 21-24p g/mg lipid under the condition the mixture of GL, LGL, PGL and LPGL liposome and plasma was treated without ultrasound stimulation. Whereas compared with the protein content on the surface of PGL or LPGL liposome under the condition the mixture of PGL or LPGL liposome and plasma was treated without ultrasound stimulation, the protein content on the surface of PGL or LPGL liposome decreased at least 80% under the condition the mixture of PGL or LPGL liposome and plasma was treated with ultrasound stimulation, while the protein content on the surface of GL and LGL liposome had no significant change under the condition the mixture of GL or LGL liposome and plasma was treated with or without ultrasound stimulation, indicating the ultrasound stimulation could significantly reduce the protein content on the surface of PGL and LPGL liposome. Thus, the ultrasound stimulation could significantly remove protein corona on the surface of PGL and LPGL liposome.

The LPGL liposome and mouse plasma were incubated, the mixture was treated without ultrasound stimulation, and the mixture was separated using Sephadex G200 chromatography to obtain protein corona of LPGL liposome, then the protein corona of LPGL liposome was analyzed using HPLC-MS, and the proteins in protein corona of LPGL liposome were identified and analyzed using the UniProt database (as shown in Table 2).

TABLE 2

The top 10 plasma proteins in the protein corona on the surface of LPGL liposome treated without ultrasound stimulation, the protein in protein corona were identified and analyzed using the HPLC and UniProt database

| Protein corona' composition of LPGL liposome | MW (kDa) | Content in protein corona (%) |
|---|---|---|
| 1. Alpha-2-macroglobulin | 163.2 | 8.31 |
| 2. Immunoglobulin heavy constant mu | 49.4 | 6.86 |
| 3. Serum albumin | 69.3 | 6.03 |
| 4. Prothrombin | 70.0 | 4.41 |
| 5. Apolipoprotein C-III | 10.8 | 3.14 |
| 6. Haptoglobin | 45.2 | 2.92 |
| 7. Immunoglobulin light chain | 24.0 | 2.71 |
| 8. C4b-binding protein alpha chain | 67.0 | 2.33 |
| 9. Apolipoprotein A-IV | 45.3 | 2.29 |
| 10. Alpha-1-antiproteinase | 47.6 | 1.93 |

Figure 6:
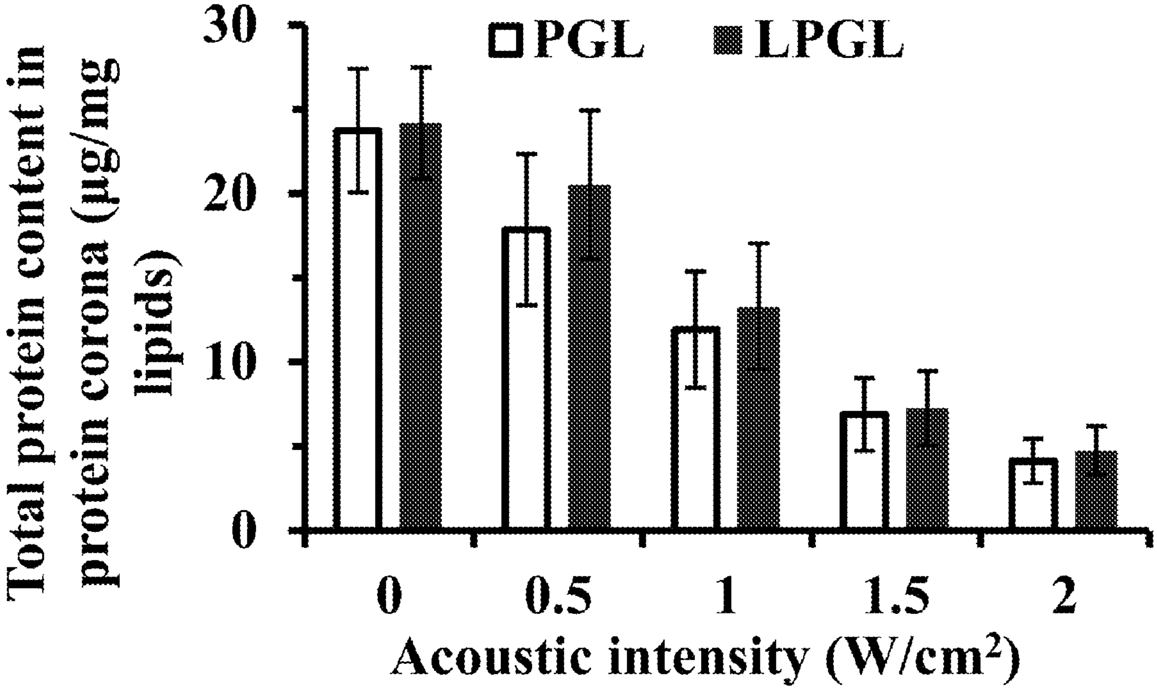
FIG. 6 shows the total content of protein in protein corona of PGL or LPGL liposome after the mixture of PGL or LPGL liposome and plasma was treated with ultrasound stimulation at different acoustic intensity, wherein, other parameters of ultrasound stimulation are as follows: the frequency is 3 MHz, the duty cycle is 50%, and the duration time is 5 min.

Additionally, the PGL or LPGL liposome were mixed with mouse plasma at the lipid/protein mass ratio of 1/50 respectively, and incubated in a shaker (60 rmp) at 37° C. for 15 min, the mixture was sampled and treated with ultrasound stimulation (frequency: 3 MHz, duty cycle: 50%, duration time: 5 min) at different acoustic intensity, then the mixture was separated by Sephadex G200 chromatography to obtain a solution of protein corona of PGL or LPGL liposome, the total content of protein in protein corona solution was determined using HPLC-MS (as shown in FIG. 6). The FIG. 6 showed the increase of acoustic intensity could enhance the ability of removing protein corona on the surface of the nanometer particle 7. Cellular Uptake BxPC3 cells ($1\times10^5$ cells/mL, 1 mL) were seeded in a 12-well plate and cultured for 24 h. The Cy5-labeled GL, LGL, PGL or LPGL liposome (equivalent to fluorescent lipids of 60 μg/mL, 20 μL) was mixed with 1 mL fresh serum-free medium or 10% FBS (fetal bovine serum)-containing medium for 30 min respectively. The cell culture medium was then replaced with the mixture of Cy5-labeled GL, LGL, PGL or LPGL liposome and serum-free medium or 10% FBS (fetal bovine serum)-containing medium, and treated with or without ultrasound stimulation (acoustic intensity: 2 W/cm$^2$, frequency: 3 MHz, duty cycle: 50%, duration time: 5 min), and continuously incubated for 1 h. The cells were rinsed with heparin sodium solution (2 mg/mL) three times, digested, harvested, and analyzed using flow cytometry to determine the mean fluorescence intensity of Cy5-labeled different liposomes in BxPC3 cells.

Figure 7:
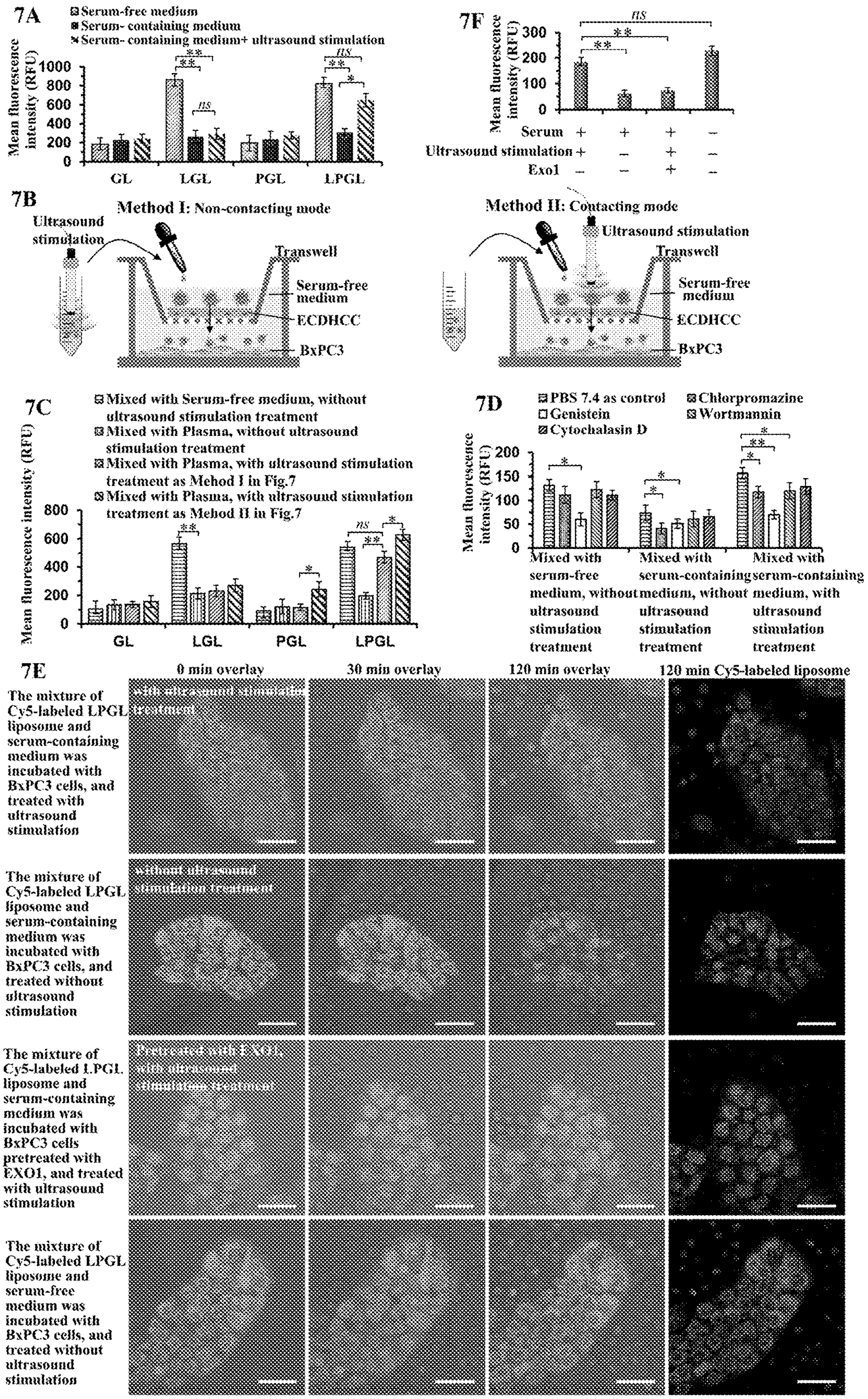
FIG. 7 shows the cellular uptake, transendothelial transport, endocytic pathway and transcytosis transport of liposome. (7A) shows the mean fluorescence intensity of Cy5-labeled GL, LGL, PGL or LPGL liposome in the BxPC3 cells using flow cytometry under the condition the mixture of Cy5-labeled GL, LGL, PGL or LPGL liposome and serum-free medium or 10% FBS (fetal bovine serum)-containing medium is incubated with BxPC3 cells and then treated with or without ultrasound stimulation (acoustic intensity: 2 W/$cm^2$, frequency: 3 MHz, duty cycle: 50%, duration time: 5 min); wherein, the "serum-free medium" means the mixture of Cy5-labeled GL, LGL, PGL or LPGL liposome and serum-free medium is incubated with BxPC3 cells, and treated without ultrasound stimulation, then continuously incubated for 1 h, the mean fluorescence intensity of Cy5-labeled GL, LGL, PGL or LPGL liposome in BxPC3 cells was detected; the "serum-containing medium" means the mixture of Cy5-labeled GL, LGL, PGL or LPGL liposome and 10% FBS (fetal bovine serum)-containing medium is incubated with BxPC3 cells, and treated without ultrasound stimulation, then continuously incubated for 1 h, the mean fluorescence intensity of Cy5-labeled GL, LGL, PGL or LPGL liposome in BxPC3 cells was detected; "serum-containing medium+ultrasound stimulation" means the mixture of Cy5-labeled GL, LGL, PGL or LPGL liposome and 10% FBS (fetal bovine serum)-containing medium is incubated with BxPC3 cells, and treated with ultrasound stimulation (acoustic intensity: 2 W/$cm^2$, frequency: 3 MHz, duty cycle: 50%, duration time: 5 min), then continuously incubated for 1 h, the mean fluorescence intensity of Cy5-labeled GL, LGL, PGL or LPGL liposome in BxPC3 cells was detected. (7B) Two methods (method I and II) are designed to study transendothelial transport of liposome in ECDHCC cells, wherein, the ultrasound stimulation is performed in centrifuge tube (I) or apical compartment (II). (7C) shows the mean fluorescence intensity (MFI) of Cy5-labeled GL, LGL, PGL or LPGL liposome in BxPC3 cells in transwell system using flow cytometry under the condition the mixture of different Cy5-labeled GL, LGL, PGL or LPGL liposome and plasma or serum-free medium is added into apical compartment and treated without ultrasound stimulation, or the mixture of different Cy5-labeled GL, LGL, PGL or LPGL liposome and plasma is treated with ultrasound stimulation in non-contacting mode (method I as shown in FIG. 7B) or contacting mode (method II as shown in FIG. 7B). (7D) shows after pretreatment of BxPC3 with PBS7.4, chlorpromazine, genistein, wortmannin or cytochalasin D, the mixture of Cy5-labeled LPGL liposome and serum-containing medium or serum-free medium is incubated with BxPC3 cells, and treated with or without ultrasound stimulation (acoustic intensity: 2 W/$cm^2$, frequency: 3 MHz, duty cycle: 50%, duration time: 5 min), then incubated for 3 h, the mean fluorescence intensity of Cy5-labeled LPGL liposome in BxPC3 cells was determined using flow cytometry. (7E) shows BxPC3 cells was pretreated with or without exocytosis inhibitor EXO1, the mixture of Cy5-labeled LPGL liposome and serum-containing medium or serum-free medium was incubated with BxPC3 cells, and treated with or without ultrasound stimulation (acoustic intensity: 2 W/$cm^2$, frequency: 3 MHz, duty cycle: 50%, duration time: 5 min), then the dishes were washed with PBS and the new BxPC3 cells are added into confocal dish, and continuously incubated, the CLSM image of newly added cells was obtained at incubation time of 0 min, 30 min, and 120 min, wherein, the "scale bar"=50 μm. (7F) shows the mean fluorescence intensity (MFI) of Cy5-labeled LPGL liposome in the newly added BxPC3 cells at incubation time of 120 min(as shown in FIG. 7E) using flow cytometry, wherein, "serum" means the mixture of Cy5-labeled LPGL liposome and serum-containing medium is incubated with BxPC3 cells; "ultrasound stimulation" represents ultrasound stimulation (acoustic intensity: 2 W/$cm^2$, frequency: 3 MHz, duty cycle: 50%, duration time: 5 min) treatment; "EXO1" means BxPC3 cells are pretreated with exocytosis inhibitor EXO1; "+" represents selection or adoption; "−" means no selection or no adoption. *: $P<0.05$, **: $P<0.01$, "ns" represents Not Statistically.

The uptake efficiency of Cy5-labeled GL, LGL, PGL or LPGL liposome in BxPC3 cells under different conditions was shown in FIG. 7A of FIG. 7. The FIG. 7A showed the uptake efficiency of RGD-ligand modified LGL or LPGL liposome was significantly higher than that of GL or PGL liposome in BxPC3 cells under the condition that incubating the mixture of Cy5-labeled GL, LGL, PGL or LPGL liposome and serum-free medium with BxPC3 cells without ultrasound stimulation treatment. However, the uptake efficiency of RGD-ligand modified LPGL or LGL liposome in BxPC3 cells significantly decreased and was similar to that of GL or PGL liposome under the condition the mixture of Cy5-labeled GL, LGL, PGL or LPGL and 10% FBS (fetal bovine serum)-containing medium was incubated with BxPC3 cells and treated without ultrasound stimulation, indicating the protein corona adsorbed on the surface of LPGL or LGL liposome could significantly block the binding of RGD ligand to BxPC3 cell receptor, thus decreasing the uptake efficiency of RGD-ligand modified LGL or LPGL liposome in BxPC3 cells. Whereas, the uptake efficiency of RGD-ligand modified LPGL liposome in BxPC3 cells was enhanced again and was recovered to the same order of magnitude as those results in serum-free medium under the condition the mixture of Cy5-labeled LPGL liposome and 10% FBS (fetal bovine serum)-containing medium was incubated with BxPC3 cells and then treated with ultrasound stimulation (acoustic intensity: 2 W/cm$^2$, frequency: 3 MHz, duty cycle: 50%, duration time: 5 min), while the uptake efficiency of Cy5-labeled GL, LGL or PGL liposome in BxPC3 cells kept at a low level under the condition the mixture of Cy5-labeled GL, LGL or PGL liposome and 10% FBS (fetal bovine serum)-containing medium was incubated with BxPC3 cells and then treated with ultrasound stimulation (acoustic intensity: 2 W/cm$^2$, frequency: 3 MHz, duty cycle: 50%, duration time: 5 min). Thus, the results showed the ultrasound stimulation could overcome the masking effect of the protein corona on the RGD ligand of the LPGL liposome surface, and recover the uptake of LPGL liposome in BxPC3 cells mediated by RGD ligand on the surface of liposome.

8. Subcellular Distribution

BxPC3 cells ($1\times10^5$ cells/mL, 1 mL) were cultured in a confocal dish for 24 h. The nuclei were stained with Hoechst 33342 for 20 min, and the lysosomes were labeled with LysoTracker® Green DND26 for 30 min. The Cy5-labeled LPGL lysosome (equivalent to fluorescent lipids of 60 μg/mL, 20 μL) was mixed with 1 mL fresh serum-free medium or 10% FBS (fetal bovine serum)-containing medium for 30 min to obtain preincubated mixture. The BxPC3 cells were washed with PBS twice and added 1 mL preincubated mixture, and treated with or without ultrasound stimulation (acoustic intensity: 2 W/cm$^2$, frequency: 3 MHz, duty cycle: 50%, duration time: 5 min), and continuously incubated for 1 h. The subcellular distribution images were photographed using Confocal Laser Scanning Microscope (CLSM) with 405 nm, 488 nm, and 640 nm wavelength channels. The Mander's overlap coefficient of LPGL liposome with lysosomes after incubation were analyzed using the free, open-source image analysis software Cellprofiler V2.2.0.

The subcellular distribution of Cy5-labeled LPGL liposome under the condition the mixture of Cy5-labeled LPGL liposome and serum-free medium or 10% FBS (fetal bovine serum)-containing medium was incubated with BxPC3 cells and then treated with or without ultrasound stimulation was shown in FIG. 8. The FIG. 8A and FIG. 8B showed Cy5-labeled LPGL liposome was mainly distributed in the cytoplasm and rarely distributed in lysosome under the condition the mixture of Cy5-labeled LPGL liposome and serum-free medium was incubated with BxPC3 cells and treated without ultrasound stimulation, whereas more than 65% of intracellular LPGL liposome was distributed in lysosome under the condition the mixture of Cy5-labeled LPGL liposome and 10% FBS (fetal bovine serum)-containing medium was incubated with BxPC3 cells and treated without ultrasound. However, Cy5-labeled LPGL liposome was mainly distributed in the cytoplasm again under the condition the mixture of Cy5-labeled LPGL liposome and 10% FBS (fetal bovine serum)-containing medium was incubated with BxPC3 cells and treated with ultrasound stimulation (acoustic intensity: 2 W/cm$^2$, frequency: 3 MHz, duty cycle: 50%, duration time: 5 min). Thus, the results showed ultrasound stimulation could make protein corona modified LPGL liposome have excellent lysosomal escape ability and avoid lysosomal degradation, lysosomal escape could effectively prevent drug-loaded nanometer particle and the drug from being damaged and degraded by degradation enzymes in the lysosome, improve the stability of drug-loaded nanometer particle and the drug in the cell, and thus improve the therapeutic effect of drug on disease.

9. Transport Across Vascular Endothelial Cells

A Transwell system was used to investigate the transcellular transport ability of liposome in vascular endothelial cells. ECDHCC endothelial cells ($5\times10^5$/cells, 1 mL) were incubated in the apical compartment for 4 days to facilitate the formation of a dense cell layer. BxPC3 cells ($1\times10^5$ cells/mL, 1 mL) were seeded onto the basolateral compartment for 12 h. The apical compartment was placed onto the basolateral compartment for 6 h adaptive incubation. The Cy5-labeled GL, LGL, PGL or LPGL liposome (equivalent total lipids of 1.2 mg/mL, 2.5 mL) was respectively mixed with mouse plasma (2.5 mL) at the lipids/protein mass ratio of 1/50 or serum-free medium (2.5 mL), and then incubated for 30 min in a shaker (60 rmp) at 37° C. to obtain preincubated mixture of Cy5-labeled liposome and plasma or serum-free medium, the preincubated mixture of Cy5-labeled GL, LGL, PGL or LPGL liposome and plasma or serum-free medium was added to apical compartment containing serum-free medium, and treated without ultrasound stimulation, then incubated for 3 h in Transwell, the fluorescence intensity of the culture medium in basolateral compartment was determined using a microplate reader, and the BxPC3 cells were harvested and measured in terms of Cy5 fluorescence intensity using flow cytometry.

In order to differentiate the ultrasound stimulation-induced transport through the gaps between the endothelial cells or the ligand/receptor-mediated transendothelial cells transport, two manipulated method (as shown in FIG. 7B) were designed: (method I) the preincubated mixture of Cy5-labeled GL, LGL, PGL or LPGL liposome and plasma (equivalent to fluorescent lipids of 60 μg/mL, 20 μL) was firstly pretreated with ultrasound stimulation (acoustic intensity: 2 W/$cm^2$, frequency: 3 MHz, duty cycle: 50%, duration time: 5 min, ultrasound stimulation had no effect on ECDHCC endothelial cells) in the centrifuge tube, and subsequently added into the apical compartment (non-contacting mode); (method II) the preincubated mixture of Cy5-labeled GL, LGL, PGL or LPGL liposome and plasma (equivalent to fluorescent lipids of 60 μg/mL, 20 μL) was firstly added into the apical compartment, and subsequently pretreated with ultrasound stimulation (acoustic intensity: 2 W/$cm^2$, frequency: 3 MHz, duty cycle: 50%, duration time: 5 min, ultrasound stimulation caused cavitation effect on ECDHCC endothelial cells in the apical compartment) (contacting mode). The Transwell system was continually incubated for 3 h, the fluorescence intensity of the culture medium in basolateral compartment was determined using a microplate reader, and the BxPC3 cells were harvested and measured in terms of Cy5 fluorescence intensity by flow cytometry.

The transcellular transport ability of different liposome in ECDHCC endothelial cells under different conditions was shown in FIG. 7C of FIG. 7. The FIG. 7C showed LGL and LPGL liposome had the highest transcellular transport ability in ECDHCC endothelial cells under the condition the mixture of different Cy5-labeled GL, LGL, PGL or LPGL liposome and serum-free medium was added into apical compartment and treated without ultrasound stimulation, whereas the transcellular transport ability of LGL and LPGL liposome in ECDHCC endothelial cells decreased significantly under the condition the mixture of different Cy5-labeled LGL or LPGL liposome and plasma was added into apical compartment and treated without ultrasound stimulation. The transcellular transport ability of GL and PGL liposome in ECDHCC endothelial cells was low and had no significant change under the condition the mixture of different Cy5-labeled GL or PGL liposome and serum-free medium or plasma was added into apical compartment and treated without ultrasound stimulation. The transcellular transport ability of LPGL liposome in ECDHCC endothelial cells was different with different ultrasound stimulation treatment as follows: compared with the transcellular transport ability of liposome in ECDHCC endothelial cells under the condition the mixture of different Cy5-labeled liposome and plasma was added into apical compartment and treated without ultrasound stimulation, the ultrasound stimulation treatment of the preincubated mixture of Cy5-labeled liposome and plasma in the centrifuge tube (non-contacting mode) could significantly enhance the transcellular transport ability of LPGL liposome in ECDHCC endothelial cells and recover to the same level as that under the condition the mixture of Cy5-labeled LPGL liposome and serum-free medium was added into apical compartment and treated without ultrasound stimulation, while the transcellular transport ability of GL, LGL and PGL liposome in ECDHCC endothelial cells did not change significantly in non-contacting mode, indicating ultrasound stimulation could overcome the masking effect of the protein corona on the ligand (RGD) of the surface of LPGL liposome and recover the transvascular endothelial cell transport ability mediated by the binding of RGD ligand on the surface of LPGL liposome to the vascular endothelial cell receptor. However, in contacting mode that the preincubated mixture of Cy5-labeled liposome and plasma was added into the apical compartment and subsequently treated with ultrasound stimulation, the transcellular transport ability of LPGL liposome in ECDHCC endothelia cells was significantly higher than that in non-contacting mode, and was about 3-4 times of that of GL, LGL and PGL liposome in contacting mode, indicating that ultrasound stimulation could significantly enhance the transcellular transport ability of LPGL liposome in ECDHCC endothelia cells in contacting mode,

10. Endocytic Pathway in Tumor Cells

BxPC3 cells ($1\times10^5$ cells/mL, 1 mL) were cultured in 12-well plates for 24 h, and the culture medium was then replaced with 1 mL fresh serum-free medium. Chlorpromazine (50 μM, clathrin-mediated endocytosis inhibitor), genistein (200 μM, caveolae-mediated endocytosis inhibitor), wortmannin (5 μM, phosphatidylinositol 3-kinases-mediated macropinocytosis inhibitor), or cytochalasin D (5 μM, actin-polymerization inhibitor) was added to the medium for 2 h of incubation. Another group of BxPC3 cells without any endocytosis inhibitor treatment was cultured for 2 h as the control group. Next, the mixture of Cy5-labeled LPGL liposome (equivalent to fluorescent lipids of 60 μg/mL, 20 μL) and serum-containing medium or serum-free medium was respectively added into the plate, and subsequently treated with or without ultrasound stimulation (acoustic intensity: 2 W/$cm^2$, frequency: 3 MHz, duty cycle: 50%, duration time: 5 min). After incubation of 3 h, cells were washed, digested and collected into a centrifugal tube, and the mean fluorescence intensity was detected by flow cytometry.

After pretreatment of BxPC3 with different endocytosis inhibitors, the mean fluorescence intensity of Cy5-labeled liposome in BxPC3 cells using flow cytometry under the condition that the mixture of Cy5-labeled LPGL liposome and serum-containing medium or serum-free medium was incubated with BxPC3 cells and then treated with or without ultrasound stimulation was shown in FIG. 7D. The FIG. 7D showed compared with the control group without endocytosis inhibitor treatment of BxPC3 cells, the inhibition rate of chlorpromazine, genistein, wortmannin and cytochalasin D on the endocytosis of LPGL liposome in BxPC3 cells was 21.1%, 57.6%, 13.4% and 19.9%, respectively under the condition the mixture of Cy5-labeled LPGL liposome and serum-free medium was incubated with BxPC3 cells and treated without ultrasound stimulation, indicating the uptake of LPGL liposome in BxPC3 cells was mainly driven by caveolae-mediated endocytosis. However, the protein corona on the surface of LPGL liposome had a significant effect on the endocytosis inhibition rate of LPGL liposome under the condition that the mixture of Cy5-labeled LPGL liposome and serum-containing medium was incubated with BxPC3 cells and treated without ultrasound stimulation treatment. compared with the blank control group without endocytosis inhibitor treatment of BxPC3 cells, the inhibition rate of chlorpromazine, genistein, wortmannin and cytochalasin D on the endocytosis of LPGL in BxPC3 cells was 35.9%, 28.9%, 23.5% and 10.2%, respectively, indicating the uptake of LPGL liposome in BxPC3 cells was mixed uptake pathway of clathrin-mediated endocytosis, caveolae-mediated endocytosis and macropinocytosis in serum-containing condition. Compared with the control group without endocytosis inhibitor treatment of BxPC3 cells, the inhibition rate of chlorpromazine, genistein, wortmannin and cytochalasin D on the endocytosis of LPGL in BxPC3 cells was 24.4%, 52.5%, 24.8% and 17.0%, respectively under the condition the mixture of Cy5-labeled LPGL liposome and serum-containing medium was incubated with BxPC3 cells and then treated with ultrasound stimulation treatment, indicating ultrasound stimulation could remove protein corona on the surface of LPGL liposome.

11. Transcytosis Transport in Tumor Cells

BxPC3 cells ($1\times10^5$ cells/mL, 1 mL) were cultured in a confocal dish for 24 h, and the culture medium was then replaced with 1 mL fresh serum-free medium. Next, the mixture of Cy5-labeled GL, LGL, PGL or LPGL liposome (equivalent to fluorescent lipids of 60 μg/mL, 20 μL) and serum-containing medium or serum-free medium was respectively added into the confocal dish, and subsequently treated with or without ultrasound stimulation (acoustic intensity: 2 W/cm$^2$, frequency: 3 MHz, duty cycle: 50%, duration time: 5 min). After incubation of 3 h, the dishes were washed twice with PBS. A total of $1\times10^5$ fresh cells in 1 mL of fresh serum-free medium was added to the dishes. The mixed cells were continuously incubated for 0 min, 30 min, and 120 min. The transcellular transport of liposome from previously added cells to newly added cells was photographed at incubation time of 0 min, 30 min, and 120 min with a CLSM using 640 nm excitation wavelength. Then the newly added cells at 120 min of incubation were washed away and collected into a centrifugal tube, and detected using flow cytometry. Meanwhile, BxPC3 cells pretreated with an exocytosis inhibitor EXO1 (20 μM) were tested using the same method to investigate the inhibition of transcellular transport.

Figure 9:
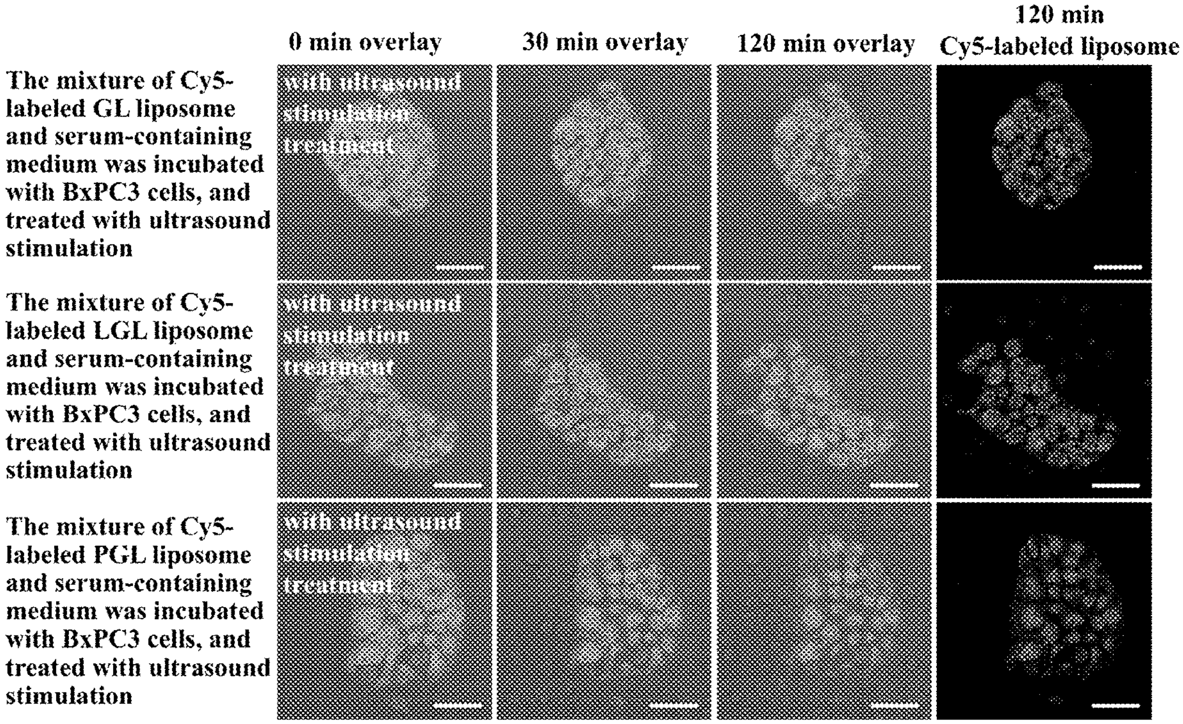
FIG. 9 shows the mixture of Cy5-labeled GL, LGL or PGL liposome and serum-containing medium was incubated with BxPC3 cells, and treated with ultrasound stimulation (acoustic intensity: 2 W/$cm^2$, frequency: 3 MHz, duty cycle: 50%, duration time: 5 min), then the dishes were washed with PBS and the new BxPC3 cells are added into confocal dish, and continuously incubated, the CLSM image of newly added cells was obtained at incubation time of 0 min, 30 min, and 120 min, the "scale bar"=50 μm.

BxPC3 cells was pretreated with or without exocytosis inhibitor EXO1, the mixture of Cy5-labeled GL, LGL, PGL or LPGL and serum-containing medium or serum-free medium was incubated with BxPC3 cells, and treated with or without ultrasound stimulation (acoustic intensity: 2 W/cm$^2$, frequency: 3 MHz, duty cycle: 50%, duration time: 5 min), then the new BxPC3 cells were added into confocal dish, the CLSM image of newly added cells at incubation time of 0 min, 30 min, and 120 min was shown in FIG. 7E and FIG. 9, and the mean fluorescence intensity (MFI) of Cy5-labeled LPGL liposome in the newly added BxPC3 cells using flow cytometry at incubation time of 120 min was shown in FIG. 7F. The 7E, FIG. 7F and FIG. 9 showed GL, LGL and PGL liposome could hardly be transported to the newly added BxPC3 cells under the condition the mixture of Cy5-labeled GL, LGL or PGL liposome and serum-containing medium was incubated with BxPC3 cells and treated with ultrasound stimulation treatment. Whereas LPGL liposome could effectively transport into newly added BxPC3 cells (the trend could be inhibited by exocytosis inhibitor EXO1) under the condition the mixture of Cy5-labeled LPGL liposome and serum-containing medium was incubated with BxPC3 cells and then treated with ultrasound stimulation (acoustic intensity: 2 W/cm$^2$, frequency: 3 MHz, duty cycle: 50%, duration time: 5 min), and the transport ability was similar to that of the condition that the mixture of Cy5-labeled LPGL liposome and serum-free medium was incubated with BxPC3 cells and treated without ultrasound stimulation, indicating ultrasound stimulation could overcome the masking effect of the protein corona on the RGD ligand of the LPGL liposome surface, and recover the transcytosis transport of LPGL liposome in BxPC3 cells mediated by RGD ligand.

Liposome could transport from one cell to another under different conditions. GL, LGL and PGL liposome could hardly be transported to newly added BxPC3 cells, while LPGL liposome could effectively transport to newly added tumor cells under the condition the mixture of liposome and serum-containing medium was incubated with BxPC3 cells and then treated with ultrasound stimulation, and the transcytosis transport of LPGL liposome could be inhibited by exocytosis inhibitor EXO1. The transcytosis transport ability of LPGL liposome significantly decreased under the condition the mixture of Cy5-labeled LPGL liposome and serum-containing medium was incubated with BxPC3 cells and treated without ultrasound stimulation. The results showed that ultrasound stimulation can effectively remove protein corona on the surface of the nanometer particle and recover the ligand-mediated transcytosis transport of LPGL.

12. Cytotoxicity and Apoptosis Test

The cytotoxicity of the liposome was tested on the three-dimensional (3D) multicellular tumor spheroids of BxPC3 or Huh7. The tumor spheroids were established using the hanging drop method. The mixture of LPGL, PGL, LGL, GL or free gemcitabine (GEM) and serum-containing medium were respectively added into the wells containing three-dimensional (3D) multicellular tumor spheroids of BxPC3 or Huh7 at the final testing concentrations (equivalent to GEM: 0~10 μM), and treated with ultrasound stimulation (acoustic intensity: 2 W/cm$^2$, frequency: 3 MHz, duty cycle: 50%, duration time: 5 min), then incubated for 72 h. Meanwhile, the LPL liposome with equimolar ratio to LPGL liposome was tested as a control. Afterward, the culture medium was replaced with a mixture of 90 μL fresh culture medium and 10 μL Alamar Blue Cell Viability Reagent, and was continuously incubated for 12 h. The sample plates were then detected using a plate reader at 530 nm excitation and 590 nm emission to obtain fluorescence intensity readouts. In addition, apoptosis induced by the liposome in spheroids were further determined by the TdT-mediated dUTP nick end labeling (TUNEL) assay, and the positive TUNEL-staining cells were examined by CLSM.

The inhibitory effect of free gemcitabine (GEM) and different liposomes on the three-dimensional (3D) multicellular tumor spheroids of BxPC3 or Huh7 under the condition the mixture of LPGL, PGL, LGL or GL liposome or free gemcitabine (GEM) and serum-containing medium was incubated with three-dimensional (3D) multicellular tumor spheroids of BxPC3 or Huh7 and then with ultrasound stimulation was shown in FIG. 10A and FIG. 10B of FIG. 10. The FIG. 10A and FIG. 10B showed free GEM and liposome had dose-dependent cytotoxicity against 3D multicellular tumor spheroids of BxPC3 or Huh7, and LPGL liposome had the highest cytotoxic activity, while GL, LGL and PGL liposome exhibited low cytotoxicity. The apoptosis induced by LPGL, PGL, LGL or GL liposome or free gemcitabine (GEM) on 3D multicellular tumor spheroids of BxPC3 or Huh7 using light microscope and TUNEL staining was showed in FIG. 10C. The FIG. 10C showed the spherical and smooth BxPC3 spheroid changed to irregular and collapsed morphology at the tumor periphery, and even the center of BxPC3 spheroids gone into erosion in the LPGL liposome treatment group, while the BxPC3 spheroids treated with PGL, LGL, GL liposome or free gemcitabine (GEM) showed no significant change in morphology. Moreover, the apoptotic cells were distributed in the entire spheroids after TUNEL staining in LPGL treatment group. On the contrary, there were few apoptotic cells distributed around the spheroid's periphery in PGL, LGL, GL liposome or free gemcitabine (GEM) treatment groups, indicating the LPGL liposome had significantly excellent tumor permeability compared with PGL, LGL and GL liposome under the ultrasound stimulation treatment.

13. Penetration in Tumor Spheroids

The 3D multicellular tumor spheroids of BxPC3 pretreated with or without exocytosis inhibitor EXO1 (20 μM) were transferred to a confocal dish containing fresh serum-free medium. The mixture of Cy5-labeled LPGL, PGL, LGL or GL liposome (equivalent to fluorescent lipids of 60 μg/mL, 30 μL) and fresh serum-containing medium were added, and treated with ultrasound stimulation (acoustic intensity: 2 W/cm$^2$, frequency: 3 MHz, duty cycle: 50%, duration time: 5 min), then incubated for 6 h. After washing with PBS, images were obtained with CLSM in XYZ-3D-stack at 25-μm intervals from apex to equator.

The mixture of different Cy5-labeled liposome and serum-containing medium was incubated with 3D multicellular tumor spheroids of BxPC3 pretreated with or without exocytosis inhibitor EXO1, and treated with ultrasound stimulation, the permeability of different Cy5-labeled liposomes into the 3D multicellular tumor spheroids of BxPC3 was shown in FIG. 10D and FIG. 10E of FIG. 10. The FIG. 10D showed GL, LGL or GL liposome was mainly distributed around the BxPC3 spheroid's periphery, while the LPGL liposome could deeply penetrate through the BxPC3 spheroids and distribute throughout the whole BxPC3 spheroids. Additionally, the FIG. 10E showed the mean integrated optical density (IOD) of fluorescence in two inner layers of 75 μm and 100 μm in 3D multicellular tumor spheroids of BxPC3 were analyzed to evaluate the penetration ability of liposome. The mean integrated optical density (IOD) of fluorescence in the inner area of BxPC3 spheroid treated with Cy5-labeled LPGL liposome was 2.7-10 times more than that in the GL, LGL or PGL liposome treatment group, indicating LPGL liposome had excellent tumor permeability, However, LPGL liposome was restricted to the periphery of the BxPC3 spheroids pretreated with EXO1, the mean integrated optical density (IOD) of fluorescence in two inner layers of 75 μm and 100 μm in 3D multicellular tumor spheroids of BxPC3 pretreated with EXO1 significantly decreased in LPGL liposome treatment group, indicating the exocytosis inhibitor EXO1 could significantly inhibit the permeability of LPGL liposome into the 3D spheroid of BxPC3. Thus, the penetration of LPGL liposome into the 3D spheroid of BxPC3 exhibited that the deep penetration of LPGL liposome into 3D spheroid of BxPC3 depended on the RGD ligand/receptor-mediated cell transport pathway, ultrasound stimulation could remove protein corona on the surface of LPGL liposome, overcome the masking effect of the protein corona on the RGD ligand of the LPGL liposome surface, and recover the transport mediated by RGD ligand on the surface of liposome, and promote the penetration of LPGL liposome into tumor.

14. Blood Clearance

BALB/c nude mice subcutaneously bearing human-derived tumor xenograft of PDA were intravenously injected with the Cy5-labeled GL, LGL, PGL or LPGL liposome (dose equivalent to GEM 10 mg/kg, 3 mice in each group), and then the tumor was treated with ultrasound stimulation (acoustic intensity: 2 W/cm$^2$, frequency: 3 MHz, duty cycle: 50%, duration time: 20 min). Blood samples (50 μL) were collected via the orbital venous plexus of mice at 2 min, 0.5 h, 1 h, 2 h, 4 h, 6 h, 8 h and 12 h after injection and mixed with heparin solution (1 mg/mL 50 μL). The supernatant samples were separated from the blood by centrifuge at 5,000 rpm for 5 min at 4° C. The supernatant samples were then diluted with acetonitrile (900 μL). The mixture was thoroughly vortexed, ultrasonicated, and centrifuged at 5,000 rpm for 5 min. Next, 500 μL of supernatant was removed and concentrated for high performance liquid chromatography-tandem-mass spectrometry (HPLC-MS/MS) analysis. The CP4126 content was calculated and pharmacokinetic parameters were analyzed.

After the tail vein injection of GL, LGL, PGL or LPGL liposome, the blood content of CP4126 at different time of post-injection was shown in FIG. 11. The FIG. 11 showed GL, LGL, PGL or LPGL liposome had excellent blood clearance half-life, GL and LGL liposome had similar blood clearance profiles with an elimination half-time about 1.33 h, which was longer than that of PGL liposome (1.02 h) and LPGL liposome (1.17 h).

15. Biodistribution, Penetration and In Vivo Imaging

BALB/c nude mice bearing human-derived tumor xenograft of PDA in the subcutaneous region were used to investigate tumor accumulation and penetration of liposome. The in vivo fluorescent imaging and biodistribution of liposome were performed in PDA xenograft-bearing BALB/c nude with inoculated PDA tumors on their right and left flanks. The mice bearing human-derived tumor xenograft of PDA were intravenously injected with the Cy5-labeled GL, LGL, PGL or LPGL liposome (dose equivalent to GEM 10 mg/kg, 3 mice in each group), the PDA tumor on the right flank was treated with ultrasound stimulation (acoustic intensity: 2 W/cm$^2$, frequency: 3 MHz, duty cycle: 50%, duration time: 20 min), and the PDA tumor on the left flank was not treated with ultrasound stimulation. Whole-body optical imaging was performed at 12 h of post-injection on a fluorescent spectral imager of Caliper IVIS Lumina II equipped with fluorescent filter sets (excitation/emission, 640/670 nm), then each mouse was intravenously injected with FITC (Fluorescein isothiocyanate)-labeled *Lycopersicon esculentum* lectin (FITC-Lectin, 0.05 mg per mouse), and cardiac perfusion with 2% glutaraldehyde solution was performed after 5 min post-injection of FITC-Lectin. The tumor tissues treated with or without ultrasound stimulation, heart, liver, spleen, lung, kidney and small intestine were then collected, the collected tissues were photographed using Caliper IVIS Lumina II fluorescence spectrometer and analyzed for fluorescence quantitative analysis using Living Image*-4.5 Software. The tumor treated with ultrasound stimulation was frozen in Tissue OCT-Freeze Medium. After sectioning into 10-μm thick slices, the penetration images of liposome in the tumor treated with ultrasound stimulation were photographed using CLSM and the fluorescence intensity gradient from tumor vessel to deep tumor was quantitatively analyzed using Image J software.

The biodistribution, tumor accumulation and penetration of different Cy5-labeled liposomes in BALB/c nude mice bearing human-derived tumor xenograft of PDA in the subcutaneous region were shown in FIG. 12. The ultrasound stimulation device as shown in FIG. 12A was used to study the biodistribution, tumor accumulation and penetration of different Cy5-labeled liposomes in BALB/c nude mice bearing human-derived tumor xenograft of PDA on the right and left flank, the PDA tumor on the right flank was treated with ultrasound stimulation (acoustic intensity: 2 W/cm$^2$, frequency: 3 MHz, duty cycle: 50%, duration time: 20 min) and the PDA tumor on the left flank was not treated with ultrasound stimulation after the mice bearing human-derived tumor xenograft of PDA were intravenously injected with different Cy5-labeled liposome. The biodistribution of different liposomes after 12 h of intravenous injection was shown in FIG. 12B and FIG. 12C. The FIG. 12B and FIG. 12C showed LPGL liposome had higher fluorescence intensity than other liposome in tumor treated with ultrasound stimulation after liposome was injected intravenously for 12 h, the fluorescence intensity of Cy5-labeled LPGL liposome in tumor treated with ultrasound stimulation was about 3.2-5.8-fold than that of Cy5-labeled GL, LGL or PGL liposome in tumor treated with ultrasound stimulation. However, the fluorescence intensity of LPGL and LGL liposome in tumor treated without ultrasound stimulation had no significant difference. The fluorescence intensity of Cy5-labeled LPGL liposome in tumor treated with ultrasound stimulation was about 5.11-fold than that of Cy5-labeled LPGL liposome in tumor treated without ultrasound stimulation, indicating ultrasound stimulation could significantly enhance the target accumulation of LPGL liposome in the tumor site. Meanwhile, the fluorescence intensity of Cy5-labeled LGL liposome in tumor treated with or without ultrasound stimulation was just 1.4-1.6-fold than that of Cy5-labeled GL liposome in the corresponding tumor treated with or without ultrasound stimulation, indicating ligand modification could hardly promote the effective accumulation of liposome in tumor site, which was due to the masking effect of protein corona on the ligand (RGD) of the surface of liposome. The fluorescence intensity of Cy5-labeled GL liposome in tumor treated with ultrasound stimulation was set as benchmark, and compared with the increased-amount of the fluorescence intensity of Cy5-labeled LGL and PGL liposome in tumor treated with ultrasound stimulation, ultrasound stimulation-reinitiated ligand/receptor-mediated transcytosis transport contributed about more than 70% of the increased-amount of the fluorescence intensity of Cy5-labeled LPGL liposome in tumor treated with ultrasound stimulation, ie. the enhancement of tumor accumulation of RGD-ligand modified LPGL liposome was mainly due to the reactivation of ligand/receptor-mediated cell transport under ultrasound stimulation treatment, which further indicated that ultrasound stimulation could remove protein corona on the surface of LPGL liposome, overcome the masking effect of the protein corona on the RGD ligand of the LPGL liposome surface, and recover the endocysis transport.

Before cardiac perfusion, the tumor vessels were stained with FITC-Lectin, the in vivo penetration of liposome in PDA tumor treated with ultrasound stimulation was analyzed by the co-localization of blood vessels and liposome (as shown in FIG. 12D and FIG. 12E). The FIG. 12D showed GL liposome was basically located at tumor vessels and hardly penetrated from tumor vessels, PGL and LGL liposome mainly distributed near tumor vessels, while LPGL liposome could travel away from the tumor vessels and penetrated into the deep tumor parenchyma. The FIG. 12E showed in the tumor treated with ultrasound stimulation, the fluorescence intensity of PGL and LGL liposome decayed rapidly with the distance from the tumor vessel to the tumor site and was hardly detectable beyond the distance of 50 μm from the tumor vessel to the tumor site, whereas the fluorescence signal of LPGL liposome was strong even at a distance of 100 μm from the tumor vessel to the tumor site, indicating LPGL liposome had excellent penetration ability from tumor vessels to tumor sites and had excellent deep tumor penetration under ultrasound stimulation treatment.

16. In Vivo Real-Time Vascular Extravasation Under Ultrasound Stimulation

BALB/c mice were subcutaneously inoculated human-derived tumor xenograft of PDA tumor beside an abdominal blood vessel to establish animal model bearing tumor. Once the tumor reached a size of 100 mm$^3$, the tumor was fixed on a microscope slide using a dorsal skinfold chamber (APJ Trading Co. Inc). The ultrasonic probe was fitted on the upside of the dorsal skinfold chamber with smearing the coupling agent. The Cy5-labeled GL, LGL, PGL or LPGL liposome (dose equivalent to GEM 10 mg/kg) were intravenously injected, then the tumor site was treated with ultrasound stimulation (acoustic intensity: 2 W/cm$^2$, frequency: 3 MHz, duty cycle: 50%, duration time: 20 min). The tumor site in each group was imaged using CLSM at 10 min, 30 min and 60 min after intravenous injection of different Cy5-labeled liposome, and the corresponding fluorescence intensity of tumor was calculated using Image J software. At 60 min after intravenous injection of Cy5-labeled liposome, cardiac perfusion was performed on the mice, and tumors were excised and fixed in 10-volume perfusate at 4° C. for at least 24 h. Next, the tumor samples were trimmed to small sections (approximately 2×2×2 mm), immersed in 7% agarose solution, and cut into 0.25-1 mm thick slice. The slices were washed with natrium cacodylic buffer (100 mM) and fixed in 1% osmic acid for 2 h. After staining with uranyl acetate at 37° C. for 48 h and gradient dehydration by acetone, the tumor tissues were embedded in epoxy resin, sectioned into slices (60-80 nm) and stained by lead citrate for transmission electron microscopy (TEM) observation.

The in vivo real-time vascular extravasation and tumor accumulation of different Cy5-labeled liposome in BALB/c nude mice bearing human-derived tumor xenograft of PDA were shown in FIG. 13. The FIG. 13 A showed the CLSM and ultrasound instrument was used to study the in vivo real-time vascular extravasation and tumor accumulation of different Cy5-labeled liposome in BALB/c nude mice bearing human-derived tumor xenograft of PDA, the tumor was fixed on the dorsal skinfold chamber, and the tumor vasculature were conspicuous around the tumor. After intravenous injection of different Cy5-labeled liposome, the tumor site was treated with ultrasound stimulation (acoustic intensity: 2 W/cm$^2$, frequency: 3 MHz, duty cycle: 50%, duration time: 20 min), the tumor vascular extravasation of different Cy5-labeled liposome at 10 min, 30 min and 60 min of post-injection of different Cy5-labeled liposome was shown in FIG. 13B and FIG. 13C. The FIG. 13B and FIG. 13C showed GL liposome could hardly extravasate from tumor vessel, and the fluorescence signals in the intratumor area was negligible, which further confirmed that PDA was a lowly permeable tumor with low Enhanced Permeability and Retention effect (EPR effect). LGL and PGL liposome could slightly extravasate from tumor vessel and mostly localized around the tumor vessel, while PLGL liposome could effectively extravasate from the tumor vessel and distributed into the tumor parenchyma, indicating ultrasound stimulation could effectively promote LPGL liposome extravasate from tumor vessel and accumulate in tumor parenchyma.

After intravenous injection of different Cy5-labeled liposome, then the tumor was treated with ultrasound stimulation, the tumor vasculature structure were analyzed by transmission electron microscopy (TEM) at 60 min after intravenous injection of different Cy5-labeled liposome (as shown in FIG. 13D). The PDA tumor was a lowly permeable solid tumor, the endothelial cells of PDA tumor vessels were well organized and tightly stacked. The FIG. 13D showed there were no abundant leaky gaps across or between the vascular endothelial cells of PDA tumor treated with different liposome, there was only one gap (indicated as arrow) could be characterized in the PGL treated tumor vascular wall, indicating GL, PGL, LGL and LPGL liposome could hardly extravasate from tumor vessel through the gaps across or between the vascular endothelial cells, ie, the GL, PGL, LGL and LPGL liposome could hardly extravasate from tumor vessel via the traditional Enhanced Permeability and Retention effect (EPR effect). Unexpectedly, the typical transcytosis transporter, vesicles (indicated as arrow), were abundant in the LPGL liposome-treated PDA tumor vascular wall, while there were very few vesicles distributed on the GL, PGL and LGL liposome-treated PDA tumor vascular wall. Vesicles were the only transporter in transendothelial transport. Thus, the results indicated ultrasound stimulation could effectively promote the extravasate of LPGL liposome from tumor vessels to tumor site via the ligand/receptor-mediated transcytosis transport pathway, while ultrasound stimulation hardly promote the extravasate of GL, PGL or LGL liposome from tumor vessels to tumor site via the ligand/receptor-mediated transcytosis transport pathway.

17. In Vivo Antitumor Activity

BALB/c nude mice bearing human-derived tumor xenograft of PDA in the subcutaneous region were selected and grouped into seven groups (n=6). Each group was intravenously injected with LPGL liposome dispersion (dose equivalent to GEM 10 mg/kg), PGL liposome dispersion (dose equivalent to GEM 10 mg/kg), LGL liposome dispersion (dose equivalent to GEM 10 mg/kg), GL liposome dispersion (dose equivalent to GEM 10 mg/kg), GEM PBS7.4 dispersion (dose equivalent to GEM 10 mg/kg), LPL liposome dispersion or PBS 7.4 buffer respectively every two days for a total of four times. The 16th day was the first time of intravenous injection administration. The tumor site of each group was treated with ultrasound stimulation (acoustic intensity: 2 W/cm$^2$, frequency: 3 MHz, duty cycle: 50%, duration time: 20 min) after post-injection. The width and length of the tumors and the bodyweight of mice were measured during the treatment. At the end of the experiment at 36 days, the blood was collected, then mice were euthanized, tumors were dissected and weighed. The therapeutic efficacy was evaluated by comparing tumor size in the experimental group and control group. The tumor inhibition rate=100%×(mean tumor weight of PBS group−mean tumor weight of experimental group)/mean tumor weight of PBS group. The dissected tumors were fixed with 4% neutral buffered paraformaldehyde and embedded in paraffin. Tissue sections of 5-μm thick were mounted onto glass slides and stained with hematoxylin-eosin (H&E), and then examined by light microscopy. The immunohistochemistry staining of Ki67 was tested to investigate the percentage of proliferous tumor cells positively stained in the examined field. Tissue sections were subjected to Ki67 staining using the Ki67-antibody Assay Kit according to the manufacturer's protocol. Apoptotic cells were also identified using TUNEL Apoptosis Assay Kit and examined using CLSM The antitumor activity of the free GEM or different liposome in BALB/c nude mice subcutaneously bearing human-derived tumor xenograft of PDA was shown in FIG. 14. The FIG. 14 A showed the establishment of BALB/c nude mice model bearing PDA tumor, experimental schedule and tumor treatment plan. The change of tumor volume with time in different treatment groups was shown in FIG. 14 B. The FIG. 14 B showed the continuous growth of tumor volume in mice treated with PBS 7.4 buffer and LPL liposome. In the free GEM, GL liposome, LGL liposome and PGL liposome group, the tumor growth was firstly delayed, but then recovered to grow when stopping administration. However, in the LPGL liposome treated group, the tumor volume decreased and the tumor growth was significantly inhibited continuously from the beginning of administration to the end of administration. The photo of mice and excised tumor in each group at the end of the 36-day experiment was shown in FIG. 14C and FIG. 14D. The FIG. 14C and FIG. 14D showed compared with other treatment groups, the tumors treated with LPGL liposome were significantly inhibited and a half of the LPGL-treated tumors were completely eradicated. At the end of the 36-day experiment, the average tumor weight of mice in each group was shown in FIG. 14E, the FIG. 14E showed the tumor inhibition rate of LPGL liposome was as high as 98.3%, which was much higher than that of free GEM, GL liposome, LGL liposome and PGL liposome. Moreover, the change of body weight of mice in each group during the treatment period was shown FIG. 14F, the values of white blood cell (WBC) and blood platelet (PLT) of mice in each group at the end of the 36-day experiment were shown in FIG. 14G and FIG. 14H. The FIG. 14F, FIG. 14G and FIG. 14H showed free GEM induced distinct body weight loss, and hematological damage on sharp decrease of white blood cell (WBC) and blood platelet, while the GL, PGL, LGL or LPGL liposome had no significant side effects on the mice in terms of the changes of body weight, the values of white blood cell (WBC) and blood platelet, indicating the GL, PGL, LGL or LPGL liposome had good biocompatibility and biosafety.

The H&E staining, immunohistochemistry (IHC) staining of Ki67 and TUNEL staining of the excised tumors were performed to investigate the mechanism of antitumor activity of the liposome (as shown in FIG. 14I and FIG. 15). The hematoxylin-eosin (H&E) stining showed the tumor treated with GEM, GL, LGL, PGL, and LPGL liposome had much less densely populated cells compared to those treated with LPL liposome and PBS. Additionally, LPGL-treated tumor presented a large number of apoptotic cells with abundant nuclear shrinkage and extensive intercellular cavums due to the ablation of tumor cells. Notably, compared with free GEM, GL, LGL and PGL liposome, LPGL liposome could significantly reduce the percentage of Ki67-positive tumor cell, indicating a better prognosis of LPGL liposome even after short-course of treatment. Moreover, in situ detection of DNA fragments using the TUNEL assay was performed to evaluate drug-induced cell apoptosis, which revealed a large number of apoptotic cells in LPGL-treated tumor compared with other groups. Interestingly, the apoptotic cells in LPGL-treated tumor were nearly distributed throughout the tumor parenchyma, whereas the apoptotic cells in free GEM, GL, LGL and PGL-treated tumors were merely existed around the tumor periphery. The results showed LPGL liposome could accumulate and penetrate deep into the PDA tumor and transport the active drugs throughout the tumor to induce cell apoptosis.

Example 2

The study of liposome and its characteristics and anti-tumor activity in Example 2 was the same as that in Example 1. The difference was that LPGL liposome and LGL liposome were prepared by replacing DSPE-PEG2000-RGD with DSPE-PEG2000-NGR. The DSPE-PEG2000-NGR refers to 1,2-distearoyl-sn-glycero-3-phosphoethanolamine-N-[methoxy (polyethylene glycol)-2000]-NGR targeting peptide, the amino acid sequence of NGR targeting peptide was Gly (glycine)-Gly (glycine)-Cys (cysteine)-Asn (asparagine)-Gly (glycine)-Arg (arginine)-Cys (cysteine) with the amino acid sequence GGCNGRC (SEQ ID NO: 2).

The Table 3 showed the characteristics of NGR-modified liposome, and the FIG. 16 and FIG. 17 showed the tumor accumulation and anti-tumor activity in BALB/c nude mice subcutaneously bearing human-derived tumor xenograft of HCC.

TABLE 3

Particle size and potential of NGR-modified LGL liposome and NGR-modified LPGL liposome

| Liposome | Characterization | In PBS 7.4 | In plasma |
|---|---|---|---|
| LGL | particle size (nm) | 160.6 ± 11.4 | 172.5 ± 10.2 |
| | zeta potential (mV) | −9.5 ± 3.1 | −14.3 ± 3.5 |
| LPGL | particle size (nm) | 181.3 ± 11.7 | 196.7 ± 10.4 |
| | zeta potential (mV) | −10.4 ± 3.3 | −15.9 ± 4.1 |

Note:
the incubation of liposome in plasma was performed as follows: NGR-modified LGL liposome or NGR-modified LPGL liposome dispersion was mixed with mouse plasma at the lipid/protein mass ratio of 1/50, and then incubated for 30 min in a shaker (60 rmp) at 37° C.

The FIG. 16 A showed after incubating NGR-modified LPGL liposome or NGR-modified LGL liposome with mouse mice plasma for 30 min, the total content of protein in the protein corona on the surface of NGR-modified LPGL liposome and NGR-modified LGL liposome was as high as about 28 μg/mg lipids. After the mixture of NGR-modified LPGL liposome or NGR-modified LGL liposome with mouse plasma was treated with ultrasound stimulation (+US, acoustic intensity: 2 W/cm$^2$, frequency: 3 MHz, duty cycle: 50%, duration time: 5 min), the total content of protein in the protein corona on the surface of NGR-modified LPGL liposome significantly decreased by 74.9%, whereas the total content of protein in the protein corona on the surface of NGR-modified LGL liposome kept unchanged, indicating the ultrasound stimulation could effectively remove protein corona on the surface of LPGL liposome. As shown in FIG. 16 B, the uptake efficiency of Cy5-labeled NGR-ligand modified LGL or NGR-ligand modified LPGL liposome in Huh7 cells was good under the condition the mixture of NGR-ligand modified LGL or NGR-ligand modified LPGL liposome and serum-free medium was incubated with Huh7 cells and treated without ultrasound stimulation, while the uptake efficiency of Cy5-labeled NGR-ligand modified LGL or NGR-ligand modified LPGL liposome in Huh7 cells significantly decreased under the condition the mixture of NGR-ligand modified LGL or NGR-ligand modified LPGL liposome and serum-containing medium was incubated with Huh7 cells and treated without ultrasound stimulation, indicating the protein corona on the surface of NGR-ligand modified LGL or LPGL liposome could significantly inhibit the NGR ligand/receptor mediated cell uptake of NGR-ligand modified LGL or LPGL liposome in Huh7 cells. Whereas, the uptake efficiency of Cy5-labeled NGR-ligand modified LPGL liposome in Huh7 cells was recovered under the condition the mixture of NGR-ligand modified LPGL liposome and serum-containing medium was incubated with Huh7 cells and then treated with ultrasound stimulation (+US, acoustic intensity: 2 W/cm$^2$, frequency: 3 MHz, duty cycle: 50%, duration time: 5 min), which was similar to the uptake efficiency of NGR-ligand modified LPGL liposome in Huh7 cells under the condition the mixture of NGR-ligand modified LPGL liposome and serum-free medium was incubated with Huh7 cells and treated without ultrasound stimulation treatment. The uptake efficiency of Cy5-labeled NGR-ligand modified LGL liposome in Huh7 cells was low under the condition the mixture of NGR-ligand modified LGL liposome and serum-containing medium was incubated with Huh7 cells and then treated with ultrasound stimulation (+US, acoustic intensity: 2 W/cm$^2$, frequency: 3 MHz, duty cycle: 50%, duration time: 5 min). The results showed the ultrasound stimulation could overcome the masking effect of the protein corona on the NGR ligand of the liposome surface, and recover the uptake efficiency mediated by NGR ligand on the surface of liposome.

The antitumor activity of the free GEM, GL liposome, NGR modified LGL liposome, PGL liposome, NGR modified LPGL liposome and PBS 7.4 in BALB/c nude mice bearing human-derived tumor xenograft of HCC in the subcutaneous region was shown in FIG. 17A-FIG. 17G.

The FIG. 17A showed the experimental schedule and tumor treatment plan in BALB/c nude mice model subcutaneously bearing human-derived HCC tumor. BALB/c nude mice bearing human-derived tumor xenograft of hepatocellular carcinoma (HCC) in the subcutaneous region were selected and grouped into six groups (n=9, wherein three mice of each group were selected to measure the accumulation content of gemcitabine triphosphate active metabolite (dFdCTP) in the tumor after 24 h of first intravenous injection). Same to the PDA model in the Example 1, after BALB/c nude mice subcutaneously bearing human-derived tumor xenograft of HCC were injected with free GEM PBS 7.4 buffer, GL liposome, NGR modified LGL liposome, PGL liposome, NGR modified LPGL liposome or PBS 7.4, the tumor site was treated with ultrasound stimulation (+US, acoustic intensity: 2 W/cm$^2$, frequency: 3 MHz, duty cycle: 50%, duration time: 20 min). At 24 h after firstly intravenous injection, the accumulation content of gemcitabine triphosphate active metabolite (dFdCTP) in the tumor was shown in FIG. 17B. As GEM could quickly be phosphorylated into its active metabolite of GEM triphosphate (dFdCTP) in tumor, so the dFdCTP was widely used as a quantitative index of GEM. The FIG. 17B showed the dFdCTP in NGR modified LPGL liposome-treated tumor was about 2.9-8.7-fold higher than that of free GEM, GL liposome, NGR modified LGL liposome, and PGL liposome, indicating that NGR modified LPGL had excellent tumor accumulation ability in HCC tumor.

The tumor size and the bodyweight of mice in each group was shown in FIG. 17C, FIG. 17D, FIG. 17E and FIG. 17F. The FIG. 17C, FIG. 17D, FIG. 17E and FIG. 17F showed the bodyweight of GEM-treated mice gradually decreased, while the bodyweight of GL liposome, NGR modified LGL liposome, PGL liposome and NGR modified LPGL liposome could recover to a normal level, indicating the side effect of liposome was negligible. At the end of the 34-day experiment, the mice serum was sampled, and the content of alanine aminotransferase (ALT), aspartate aminotransferase (AST), creatinine (CRE) and blood urea nitrogen (BUN) in the serum was detected to evaluate the in vivo hepatic and renal toxicity (as shown in Table 4). The Table 4 showed the content of AST, ALT, BUN and CRE in all liposome-treated mice was in the normal range, while those testing contents in GEM group were beyond the maximum of normal limit, indicating the GL liposome, NGR modified LGL liposome, PGL liposome and NGR modified LPGL liposome had good biocompatibility and biosafety. The FIG. 17D showed the tumor growth of mice treated with GL liposome, NGR modified LGL liposome, PGL liposome and NGR modified LPGL liposome was significantly inhibited compared to tumor treated with PBS or GEM during the treatments, but only the tumor treated with NGR modified LPGL liposome continued to decrease when stopping administration. Notably, compared with other treatment groups, the tumor treated with NGR-modified LPGL liposome was significantly inhibited and more than half of the tumor treated with NGR-modified LPGL liposome were completely eradicated, indicating the NGR-modified LPGL liposome had excellent anti-tumor efficiency and could eradicate tumor. The FIG. 17E and FIG. 17F showed NGR modified LPGL liposome achieved excellent antitumor efficiency, which was superior to those of free GEM, GL liposome, NGR modified LGL liposome, and PGL liposome, proving that NGR modified LPGL liposome had universal and efficient antitumor activity on solid tumors. The results of H&E staining and IHC staining of Ki67 as shown in FIG. 17G showed NGR modified LPGL liposome could significantly cause a large number of apoptotic cells and achieve a better prognosis even after short-course of treatment.

TABLE 4 the serum biochemical analysis of mice in different treatment group

| Treatment group | AST (U/L) | ALT (U/L) | BUN (mg/dL) | CRE (mg/dL) |
|---|---|---|---|---|
| PBS | 64.4 ± 5.9 | 46.2 ± 7.2 | 27.8 ± 7.4 | 0.46 ± 0.10 |
| GEM | 218.6 ± 25.3 | 81.1 ± 10.5 | 47.6 ± 5.0 | 0.68 ± 0.17 |
| GL | 75.5 ± 12.6 | 55.1 ± 8.8 | 24.0 ± 3.8 | 0.52 ± 0.12 |
| LGL | 78.0 ± 12.7 | 48.2 ± 7.0 | 30.5 ± 4.4 | 0.50 ± 0.11 |
| PGL | 86.1 ± 17.4 | 50.5 ± 9.4 | 29.6 ± 6.3 | 0.39 ± 0.15 |
| LPGL | 72.6 ± 11.9 | 54.3 ± 5.2 | 30.3 ± 4.7 | 0.44 ± 0.08 |
| Normal range | 50~215 | 27~78 | 18~45 | 0.3~0.6 |

The above described is an embodiment of the present invention designed for a case. It should be understood that those skilled in the art will be able to make various changes or modifications without departing from the principle of the invention, and these changes or modifications should also be considered as the protection scope of the invention

The invention claimed is:

1. A method for removing protein corona of protein corona modified nanometer particle, the method comprises the following steps:

subjecting the protein corona modified nanometer particle to ultrasound stimulation to remove the protein corona of the protein corona modified nanometer particle;

the nanometer particle comprises perfluoropentane;

the acoustic intensity of the ultrasound stimulation is 2 $W/cm^2$;

the frequency of the ultrasound stimulation is 3 MHz;

the duty cycle of the ultrasound stimulation is 50%;

the duration time of the ultrasound stimulation is 5 min;

the nanometer particle is ligand-modified liposome, the ligand-modified liposome is prepared by the following method, which comprises:

(i) dissolving 2.8-3.2 mg of DPPC, 2.8-3.2 mg of DSPE-PEG-ligand, 1.8-2.2 mg of DSPE-PEG and 1.8-2.2 mg of drug in an organic solvent in round bottom flask, and removing the organic solvent by rotary evaporation under reduced pressure to obtain a lipid film in round bottom flask, wherein the ligand is RGD polypeptide, the amino acid sequence of the RGD polypeptide is CRGDKGPDC, the DPPC refers to 1,2-dipalmitoyl-sn-glycero-3-phosphocholine, DSPE-PEG refers to 1,2-distearoyl-sn-glycero-3-phosphoethanolamine-N-[methoxy (polyethylene glycol)], the drug is gemcitabine elaidate having the following structure

CP4126

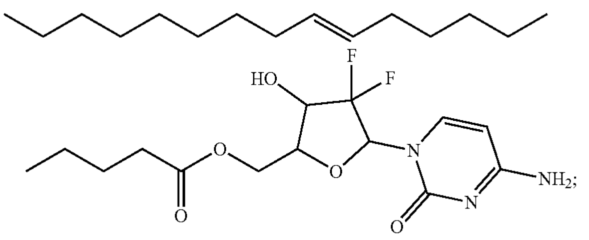

CP4126

(ii) cooling the lipid film to 2-6° C. and adding 90-110 μL of perfluoropentane to immerse the lipid film, then adding 4.5-5.5 ml of buffer solution to hydrate, stirring at 2-6° C., and then stirring at 28-32° C. in the open round bottom flask to obtain the ligand-modified liposome.

2. The method of claim 1, wherein the DSPE-PEG is DSPE-PEG2000;

the organic solvent is chloroform;

the buffer solution is glycerol-containing phosphate buffer saline;

the volume fraction of the glycerol is 8-12% in the glycerol-containing phosphate buffer saline;

the concentration of the glycerol-containing phosphate buffer saline is 8-12 mM, based on the concentration of phosphate radical;

the pH of the glycerol-containing phosphate buffer saline is 7.2-7.6.

3. The method of claim 1, wherein the subjecting is performed in protein-containing condition or protein-free condition.

4. The method of claim 3, wherein the protein-containing condition comprises blood, serum, plasma, and/or culture medium.

5. The method of claim 4, wherein the culture medium comprises serum, plasma and/or tissue protein-containing culture medium.

* * * * *